(12) United States Patent
Wilkinson

(10) Patent No.: US 12,394,506 B2
(45) Date of Patent: Aug. 19, 2025

(54) PLATFORM FOR COLLABORATIVE ANALYSIS OF ELECTRONIC RECORDS

(71) Applicant: The Government of the United States of America, as represented by the Secretary of Homeland Security, Washington, DC (US)

(72) Inventor: Thomas Wilkinson, Avenue, MD (US)

(73) Assignee: The Government of the United States of America, represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 18/200,227

(22) Filed: May 22, 2023

(65) Prior Publication Data
US 2023/0307103 A1   Sep. 28, 2023

Related U.S. Application Data

(63) Continuation of application No. 17/701,933, filed on Mar. 23, 2022, now Pat. No. 11,908,555.
(Continued)

(51) Int. Cl.
*G16H 10/60* (2018.01)
*G06F 16/20* (2019.01)
(Continued)

(52) U.S. Cl.
CPC ............ *G16H 10/60* (2018.01); *G06F 16/20* (2019.01); *G06F 16/25* (2019.01); *G06F 16/254* (2019.01);
(Continued)

(58) Field of Classification Search
CPC ........ G06F 16/254; G06F 16/20; G06F 16/25; G06F 17/40; G06F 21/6245;
(Continued)

(56) References Cited

U.S. PATENT DOCUMENTS 10,338,958 B1 * 7/2019 Kamboj ............... G06F 9/3851
10,642,856 B1 * 5/2020 Chu .................... G06F 21/6218
(Continued)

FOREIGN PATENT DOCUMENTS

GB    2371127 A    7/2002

OTHER PUBLICATIONS

Kai et al. "Authentic Data Space: A Security Data Co-Existence Schema Based on Tagging Technique," 2017, 2017 International Conference on Computer Systems, Electronics and Control, pp. 1472-1476 (Year: 2017).*
(Continued)

*Primary Examiner* — Charles D Adams
(74) *Attorney, Agent, or Firm* — Kelly G. Hyndman; Robert W. Busby

(57) ABSTRACT

Systems and methods are described, and an example system includes an AI enhanced multi-source health data integration logic that receives a first source electronic health record (EHR) data from a first EHR system and a second source EHR data from a second EHR system, and transforms, according to a knowledge representation schema, health-related information content of the first source EHR data and the second source EHR data to a first source transformed health data and second source transformed health data. The system includes a collaboration platform, configured to host a multi-source transformed health data database, including the transformed first source health data and the transformed second source health data, and hosts AI-enhanced, multiple level telecollaborative analyses by a plurality of participants of the multi-source transformed health data database, generating health management data.

34 Claims, 32 Drawing Sheets

Related U.S. Application Data

(60) Provisional application No. 63/164,659, filed on Mar. 23, 2021.

(51) Int. Cl.
    *G06F 16/25* (2019.01)
    *G06F 17/40* (2006.01)
    *G06F 21/62* (2013.01)
    *G06Q 10/00* (2023.01)
    *G06Q 90/00* (2006.01)
    *G16H 40/67* (2018.01)
    *G16H 50/20* (2018.01)
    *G16H 80/00* (2018.01)

(52) U.S. Cl.
    CPC .......... *G06F 17/40* (2013.01); *G06F 21/6245* (2013.01); *G06Q 10/00* (2013.01); *G06Q 90/00* (2013.01); *G16H 40/67* (2018.01); *G16H 50/20* (2018.01); *G16H 80/00* (2018.01)

(58) Field of Classification Search
    CPC .... G06F 21/6236; G16H 10/60; G16H 40/67; G16H 50/20; G16H 80/00; G06Q 10/00; G06Q 90/00
    See application file for complete search history.

(56) References Cited

U.S. PATENT DOCUMENTS

| | | | |
|---|---|---|---|
| 11,082,487 | B1 | 8/2021 | Jain et al. |
| 11,424,012 | B1 | 8/2022 | Rai |
| 11,514,289 | B1* | 11/2022 | Otte .................... G06N 20/00 |
| 2004/0236786 | A1 | 11/2004 | Medicke et al. |
| 2005/0262190 | A1* | 11/2005 | Mamou ................. G06Q 10/10 709/203 |
| 2008/0046292 | A1 | 2/2008 | Myers et al. |
| 2009/0006467 | A1 | 1/2009 | Visscher |
| 2009/0080408 | A1 | 3/2009 | Natoli et al. |
| 2009/0094674 | A1 | 4/2009 | Schwartz et al. |
| 2013/0159258 | A1* | 6/2013 | Belisle .................... G06F 16/23 707/654 |
| 2013/0238349 | A1 | 9/2013 | Sethumadhavan et al. |
| 2014/0350961 | A1 | 11/2014 | Csurka et al. |
| 2016/0210427 | A1 | 7/2016 | Mynhier et al. |
| 2016/0267150 | A1 | 9/2016 | Gubau i Forné et al. |
| 2017/0076046 | A1 | 3/2017 | Barnes et al. |
| 2018/0011922 | A1 | 1/2018 | Sethumadhavan et al. |
| 2018/0225345 | A1 | 8/2018 | Gilder et al. |
| 2019/0005200 | A1 | 1/2019 | Zimmerman et al. |
| 2019/0065683 | A9 | 2/2019 | Korpman et al. |
| 2020/0104723 | A1* | 4/2020 | Reissner ................. G06F 8/38 |
| 2020/0176098 | A1 | 6/2020 | Lucas et al. |
| 2020/0349288 | A1 | 11/2020 | Jun et al. |
| 2021/0104304 | A1 | 4/2021 | Davidovics et al. |
| 2021/0241871 | A1 | 8/2021 | Burnett et al. |
| 2022/0292372 | A1* | 9/2022 | Joshy .................... G06F 16/122 |
| 2023/0004574 | A1* | 1/2023 | Hu ......................... G06F 8/433 |

OTHER PUBLICATIONS

Geilm et al. "FactDAG: Formalizing Data Interoperability in an Internet of Production" IEEE Internet of Things Journal, vol. 7, No. 4, pp. 3243-3253, Apr. 2020 (Year: 2020).*

* cited by examiner

| 700 SDK | | |
|---|---|---|
| 702J Project & Task Management Tools | 1702K Import & Export Tools | 702L Data Integrity & Security Tools |
| 702G Policy Operationalization Tools | 702H Gaming Scenario Tools | 702I Query Engine |
| 702D Relation and Collaboration Tools | 702E Geospatial Tools | 702F AI/ML/DL Modeling Tools |
| 702A NLP, Text Analytics Tools | 702B Statistical Tools | 702C GUI, Data Viz Tools |

Fig. 7

800 Apps

804-M
⋮
804-7
804-6
804-5
804-4
804-3
804-2
804-1

App Market

802-K
⋮
802-7
802-6
802-5
802-4
802-3
802-2
802-1

Curated Contributions from Users and Third Parties

Fig. 8

900 GUI

904-S
⋮
904-2
904-1

Personalized Homepage: Selected Widgets
Low Barrier to Access,
High Barrier of Permissions

PLATFORM FOR COLLABORATIVE ANALYSIS OF ELECTRONIC RECORDS

CROSS-REFERENCE TO RELATED APPLICATIONS

This application is a continuation of U.S. patent application Ser. No. 17/701,933 filed on Mar. 23, 2022; which claims the benefit of priority from U.S. provisional application 63/164,659, filed Mar. 23, 2021, entitled "AI-ENHANCED, USER PROGRAMMABLE, SOCIALLY NETWORKED SYSTEM OF ELECTRONIC HEALTH RECORD (EHR) SYSTEMS," the disclosure which is incorporated by reference in its entirety.

STATEMENT OF GOVERNMENT INTEREST

The present invention was made by employees of the United States Department of Homeland Security in the performance of their official duties. The U.S. Government has certain rights in this invention.

FIELD

Embodiments disclosed herein generally relate to systems and methods for collaborative analysis of electronic records including electronic health records and health management.

BACKGROUND

The respective electronic health record (EHR) systems of the different components of the Department of Homeland Security (DHS), e.g., the Transportation Safety Agency (TSA), Federal Emergency Management Authority (FEMA), and DHS Headquarters, have differences, e.g., in system architecture, record standards, and user-interface, that can render it impractical to pool collection of common-interest informational content from any one component, e.g., the Coast Guard, with other DHS components or with third-parties, e.g., consultants, other contractors.

SUMMARY

In an embodiment, an example system provides for artificial intelligence (AI) enhanced, user programmable, and socially networked medical record exchange, and medical and public health situation assessment and response management, and the example system includes a multi-source health data integration logic, configured to perform operations including: receiving a first source electronic health record (EHR) data from a first EHR system and a second source EHR data from a second EHR system, transforming a health-related information content of the first source EHR data to a first source transformed health data, in accordance with a knowledge representation schema, and transforming a health-related information content of the second source EHR data to a second source transformed health data, in accordance with the knowledge representation schema. The example system further includes a collaboration platform, coupled to the multi-source health data integration logic, and configured to host a multi-source transformed health data database that includes the transformed first source health data and the transformed second source health data, and host a telecollaboration among a plurality of participants, regarding a content of the multi-source transformed health data database. The example system also includes a health data analysis and AI tool, hosted by the collaboration platform, configured to generate a health management data, based at least in part on an analyzing of the multi-source transformed health data database and at least a portion of the telecollaboration.

In another embodiment an example system provides for sovereignty protective extraction and collaborative analysis of information content of electronic health records and associated medical and public health situation assessment. Features of this example system include an information extracting, sovereignty protective wrapping logic, configured to perform operations including receiving an electronic health record (EHR) data from an EHR system, and wrapping, in an EHR system-specific sovereignty protective wrapper, a genericized form of a health-related information content of the EHR data. Features of this example system also include a staging database, coupled to the information extracting, sovereignty protective wrapping logic, and configured to store, in accordance with the EHR system-specific sovereignty protective wrapper, the genericized form of the health-related information content of the EHR data. Features of this example system also include a transform and concept alignment logic, coupled to the staging database, and configured to perform a transforming of the genericized form of the health-related information to a transformed interoperable health-related data; and include a collaboration platform, coupled to the transform and concept alignment logic, and configured to perform a hosting of a telecollaborative analysis of the transformed interoperable health-related data. In the example system, features of the hosting include a wrapping, in a telecollaboration participant specific sovereignty protective wrapper, a telecollaboration data associated with telecollaboration participant, and a maintaining during the telecollaborative analysis of the transformed interoperable health-related data, a sovereignty of the transformed interoperable health-related data in accordance with the EHR system-specific sovereignty protective wrapper, and a sovereignty of the telecollaboration data associated with the telecollaboration participant in accordance with the telecollaboration participant specific sovereignty protective wrapper.

Other features and aspects of various embodiments will be understood from reading the following detailed description in conjunction with the accompanying drawings. This summary is not intended to identify key or essential features, or to limit the scope of the invention, which is defined solely by the claims.

BRIEF DESCRIPTION OF THE DRAWINGS

FIG. 7 is a diagram illustrating an example configuration of a software development kit (SDK) for multi-contributor maintenance of a multi-tool suite of analysis apps, with an example plurality of analysis apps, that can be an AI enhanced multi-tool analysis resource for coupling to a multi-institutional knowledge database, for the FIG. 1 system and various other systems and methods for AI enhanced medical record exchange and common platform collaboration based medical and public health situation assessment, and health services resource and response management in accordance with one or more embodiments.

FIG. 8 is a diagram illustrating an example configuration of the curated applications block of the FIG. 1 example system, with a representative plurality of third party and user contributed applications, for the FIG. 1 system and various other systems and methods for AI enhanced medical record exchange and common platform collaboration based medical and public health situation assessment, and health services resource and response management in accordance with one or more embodiments.

FIG. 9 is a diagram illustrating an example configuration of the graphical user interface (GUI) block of the FIG. 1 system, with a representative plurality of widgets and other features, for the FIG. 1 system and various other systems and methods for AI enhanced medical record exchange and common platform collaboration based medical and public health situation assessment, and health services resource and response management in accordance with one or more embodiments.

DETAILED DESCRIPTION

Figure 1:
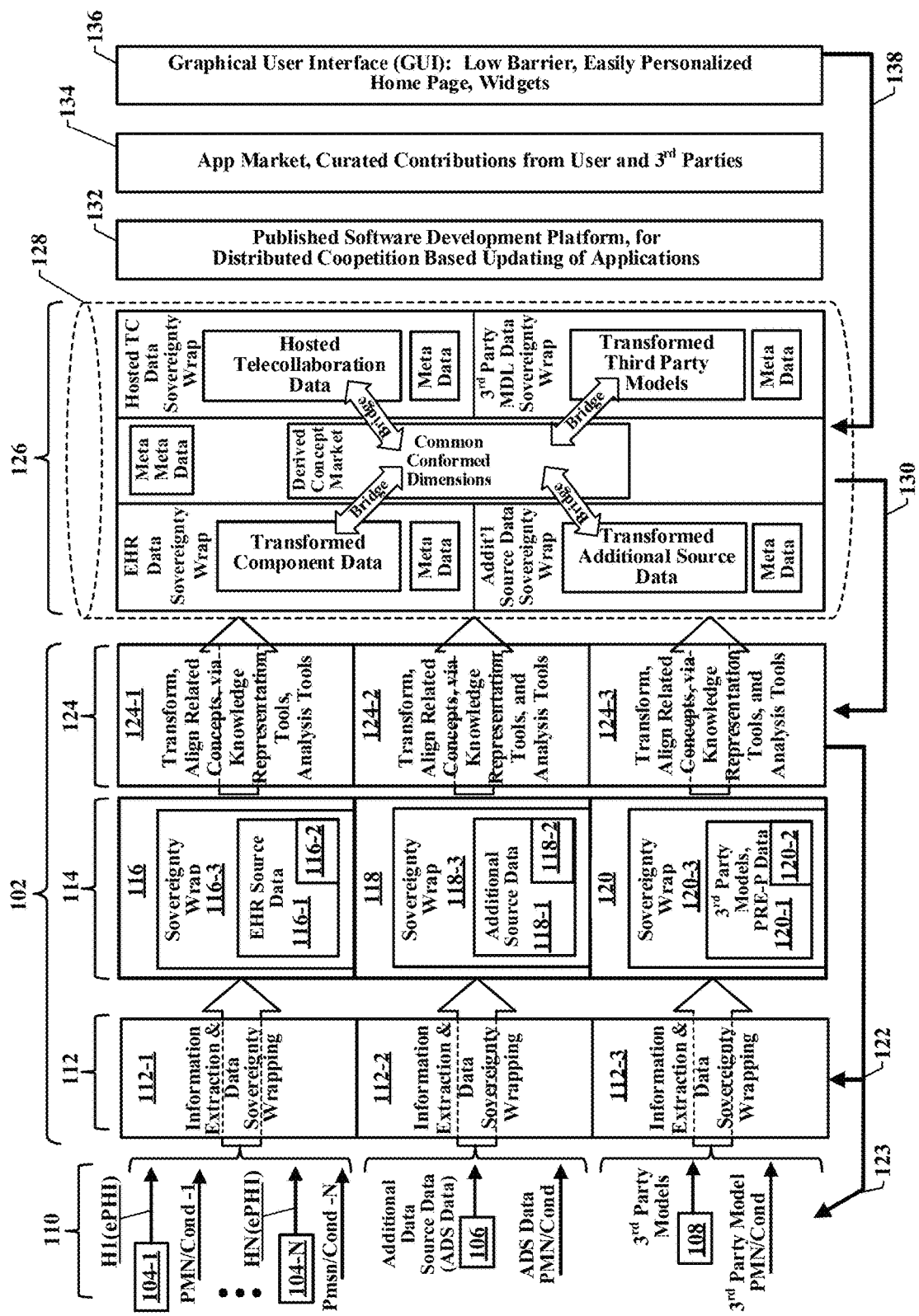
FIG. 1 is a functional block diagram of an example system-of-systems for artificial intelligence (AI) enhanced medical record exchange and common platform collaboration based medical and public health situation assessment, and health services resource and response management in accordance with one or more embodiments.

In the drawings, like reference numerals designate identical or corresponding parts throughout the several views. The drawings are generally not drawn to scale unless specified otherwise or illustrating schematic structures or flowcharts. As used herein, the words "a," "an" and the like generally carry a meaning of "one or more," unless stated otherwise.

In one example environment, a multi-source health data integration logic receives electronic health record (EHR) data from a plurality of different EHR data sources. Two or more of the EHR data sources may be mutually independent EHR management systems. The mutually independent EHR management systems may have respectively different architectures, may use respectively different file standards, and may have respectfully different configurations for user interface. The mutually independent EHR management systems can be respective EHR management systems of different components of a governmental organization, such as but not limited to the DHS. The mutually independent EHR management systems can be respectively different systems used by different private entities, or by different countries' governmental entities.

The multi-source health data integration logic's receiving of the EHR data from the mutually independent EHR management systems can be transparent to the different systems' users.

In an example environment, the multi-source health data integration logic can receive provenanced data, which can define, as well as selectively adapt and modify, data provenance rules from the various EHR management systems. The multi-source health data integration logic can then extract health and health related information for the EHR data received from the different EHR management systems and, using the received data provenance rules, wrap the extracted health and health related information in provenance rule compliant sovereignty wrappers, and store the wrapped health and health related information in a staging database. In an embodiment, the staging database can be configured to function as a data lake, which can feed a common platform and a multiple participant telecollaboration that can be hosted by and monitored or sensed by the common platform.

The common platform, the user interfaces to the common platform, as well as participant selection processes, and various resources supporting the common platform can be configured to a progression or evolution to what can be a target population and population makeup. The configurations can be such that the target population makeup can include, for example, participants of different skill sets, different individual and organizational positions, participants with access to different kinds processing resources. Configuration of common platform architecture, the user interfaces, and various processing resources can be for individuals as participants, and for organizations, formal or informal, private or governmental, as participants.

Embedded in or coupled to the common platform monitoring and sensing resources can be logic configured to construct, and dynamically update what can be "virtual institutional knowledge database," based on the sensed telecollaboration dynamics, e.g., inter-participant exchanges, analyses by individual participants, and analyses by groups of participants. The analyses can include, for example, neural networks.

An example system in accordance with one or more embodiments for AI enhanced, user programmable, socially networked medical record exchange, and medical and public health situation assessment and response management can include a multi-source health data integration logic and a collaboration platform coupled to the multi-source health data integration logic. The multi-source health data integration logic can be configured to perform operations including receiving a first source EHR data from a first EHR system and a second source EHR data from a second EHR system, transforming a health-related information content of the first source EHR data to a first source transformed health data, in accordance with a knowledge representation schema, and transforming a health-related information content of the second source EHR data to a second source transformed health data, in accordance with the knowledge representation schema. In an embodiment, features of the collaboration platform can include, but are not limited to, configuration to host a multi-source transformed health data database that includes the transformed first source health data and the transformed second source health data, and to host a telecollaboration among a plurality of participants, regarding a content of the multi-source transformed health data database. In an embodiment, a system can include a health data analysis and AI tool, which can be hosted by the collaboration platform, and can be configured to generate a health management data, based at least in part on an analyzing of the multi-source transformed heath data database and at least a portion of the telecollaboration.

In one or more embodiments, the health data analysis and AI tool can be a health data first analysis tool, and the system can further comprise a published software development kit, interfacing to the collaboration platform. The published software development kit can be configured to support a suite of health data analysis and AI tools, and the suite of health data analysis and AI tools can include the first health information analysis and AI tools. In an embodiment, the published software development kit can be further configured to be accessible to a plurality of third parties, for respective contributions to the suite of health data analysis and AI tools.

In one or more embodiments, the knowledge representation schema can be configured, the transforming the health-related information content of the first source EHR data to the transformed first source health data can be configured, or transforming the health-related information content of the second source EHR data to the transformed second source health data can be configured, or any combination or sub-combination thereof, to align a concept represented by the health-related information content of the first source EHR data with a concept represented by the health-related information content of the second source EHR data.

In one or more embodiments, the multi-source health data integration logic can be further configured to receive and to transform a healthcare model configuration data to a healthcare model transformed configuration data, in accordance with the knowledge representation schema. In an aspect, the collaboration platform that is further configured to host the healthcare model transformed configuration data, and the health data analysis and AI tool can be further configured to generate the health services management data further based, at least in part, on a healthcare model that is configured based, at least in part, on the healthcare model transformed configuration data.

In one or more embodiments, the multi-source health data integration logic can be further configured to generate, for the first source transformed health data, a first system sovereignty data, and to generate, for the second source transformed health data, a second system sovereignty data. In the one or more embodiments the collaboration platform can be further configured to include, in the hosting the multi-source transformed health data database, or in the hosting the telecollaboration, or both, an automated enforcement of rules of engagement in a usage, e.g., by the telecollaboration, of the transformed first source health data and the transformed second source health data. The rules of engagement can include a first rule of engagement for usage, e.g., by the telecollaboration of the transformed first source health data. The first rule of engagement can be based, at least in part, on the first system sovereignty data. The rules of engagement can include a second rule of engagement for usage, e.g., by the telecollaboration of the transformed second source health data. The second rule of engagement can be based, at least in part, on the second system sovereignty data.

The system may be further configured wherein the multi-source health data integration logic is configured to: receive at least a portion of the first EHR system sovereignty specification from the first EHR system; and receive at least a portion of the second EHR system sovereignty specification from the second EHR system.

The system may be further configured such that the multi-source health data integration logic comprises: a data extraction and wrapping logic, configured to generate a first genericized health-related data and a first metadata, based at least in part on an extracting of at least a portion of the health-related information content from the first EHR data. The data extraction and wrapping logic may be configured to generate a second genericized health-related data and a second metadata, based at least in part on an extracting of at least a portion of the health-related information content from the second source EHR data. The multi-source health data integration logic may comprise a staging database, configured to: store the first genericized health-related data, the first metadata, and the first system sovereignty data, and store the second genericized health-related data, the second metadata, and, in association with the second genericized health-related data and the second metadata, the second system sovereignty data. The multi-source health data integration logic may comprise a transformation logic, configured to transform, to the knowledge representation schema, the first genericized health-related data, the first metadata, the second genericized health-related data, and the second metadata.

In one or more embodiments, the data extraction and wrapping logic can be further configured to generate the first system sovereignty data as a first sovereignty wrapper, and the first sovereignty wrapper can include a first source provenance wrapper, a first source persistent encryption wrapper, and a first source rules of engagement wrapper. The data extraction and wrapping logic can be further configured to generate the second system sovereignty data as a second sovereignty wrapper, and the second sovereignty wrapper can include a second source provenance wrapper, a second source persistent encryption wrapper, and a second source rules of engagement wrapper.

One or more configurations of the system may be configured to provide sovereignty protective extraction and collaborative analysis of information content of electronic health records, and associated medical and public health situation assessment. Some configurations may include: an information extracting, sovereignty protective wrapping logic, configured to perform operations including, receiving an electronic health record (EHR) data from an EHR system, and wrapping, in an EHR system-specific sovereignty protective wrapper, a genericized form of a health-related information content of the EHR data. The system may include a staging database, coupled to the information extracting, sovereignty protective wrapping logic, and configured to store, in accordance with the EHR system-specific sovereignty protective wrapper, the genericized form of the health-related information content of the EHR data. The system may comprise a transform and concept alignment logic, coupled to the staging database, and configured to perform a transforming of the genericized form of the health-related information content to a transformed interoperable health-related data. The system may also comprise a collaboration platform, coupled to the transform and concept alignment logic, and configured to perform a hosting of a telecollaborative analysis of the transformed interoperable health-related data, the hosting including: a wrapping, in a telecollaboration participant specific sovereignty protective wrapper, a telecollaboration data associated with a telecollaboration participant, and a maintaining during the telecollaborative analysis of the transformed interoperable health-related data, a sovereignty of the transformed interoperable health-related data in accordance with the EHR system-specific sovereignty protective wrapper, and a sovereignty of the telecollaboration data associated with the telecollaboration participant in accordance with the telecollaboration participant specific sovereignty protective wrapper.

Some configurations of the system may include a published software development kit, interfacing to the collaboration platform, and supporting a suite of health data analysis and AI tools, accessible to a plurality of participants, for respective contributions to the suite of health data analysis and AI tools. Some configurations of the system may include the information extracting, sovereignty protective wrapping logic being further configured to receive a model data, defining a model and, in response, perform a wrapping, in a third-party supplier model information SP wrapping, a genericized form of an information content of the model data. Some configurations of the system may include the transform and concept alignment logic being further configured to also perform: configuring the transformed interoperable health-related data according to a knowledge representation schema supported by the collaboration platform, configuring the model data according to the knowledge representation schema, and aligning a concept represented by the transformed interoperable health-related data with a concept represented by the model data.

Various methods for artificial intelligence (AI) enhanced, user programmable, and socially networked medical record exchange, and medical and public health situation assessment and response management are contemplated. Such methods may include receiving a first source electronic health record (EHR) data from a first EHR system and a second source EHR data from a second EHR system; transforming a health-related information content of the first source EHR data to a first source transformed health data, in accordance with a knowledge representation schema; transforming a health-related information content of the second source EHR data to a second source transformed health data, in accordance with the knowledge representation schema: hosting, on a collaboration platform, a multi-source transformed health data database, which includes the transformed first source health data and the transformed second source health data; hosting a telecollaboration among a plurality of participants, regarding a content of the multi-source transformed health data database; and hosting a health data analysis and AI tool, by the collaboration platform, health information analysis and AI tool, the health data analysis and AI tool being configured to generate a health management data, based at least in part on an analyzing of the multi-source transformed health data database and at least a portion of the telecollaboration.

Methods of use may include interfacing to the collaboration platform a published software development kit, supporting a suite of health data analysis and AI tools, the published software development kit being accessible to a plurality of participants, for respective contributions to the suite of health data analysis and AI tools.

Methods of use may also include the transforming the health-related information content of the first source EHR data to the transformed first source health data being configured, or the transforming the health-related information content of the second source EHR data to the transformed second source health data being configured, or any combination or sub-combination thereof, to align a concept represented by the health-related information content of the first source EHR data with a concept represented by the health-related information content of the second source EHR data.

Methods of use may also contain receiving and transforming a healthcare model configuration data to a healthcare model transformed configuration data, in accordance with the knowledge representation schema; hosting the healthcare model transformed configuration data on the collaboration platform; and generating the health management data further based, at least in part, on a healthcare model that is configured based, at least in part, on the healthcare model transformed configuration data.

Method of use may include generating, for the first source transformed health data, a first system sovereignty data; generating, for the second source transformed health data, a second system sovereignty data; and the hosting the multi-source transformed health data database, or the hosting the telecollaboration, or a combination of the hosting the multi-source transformed health data database and the hosting the telecollaboration including: an automated enforcing of a first rule of engagement in a usage, by the telecollaboration, of the transformed first source health data, the first rule of engagement being based, at least in part, on the first system sovereignty data, and an automated enforcing of a second rule of engagement in a usage, by the telecollaboration, of the transformed second source health data, the second rule of engagement being based at least in part on the second system sovereignty data.

Method of use may include storing a first EHR system sovereignty specification, corresponding to the first EHR data; storing a second EHR system sovereignty specification, corresponding to the second EHR data; generating the first system sovereignty data based, at least in part, on the first EHR system sovereignty specification; and generating the second system sovereignty data based, at least in part, on the second EHR system sovereignty specification.

Method of use may contain the steps of receiving at least a portion of the first EHR system sovereignty specification from the first EHR system; and receiving at least a portion of the second EHR system sovereignty specification from the second EHR system.

Some of method of use may include: receiving a first provenance data, indicating at least an ownership of a health information content of the first EHR data; receiving a second provenance data, indicating at least an ownership of a health information content of the second EHR data; generating a first genericized health-related data and a first metadata, based at least in part on an extracting of at least a portion of the health information content from the first EHR data; generating a second genericized health-related data and a second metadata, based at least in part on an extracting of at least a portion of the health information content from the second EHR data; generating the first system sovereignty data based at least in part on the first provenance data; and generating the second system sovereignty data based at least in part on the second provenance data.

Some method of use may include generating the first system sovereignty data as a first sovereignty wrapper, the first sovereignty wrapper including a first source provenance wrapper, a first source persistent encryption wrapper, and a first source rules of engagement wrapper; and generating the second system sovereignty data as a second sovereignty wrapper, the second sovereignty wrapper including a second source provenance wrapper, a second source persistent encryption wrapper, and a second source rules of engagement wrapper In an embodiment, features including data curation provided by the disclosed combination of the multi-source health data integration logic, data extraction and sovereignty protective wrapping provided by the data extraction and wrapping logic, and multiple participant collaboration provided by a hosted by the virtual collaboration platform can include what can be referenced as AI enhanced medical record exchange. The medical record exchange feature can bring medical and contextual data, analytics, decisions, and collaboration from across multiple sources onto a single secure medical information platform. Features of medical record exchange include multilevel, persistent, embedded cybersecurity. The cybersecurity is provided, for example, by tightly sequestering electronic personal health information (ePHI) and limiting access to appropriate roles, data attributes, and dynamic policies across all workflows. The medical record exchange can track data provenance throughout the analysis pipeline and can use persistent encryption methods to automate enforcement of the rules of engagement that data owners have agreed upon.

Medical record exchange can accept the burden of data integration with minimal disruption to operations of the different source systems' users. Benefits of minimal disruption can include support, for example and without limitation, reaching across multiple individual components of a large organization, each having their own individual EHR systems, for individual operational decisions by the individual EHR systems, while delivering the necessary tools for evidence-based oversight, management, and coordination of medical activities across the entire organization. Medical record exchange provides, therefore, a sophisticated, usable, integration platform, without requiring a single commercial EHR for the entire organization.

Implementation can be a system of systems, agnostic to the specifics of its source systems, but able to detect and strengthen their interconnections and unify them as a single information framework built for analysis and collaboration. The design of the medical record exchange can leverage an array of tools of modern data science and AI to create functional interoperability across an organization's components' individual medical record systems, without mandating preconceived requirements, and thus freeing components to determine for themselves what tools and processes are best suited to meet their unique mission needs.

FIG. 1 shows a functional block schematic of an example of an electronic health record system 100 for medical and public health situation assessment and response management in accordance with one or more embodiments. Features of the system 100, in overview, can include but are not limited to AI-enhanced medical record exchange, extraction, genericizing and storing in a staging database the health information contents of EHR data from a plurality of EHR systems. Further features can include transformation logic, which can be configured for transforming the EHR data to a transformed EHR data, e.g., using a knowledge representation schema, and feeding the transformed EHR data to collaboration platform supported multi-user telecollaboration, which is described in more detail in later sections of this disclosure. The telecollaboration, as will be described include, via the platform, a suite of tools analysis for a per-project, per-case, per-task, and per-document-management. The hosted telecollaboration can further provide peer review and root cause analysis and automated delivery of relevant information to the right person at the right time. The analysis tools can include data integration, data modeling, data analysis, concept recognition, concept alignment, visualization, and decision support tools.

Features can include a monitoring of telecollaboration events and, e.g., via subscription terms, maintaining a database of participants' relevant credentials, based at least in such features, generating a multi-institutional knowledge database. The generation can be continuing, which can produce a dynamic updating of the multi-institutional knowledge database.

In an embodiment, the FIG. 1 system 100 can include a multi-source health data integration logic 102 configured to receive what can be large amounts of electronic health information (eHI) carried in EHRs, from a personal health information (ePHI), in various forms and file structures maintained by a plurality of different, mutually independent EHR systems, e.g., a first EHR system 104-1, second EHR system 104-2 . . . , and Nth EHR system 104-N (collectively "EHR systems 104"). The eHI can include electronic personal health information (ePHI) and can include other non-personal health information. The EHRs can be in various forms and file structures maintained by the different EHR systems 104. Additional resources and particular features and combinations thereof, described in more detail in subsequent paragraphs include resources supporting novel processes providing, but not limited to, extraction and transformation to a generic form of the information content and related metadata of the EHRs, and EHR system-specific, adaptable sovereignty protective wrapping of the generic transformed information content and related metadata. Additional features and combinations thereof can include resources supporting novel process providing but not limited to transform and concept alignment processes that transform the generic form of the information content and related metadata of the EHRs to a transformed interoperable data. The transform includes conversion or transformation of the multiple sourced health information and metadata to a genericized health-related data. The genericized health-related data can be transformed again to the interoperable data. In an embodiment, the interoperable data can be aligned to logic structure of a virtual data warehouse and collaboration platform, which can be configured to host, for example, multiple participant collaborative analyses and using platform supported knowledge representation schema of a described in greater detail in subsequent paragraphs.

Referring to FIG. 1, in an embodiment, the multi-source health data integration logic 102 can be configured to receive other health and health-related data from additional sources 106. In an aspect, the multi-source health data integration logic 102 can be configured to also receive third party model data from one or more third-party model suppliers 108. For purposes of description, operations and processes of receiving data from EHR systems 104, additional sources 106, and third-party model suppliers 108, e.g., collection, management, and supplying data to the multi-source health data integration logic 102, is represented on FIG. 1 as data curation 110.

In an embodiment the multi-source health data integration logic 102 can receive, associated with the ePHI from the EHR systems 104, the additional data from the additional data sources 106, and the model data from the third-party model suppliers 108. The multi-source health data integration logic can also receive source-specific permissions and conditions data from one or more of the above-identified data sources. For example, as shown in FIG. 1, the multi-source health data integration logic 102 can receive from the first EHR system 104-1 a first EHR system electronic source-specific permissions and conditions data (labeled "PMN/Cond-1"), hereinafter referenced as "first EHR PMN/CD," and can receive from the Nth EHR system 104-N another source-specific permissions and conditions data (labeled "PMN/Cond-N"), hereinafter referenced as "Nth EHR PMN/CD." For purposes of description, permissions and conditions data received from the different EHR systems 104 will be referenced collectively as "EHR permissions and conditions data, which will be alternatively recited as "EHR PMN/CD."

In an embodiment, the FIG. 1 multi-source health data integration logic 102 can receive, from the additional sources 106, permissions and conditions data, which is hereinafter referenced collectively as "additional sources permissions and conditions data" and, alternatively, as "ADS Data PMN/CD." In an embodiment, the FIG. 1 multi-source health data integration logic 102 can receive, from the third-party model suppliers 108, permissions and conditions data that is hereinafter referenced as "third party model sources permissions and conditions data" and, alternatively, "Third Party Model PMN/CD."

It will be understood that in the context of the present disclosure the above-introduced letter strings "PMD/CD," "EHR PMN/CD," and "ADS Data PMN/CD" are coined letter strings that serve only as reduced letter count representations, respectively, of the word sequences "source-specific permissions and conditions data," "EHR system source-specific permissions and conditions data," and "additional source, source-specific permissions and conditions data," and none of these coined letter strings, as used herein, possesses, imports, or applies any intrinsic meaning.

The EHR PMN/CD received at the multi-source health data integration logic 102 can include, identify, reference, define, specify, and/or embody (hereinafter collectively "include") respective EHR system sovereignty specifications. For example, the first EHR PMN/CD can include a first EHR system 104-1 sovereignty specification, the second EHR PMN/CD can include a second EHR system 104-2 sovereignty specification, and so forth, with the Nth EHR PMN/CD including an Nth EHR system 104-N sovereignty specification. The EHR system sovereignty specifications received from the EHR systems 104 can in turn include, identify, reference, define, specify, and/or embody (hereinafter collectively "include") respective EHR sovereignty rules. For example, the first EHR system 104-1 sovereignty specification can include first EHR system 104-1 sovereignty rules, the second EHR system 104-2 sovereignty specification can include second EHR system 104-2 sovereignty rules, and so forth, with the Nth EHR system 104-N sovereignty specification including Nth EHR system 104-N sovereignty rules.

In an embodiment the multi-source health data integration logic 102 can be configured such that new permissions and conditions data may not be required for each data received from the described sources. For example, the multi-source health data integration logic 102 can be configured such that, prior to a given reception of EHR data from an nth EHR system 104-n, an nth EHR system PMN/CD can be received and stored, and then used for subsequent EHR-n data. In an embodiment, the multi-source health data integration logic 102 can receive updated EHR permissions and conditions data from one or more of the EHR systems 104. In another embodiment, the multi-source health data integration logic 102 can receive data with embedded identifiers of permissions and conditions, referencing an earlier received set of permissions and conditions data.

In an embodiment, the multi-source health data integration logic 102 can be configured to store up to N different EHR system sovereignty specifications, and based at least in part on same, to generate, select, construct, assemble. or configure (hereinafter collectively "generate") appropriate EHR system-specific rules. The multi-source health data integration logic 102 can include, for example, as translation feature that can translate the stored EHR system sovereignty specifications to appropriate rules, protocols, and formats native to the multi-source health data integration logic 102.

In an embodiment, data ownership can be singular or multilateral, and new ownership with additional data sovereignty rules can accrue during data transformational processes. In an example accrual, ownership and sovereignty rules can be nested as value of the information content is added during data modeling.

In an embodiment, one or more of the EHR system 104 sources, or one or more of the additional sources 106, or one or more of the third part model sources 108, or any combination of such sources, can provide information without data sovereignty rules. In an embodiment the multi-source health data integration logic 102 can be configured with one or more default sets of sovereignty rules, and with default rule selection logic for configurations with more than one set of default sovereignty rules.

In an embodiment, system 100 features can include, but are not limited to, collecting, pooling, and virtual platform supporting of collective, collaborative, and multilevel analysis of received EHR system sourced information, while protecting the data sources' respective data sovereignty rules. System features for protecting data sovereignty rules can include features of the multi-source health data integration logic 102. Such features can include an information extraction and data sovereignty wrapping logic 112 and, coupled to the logic 112, a combined staging database 114. For brevity, the word string "information extraction and data sovereignty wrapping logic" will be alternatively recited in the remainder of this disclosure as "IE-DSW logic." It will be understood that, as used in this disclosure, "IE-DSW" is an arbitrary coined string that serves only as a reduced letter count representation of the word sequence "information extraction and data sovereignty wrapping," and, as used herein, does not possess, import, or apply any intrinsic meaning.

In an embodiment, the IE-DSW logic 112 can extract from the above-described data received from data curation 110, e.g., extract ePHI data from data sourced by the EHR systems 104, extract additional information, e.g., additional health and health-related information, from data sourced by the additional sources 106, and extract model data from data sourced by the third-party model suppliers 108. In an embodiment, the IE-DSW logic 112 can also translate the extracted information to what can be a generic information or knowledge representational language (hereinafter "generic form"). The IE-DSW logic 112 can, in an embodiment, wrap the generic form information in source-specific sovereignty protective wrappers, configured to provide sovereignty protection in accordance with the received rules and permissions data described above. Example protective wrapper configurations, features, and aspects are described in more detail in later paragraphs, e.g., in one or more paragraphs referencing FIG. 3. As will be understood from reading this disclosure in its entirety, in various embodiments sovereignty protective features can be overarching, and can extend beyond direct operations of the wrappers applied by the IE-DSW logic 112.

In an embodiment, the combined staging database 114 can include a staging database first logic portion configured to store a staging database first portion 116 of extracted, generic transformed information content of EHR data received from EHR systems 104 (which can include generic transformed EHR system sourced ePHI data 116-1 and generic transformed EHR metadata 116-2) and can include EHR system SP specification data 116-3. For purpose of description, the extracted, generic transformed EHR system sourced ePHI data 116-1 will be alternatively referenced as "GTR EHR system sourced ePHI" 116-1 and the generic transformed EHR metadata 116-2 will be alternatively referenced as "GTR EHR metadata" 116-2.

In an embodiment, the combined staging database 114 can include a staging database second portion 118 that can store the generic transformed additional source health data 118-1, generic transformed additional source metadata 118-2, and additional source SP specification data 118-3. As visible in FIG. 1, the combined staging database 114 can also include a staging database third portion 120 that can store the generic transformed third-party supplier model data 120-1, generic transformed third-party supplier metadata 120-2, and third-party supplier SP specification data 120-3.

It will be understood that the staging database first logic portion that stores the staging database first portion 116, the staging database second logic portion that stores the staging database second portion 118, and staging database third logic portion that stores the staging database third portion 120 are logic delineations, which are not intended as any limitation of hardware-software implementation or allocation of functionalities, hardware or software architecture of implementations.

Feedback loop 122 can provide feedback of primary data requirements to data sources, e.g., EHR systems 104, additional data sources 106, and third-party models suppliers 108.

Referring to FIG. 1, the multi-source health data integration logic 102 can include a transform and concept alignment logic 124. The transform and concept alignment logic 124 can be configured to transform the content of combined staging database 114 first logic section, for storage or hosting as transformed interoperable data 126, on a virtual data warehouse and collaboration platform 128, described in greater detail in subsequent paragraphs. Features of and processes performed in generating the transformed interoperable data, including the labeled bridge between the transformed component data and the derived concept market, and the respective bridges between the transformed additional sources data and the derived concept market, the hosted telecollaboration data and the derived concept market and the transformed third party model data and the derived concept market, are described in greater detail in reference to FIG. 5.

The transform and concept alignment logic 124 can include first logic section 124-1 configured to align, for the collaboration platform, related concepts in the different EHR data from EHR systems 104, and second logic section 124-2 configured to align, for the collaboration platform, related concepts in the different data received from the additional sources 106, and third logic section 124-3 configured to align related concepts in the model configuration data received from the third-party model suppliers 108.

Tools that can be applied by the transform and concept alignment logic 124 can include formal ontologies, e.g., Web Ontology Language (OWL), the National Information Exchange Model (NIEM), and other knowledge representation schemata. Tools that can be applied by the transform and concept alignment logic 124 can include non-ontological knowledge representations, e.g., an integrated phenotype reference model. Tools that can be applied by the transform and concept alignment logic 124 can include standardized vocabularies, e.g., Systematized Nomenclature of Medicine (SNOMED), AI tools such as machine learning (ML), and deep learning (DL), and data dictionaries.

In embodiment, the system 100 can include a feedback loop 130, which can provide feature engineering feedback from the virtual data warehouse and collaboration platform 128 to the transform and concept alignment logic 124.

In an embodiment, the system 100 can include a published software development kit (SDK) 132. Features of the published SDK 132 can include distributed competition based updating of applications implementing the above-described analysis tools. Features of the SDK 132 are described in more detail later in this disclosure, including description in reference to FIG. 7 of an example configuration.

In an embodiment, the system 100 can include an app market 134, which can provide for curated contributions from users and third parties. Various features of the app market 134 are described in more detail later in this disclosure, including description in reference to FIG. 8 of an example configuration. Such features include system-integral protection or tendency against obsolescence, by the app market 134 and by a combination of the app market 134 and the published SDK 132, e.g., particularly configuring the SDK 132 to promote, or inherently produce, or both, Application Programming Interface (API) supplier to API supplier competition.

In an embodiment the system 100 can include a Graphical User interface (GUI) 136. Features of the GUI 136 can include ready configurability, e.g., a low barrier to accessibility and easily personalized home page with user-added widgets. These and other features of the GUI 136 are described in more detail later in this disclosure, including description in reference to FIG. 9 of an example GUI implementation and an operational configuration thereof.

In an embodiment, the system 100 can include a feedback loop 138, which can be configured to feed back to the virtual data warehouse and collaboration platform 128 information regarding, for example, collaboration participants' patterns of using system 100 resources. The feedback loop 138 can be arranged, for example, within a combination that can include a monitor of the GUI 136 configured to detect GUI use information reflective of user patterns of using the apps on the app market 134 and interfaces to a form or such information or portions of such information may be obtained, for example, via monitoring the GUI 136.

Figure 2:
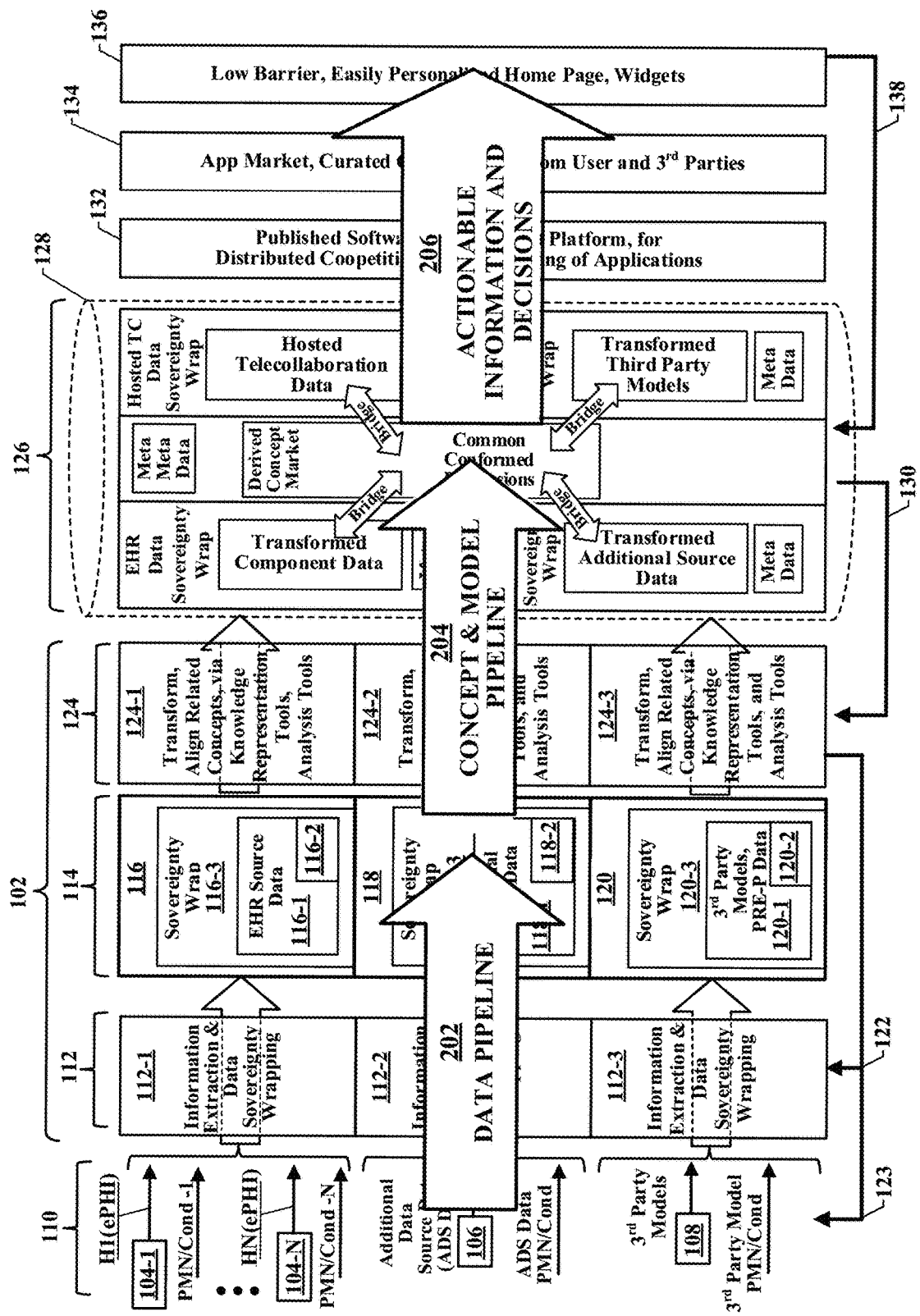
FIG. 2 shows by annotation of FIG. 1 a logic flow of data pipeline aspects and concept and model pipeline aspects, and of actionable information in various systems and methods for AI enhanced medical record exchange and common platform collaboration based medical and public health situation assessment, and health services resource and response management in accordance with one or more embodiments.

FIG. 2 is a flow diagram showing example flows through system 100, indicated by flow arrows superposed on a copy of the FIG. 1 functional block diagram of system 100. The process flows include a data pipeline flow 202, representing a concept and model pipeline flow 204. Decision pipeline flow 206 represents generation of actionable information for decisions by end users from processes on the example system for AI-enhanced health service resource and response management in accordance with various embodiments.

Figure 3:
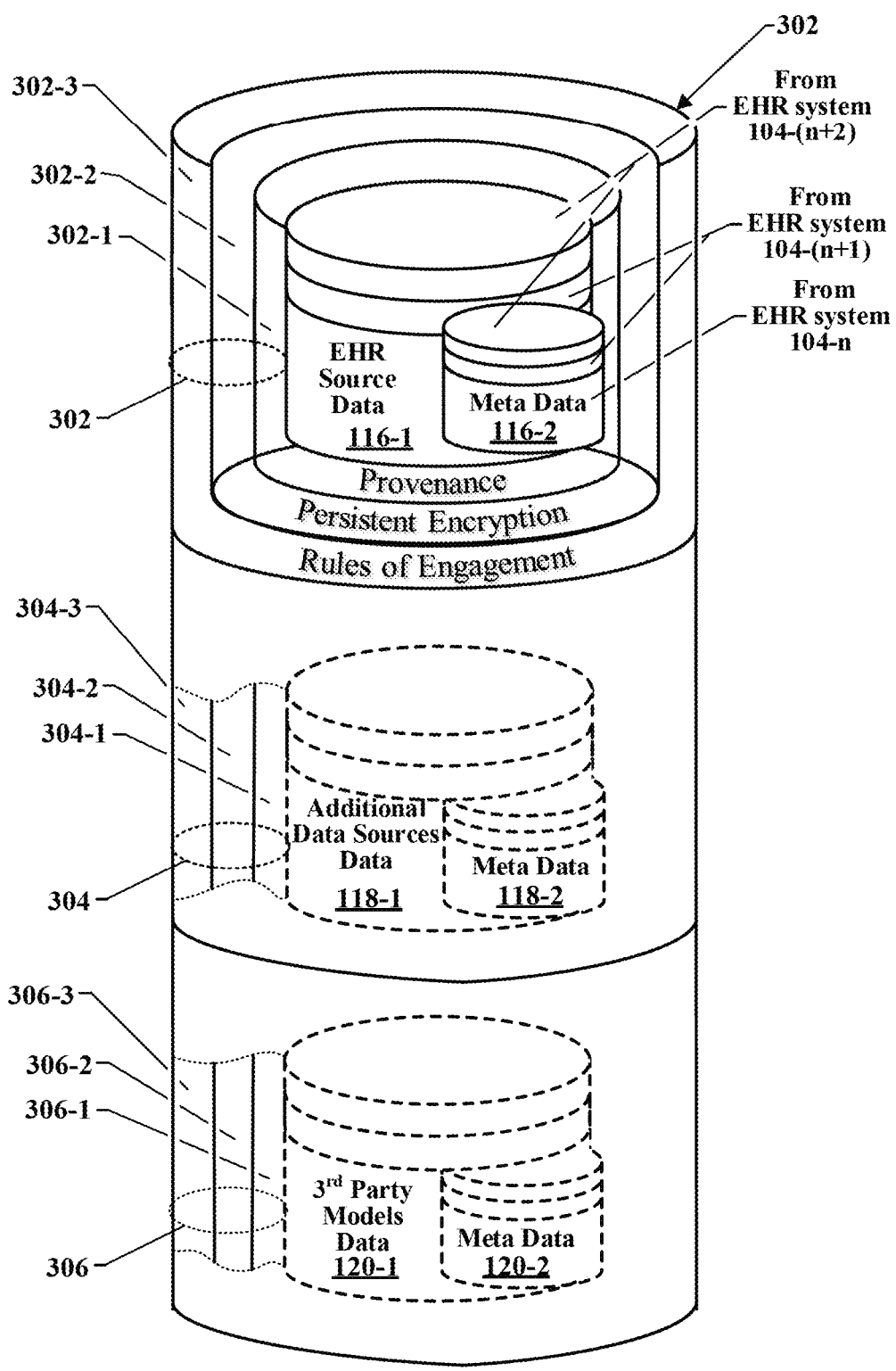
FIG. 3 is a functional block diagram of an example implementation of the combined staging database block in the FIG. 1 system and other systems and methods for artificial intelligence enhanced medical record exchange and common platform collaboration based medical and public health situation assessment, and health services resource and response management, in accordance with one or more embodiments.

FIG. 3 shows a logic schematic of a combined staging database 300, which can be an example implementation of the FIG. 1 system 100 combined staging database 114. In an embodiment, the combined staging database 300 can be configured to store the GTR EHR system sourced ePHI data 116-1 and GTR EHR metadata 116-2 in a sovereignty protective wrap, and to configure the sovereignty protective wrap based at least in part on the EHR system SP specification data 116-3. For purposes of description, recitation hereinafter of "sovereignty protective" will be alternatively use the following abbreviated form: "SP." It will be understood that "SP" as used herein is a coined letter string that serves only as a reduced letter count representation of the word sequence "sovereignty protective," and in the context of this disclosure does not possess, import, or apply any intrinsic meaning.

Systems for AI-enhanced health service resource and response management in accordance with various embodiments, such as but not limited to system 100 can, based in part on SP wrap configurations and SP wrapping processes disclosed herein, maintain rules of engagement with, protect sovereignty of and protect against unauthorized access to GTR EHR system sourced ePHI data 116-1 and GTR EHR metadata 116-2. In an embodiment, the combined staging database 300 can generate or form SP wrapping with a multilayer configuration. An example multilayer SP wrapping configuration can comprise a three-layer wrapping such as the example three-layer configuration of the EHR information SP wrapping 302. As shown in FIG. 3, the three-layer configuration of the EHR information SP wrapping 302 includes an EHR source-specific provenance layer 302-1, EHR source-specific persistent encryption layer 302-2, and EHR source-specific rules of engagement layer 302-3.

In an embodiment, the combined staging database 300 can also store the generic transformed additional source health data 118-1 and the generic transformed additional source metadata 118-2, collectively referenced for purposes of description as "additional source generic transformed information," with additional source information SP wrapping 304. Purposes and functions of the additional source information SP wrapping 304 can be, for example. as described above for the EHR information SP wrapping 302 for the GTR EHR system sourced ePHI data 116-1 and GTR EHR metadata 116-2, i.e., maintaining rules of engagement with, protecting sovereignty of, and protecting against unauthorized access to generic transformed additional source health data 118-1 and generic transformed additional source metadata 118-2. In an embodiment, configuration of additional source information SP wrapping 304 can be based at least in part on the additional source SP specification data 118-3. In an embodiment, the additional source sovereignty protective wrap can be, but is not necessarily, a multilayer wrap configuration such as the examples of additional source information SP wrapping 304 visible in FIG. 3. The example comprises an additional source provenance layer 304-1, additional source persistent encryption layer 304-2, and additional source rules of engagement layer 304-3.

With continuing reference to FIG. 3, in an embodiment the combined staging database 300 can store the generic transformed third-party supplier model data 120-1 and generic transformed third-party supplier metadata 120-2, collectively referenced for purposes of description as "third-party model information," with third-party model information SP wrapping 306. Purposes and functions of the third-party supplier model information SP wrapping 306 can be, for example. as described above for the EHR information SP wrapping 302 for the GTR EHR system sourced ePHI data 116-1 and GTR EHR metadata 116-2, i.e., maintaining rules of engagement with, protecting sovereignty of, and protecting against unauthorized access to third-party model information. In an embodiment, third-party supplier model information SP wrapping 306 can be based at least in part on the third-party supplier SP specification data 120-3. In an embodiment, the third-party supplier model information SP wrapping 306 can be, but is not necessarily, a multilayer wrap configuration such as the examples of third-party supplier model information SP wrapping 306 visible in FIG. 3. The example comprises a third-party supplier provenance layer 306-1, third-party supper persistent encryption layer 306-2, and third-party supper rules of engagement layer 306-3.

It will be understood that "three-layer" as used herein, in the context of sovereignty protective wrap, can be a logic representation that is not necessarily limiting as to any sequencing or ordering of operation. It will also be understood that certain sovereignty protective wrap(s) for the GTR EHR system sourced ePHI data 116-1 and GTR EHR metadata 116-2 are not necessarily configured identically to the sovereignty protective wrap(s) for the generic transformed additional source health data 118-1 and generic transformed additional source metadata 118-2, or to the sovereignty protective wrap(s) for the generic transformed third-party supplier model data 120-1 and generic transformed third-party supplier metadata 120-2. It will be further understood that new ownership with additional data sovereignty rules can accrue during data transformational processes 124, and that that logic 112 can be iteratively reapplied based on feedback from logic 124 to create nested accrual, ownership and sovereignty rules as value of the information content is added during data modeling.

Figure 4:
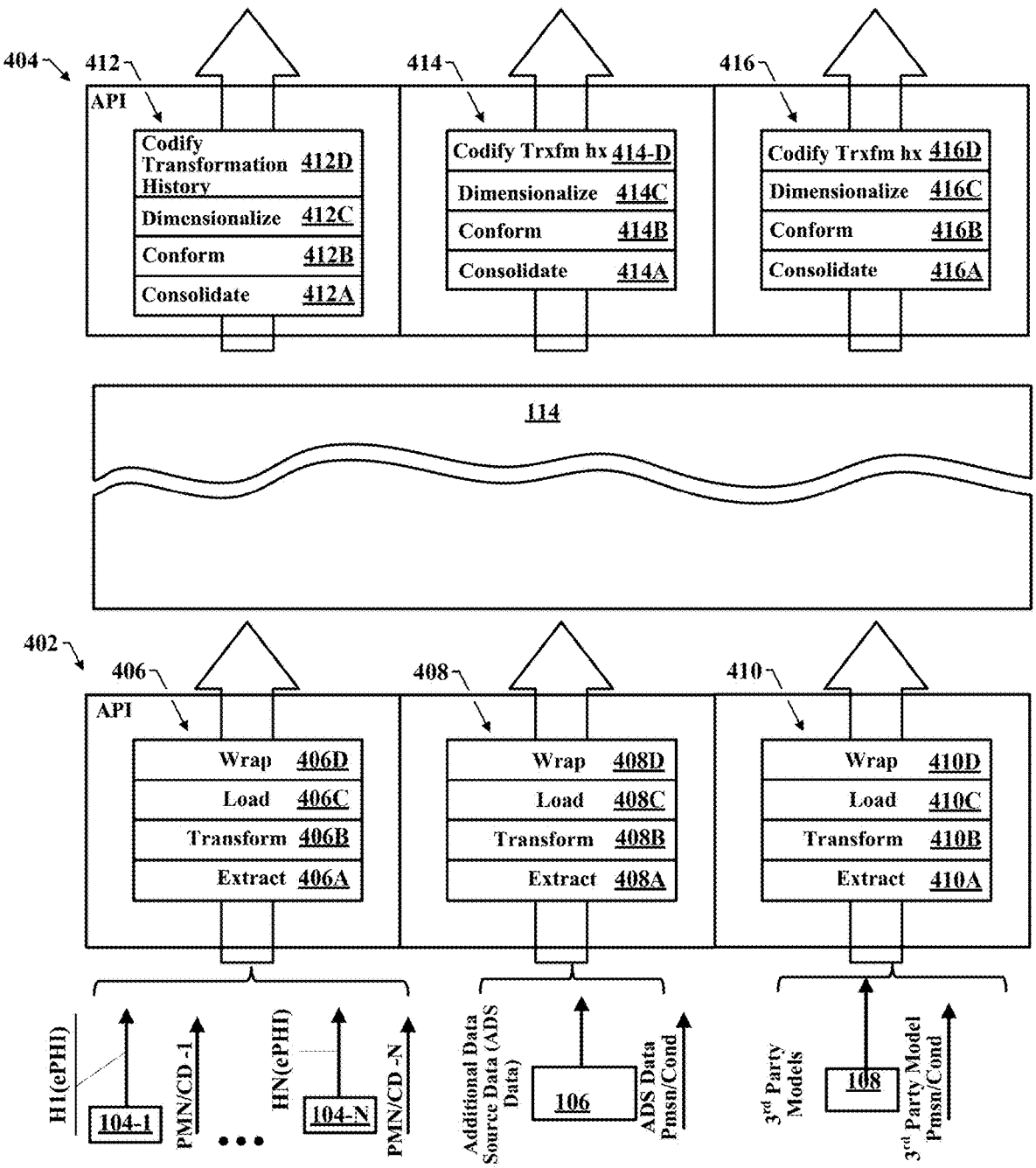
FIG. 4 is a logic flow diagram of an example process in sovereignty protective transferring of data into and out from the combined staging database of the FIG. 1 system, for various systems and methods for artificial intelligence enhanced medical record exchange, medical and public health situation assessment and health service resource and response management, in accordance with one or more embodiments.

FIG. 4 is a process flow diagram illustrating a flow 400 of a computerized process, in accordance with various embodiments, for performing SP transferring of data from the above-described external data sources, i.e., the EHR systems 104, additional sources 106, and third-party model suppliers 108, into and out from the combined staging database 114. Example features and operations of the flow 400 will be described in reference to the FIG. 1 system 100. This is to assist in focusing description of the flow 400 on features of the process. It is not intended to limit practices of the flow 400 to the FIG. 1 system 100. In an embodiment, features of the flow 400 can include computerized information extracting and data sovereignty wrapping 402, and features thereof include loading into the combined staging database 114 appropriately SP wrapped generic transformations of information content of data received from the above-described external data sources. The computerized information extracting and data sovereignty wrapping 402 can be performed, for example, by the IE-DSW logic 112. Implementations of the IE-DSW logic 112 include, but are not limited to, a general purpose programmable computer that includes a processor coupled to a tangible, non-transitory storage medium that stores or embodies computer-executable instructions that, when executable by the processor, cause the processor to perform in accordance with the described computerized information extracting and data sovereignty wrapping 402. Example implementations of the general purpose programmable computer are described in more detail later in this disclosure, for example, in reference to FIG. 20.

Features of the flow 400 can also include computerized transforming and concept aligning 404, and features thereof include aligning of related concept information and transformation of such information to an interoperable form for use, for example, by collaborative analysis resources and processes hosted by the virtual data warehouse and collaboration platform 128, as described in more detail in later paragraphs. The computerized transforming and concept aligning 404 can be performed, for example, by the transform and concept alignment logic 124. Implementations of the transform and concept alignment logic 124 can include, but are not limited to, a general purpose programmable computer, such as described above for implementation of the IE-DSW logic 112.

Referring to FIG. 4, in an embodiment, information extracting and data sovereignty wrapping 402 can include a first branch IE-DSW processing 406, which can be for EHR system sourced ePHI data received from EHR systems 104, a second branch IE-DSW processing 408, which can be for additional source data received from additional sources 106, and can include a third branch IE-DSW processing 410, e.g., for third-party supplier model data received from third-party model suppliers 108. For purposes of describing embodiments and example features and operations thereof, the first branch IE-DSW processing 406 will be alternatively referenced as the "EHR source IE-DSW processing" 406, the second branch IE-DSW processing 408 will be alternatively referenced as the "additional source IE-DSW processing" 408, and the third branch IE-DSW processing 410 will be alternatively referenced as the "third-party source IE-DSW processing" 410.

FIG. 4 illustrates a data lake 114 where a large volume of data has been cleaned and staged, ready for analysis, but the data are still largely in their original form and maintain much of their original architecture. The data is in the same platform, some basic translations may have been made (e.g. true NULLs for a database that used "N/A"s), and security features may have been attached. With the data in the same platform, the data modeler 1A can process the next step. The data modeler 1A may align like concepts that are available from within the records to generate a model. In some cases, a model may be an integrated phenotype reference model ("IPRM") (1220 on FIG. 12B).

As stated above, description of features and operations in the EHR source IE-DSW processing 406 assumes EHR system sourced data that can include ePHI data and EHR metadata. Regarding EHR source SP specifications, in accordance with various embodiments the flow 400 can receive these specifications via EHR system 104 sourced data. Such embodiments can include EHR system SP specification data that carries the SP specifications in their entirety. In other embodiments, the EHR system SP specification data may include an identifier of or a reference to EHR source SP specifications that may be stored, for example, by a memory resource that can be coupled to or otherwise accessible to computer resources performing the EHR source IE-DSW processing 406, e.g., the above-described general purpose computer implementation of the IE-DSW logic 112. These are only examples of providing the flow 400 EHR source SP specification information, additional source SP specification information, and third-party source SP specification information to the flow 400, and are not intended as a limitation on the scope of practices in accordance with disclosed embodiments.

In an embodiment, implementations for providing additional source SP specifications from the additional sources 106 to the additional source IE-DSW processing 408, or providing third-party source SP specifications from the third-party model suppliers 108 to the third-party model source IE-DSW processing 410 can include, for example, implementations as described above for providing EHR source SP specifications to the EHR source IE-DSW processing 406.

Referring to FIG. 4, in an embodiment, the EHR source IE-DSW processing 406 can include, in response to receiving ePHI data from EHR systems 104, a first branch information extracting 406A, which extracts ePHI content and EHR metadata from the EHR system sourced ePHI data. In an embodiment, following, merged with, or otherwise associated with the first branch information extracting 406A (hereinafter collectively encompassed by "associated with," where explicitly stated or made clear from its context to mean otherwise) can be a first branch transforming 406B. Features of the first branch transforming 406B can include transforming the extracted information content of the PHI data and EHR system metadata to GTR EHR system sourced ePHI data 116-1 and GTR EHR metadata 116-2. In an embodiment, EHR source IE-DSW processing 406 can also include, associated with the first branch transforming 406B, a first branch loading 406C, and features thereof can include loading the generic ePHI and generic EHR sourced metadata into, respectively, a generic ePHI template and generic EHR metadata template. In one or more embodiments, the EHR source IE-DSW processing 406 can also include, for example, associated with the first branch loading 406C, a first branch source-specific SP wrapping 406D the template loaded generic ePHI and generic EHR sourced metadata with an SP wrapping that complies with the EHR sovereignty specification, e.g., as defined by or referenced by EHR system SP specification data 116-3 included with the EHR system sourced ePHI data In an embodiment, operations in the first branch source-specific SP wrapping 406D can include storing the SP wrapped generic ePHI and generic EHR sourced metadata in the combined staging database 114 in accordance with the SP wrapping.

In an embodiment, additional source IE-DSW processing 408 can be in response to receiving additional health data from additional sources 106, and can include a second branch information extracting 408A and, for example, associated with the second branch information extracting 408A, a second branch transforming 408B. In an embodiment, for example, associated with the second branch transforming 408B, can be a second branch template loading 408C and, associated therewith can be a second branch source-specific SP wrapping 408D. The second branch information extracting 408A can include, for example, extracting health information content from the additional source health data The second branch transforming 408B can include, for example, transforming the extracted additional source information and extracted metadata into, respectively, generic transformed additional source health data 118-1 information and generic transformed additional source metadata 118-2. Features of the second branch template loading 408C can include loading the generic transformed additional source health data 118-1 into a second branch additional source generic data template and loading the generic transformed additional source metadata 118-2 into an additional source generic metadata template. In an embodiment, second branch source-specific SP wrapping 408D can include wrapping the template loaded form of the generic transformed additional source health data 118-1 and template loaded form of the generic transformed additional source metadata 118-2 with an SP wrapping that complies with additional source sovereignty specification, e.g., additional source SP specification data 118-3.

In an embodiment, third-party model source IE-DSW processing 410 can include, in response to receiving the third-party source model data from third-party model suppliers 108, a third branch information extracting 410A, and associated therewith can be a third branch transforming 410B. Associated with the third branch transforming 410B can be third branch template loading 410C, and associated therewith can be a third branch SP wrapping 410D. The third branch information extracting 410A can include, for example, extracting information content from third-party supplier model data from the third-party model suppliers 108 and the third branch transforming 410B can include transforming the extracted model information to generic transformed third-party supplier model data 120-1 information and generic transformed third-party supplier metadata 120-2. The third branch template loading 410C can include loading the generic transformed third-party supplier model data 120-1 and generic transformed third-party supplier metadata 120-2 into a third branch template. The third branch SP wrapping 410D can include third-party supplier specific SP wrapping the third branch template loaded form of the generic transformed third-party supplier model data 120-1 and generic transformed third branch template loaded form of the generic transformed third-party supplier metadata 120-2 with an SP wrapping that complies with third-party supplier sovereignty protective specification, e.g., 120-3.

Referring to FIG. 4, in an embodiment, features of the transform and concept aligning 404 can include alignment of related concept information and transformation of such information to an interoperable representation. As will be understood by persons of ordinary skill upon reading this disclosure and practicing its various embodiments, the alignment includes specific alignments to knowledge representation schemata, and to analysis algorithm structures supported by the virtual data warehouse and collaboration platform 128. For example in processes in accordance with the present disclosure, process flow, operations therein, and other features that are in, or that support "transformation of such information to an interoperable representation" can include but are not limited to: formal ontologies, e.g., OWL and NIEM, interoperable representation" can include but are not limited to: formal ontologies, e.g., OWL and NIEM. Tools that can be applied by the transform and concept alignment logic 124 can include non-ontological knowledge representations, e.g., an integrated phenotype reference model and other knowledge representation schemata. Tools that can be applied by the transform and concept alignment logic 124 include standardized vocabularies, e.g., SNOMED, data dictionaries, AI tools such as neural nets trained for phenotyping and other analyses by ML and deep learning, and data dictionaries. As also described in more detail in later sections of this disclosure, the above-listed example tools, applied by or through methods and systems in accordance with this disclosure, can provide, among other features, dimensional conformity and alignment of related concepts in a manner enabling efficient multi-participant collaborative, multi-layer analyses of multi-sourced health related information.

The transform and concept aligning 404 can be described as including a first branch transform and concept alignment processing 412, e.g., for receiving, extracting information content and performing particular processing of EHR system-sourced data, including SP wrapping information content in accordance with EHR system SP specifications, such as ePHI and other data from the EHR systems 104, a second branch transform and concept alignment processing 414, e.g., for additional source data, such as health-related information from the additional sources 106, and a third branch transform and concept alignment processing 416, e.g., for third-party models 108.

As shown by the FIG. 4 example implementation, first branch transform and concept alignment processing 412 can include first branch consolidating 412A, first branch conforming 412B, first branch dimensionalizing 412C, and first branch codification of the total arc of EHR system-sourced data transformations 412D (labeled "Codify Trxfm hx" in block 412D on FIG. 4).

Second branch transform and concept alignment processing 414 can include second branch consolidating 414A, second branch conforming 414B, second branch dimensionalizing 414C, and second branch codification of the total arc of additional source data transformations 414D (labeled "Codify Trxfm hx" in block 414D on FIG. 4).

Third branch transform and concept alignment processing 416 can include third branch consolidating 416A, third branch conforming 416B, third branch dimensionalizing 416C, and third branch codification of the total arc of third-party model source data transformations 416D (labeled "Codify Trxfm hx" in block 416D on FIG. 4).

Figure 5:
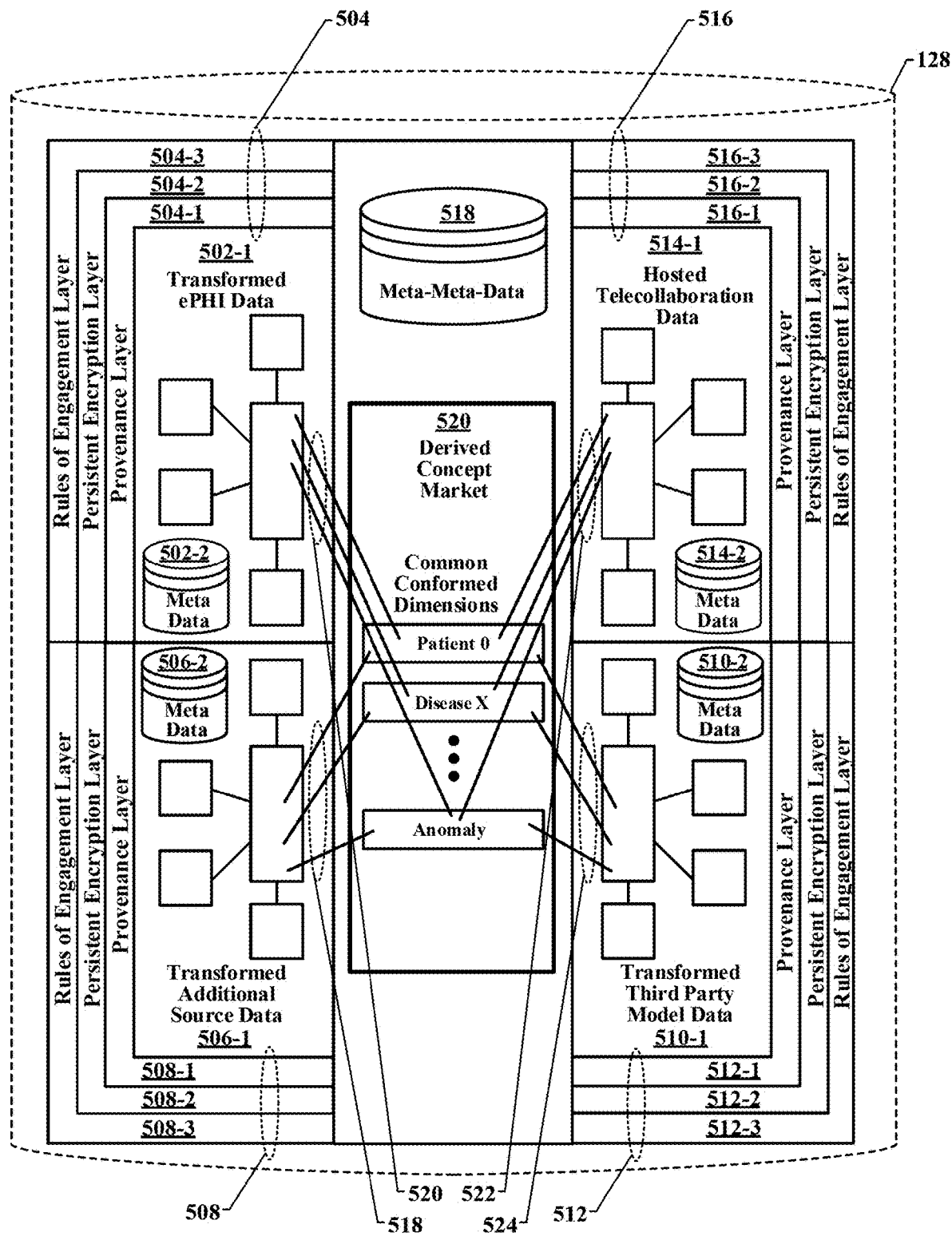
FIG. 5 is function block diagram of an example implementation of a virtual data warehouse and collaboration platform function block for the FIG. 1 system and various other systems and methods for artificial intelligence enhanced medical record exchange and common platform collaboration based medical and public health situation assessment, and health services resource and response management, in accordance with one or more embodiments.

FIG. 5 is a functional block diagram of an example of an implementation 500 of a virtual data warehouse and collaboration platform 128 for the FIG. 1 system 100 and for various other systems and methods for artificial intelligence enhanced medical record exchange and common platform collaboration based medical and public health situation assessment, and health services resource and response management, in accordance with one or more embodiments. For purposes of description, the implementation 500 of the virtual data warehouse and collaboration platform 128 will be alternatively referenced as "VDW-CP 500." As used herein, "VDW-CP" is a coined, alternative form for reciting "virtual data warehouse and collaboration platform," having no intrinsic meaning. It will be understood that, as used in this disclosure, "VDW-CP" is an arbitrary coined letter string that serves only as a reduced letter count representation of the word sequence "virtual data warehouse and collaboration platform" and, as used herein, does not have, import or carry any intrinsic meaning.

In an embodiment, VDW-CP 500 can store transformed ePHI information 502-1 and transformed EHT metadata 502-2 within a first VDW-CP transformed SP wrapper 504. The first VDW-CP transformed SP wrapper 504 can include a first VDW-CP transformed SP provenance layer 504-1, a first VDW-CP transformed SP persistent encryption layer 504-2, and a first VDW-CP transformed SP rules of engagement layer 504-3. In an embodiment, the VDW-CP 500 can construct the first VDW-CP transformed SP wrapper 504 based at least in part on the EHR information SP wrapping 302, or on EHR source SP specification data, e.g., EHR system SP specification data 116-3 on which, as described above in reference to FIG. 3, the EHR information SP wrapping 302 may be based.

In an embodiment, the VDW-CP 500 can store transformed additional source information 506-1 and transformed additional source metadata 506-2, within a second VDW-CP transformed SP wrapper 508. The second VDW-CP transformed SP wrapper 508 can include a second VDW-CP transformed SP provenance layer 508-1, a second VDW-SP transformed SP persistent encryption layer 508-2, and a second VDW-CP transformed SP rules of engagement layer 508-3. In an embodiment, the VDW-CP 500 can construct the second VDW-CP transformed SP wrapper 508 based at least in part on additional source information SP wrapping 304 or on additional source SP specification information, received from third-party model suppliers 108, on which additional source information SP wrapping 304 can be based. In an embodiment, the VDW-CP 500 can store transformed third-party source model information 510-1 and transformed third-party source metadata 510-2 within a third VDW-CP transformed SP wrapper 512. The third VDW-CP transformed SP wrapper 512 can include a third VDW-CP transformed SP provenance layer 512-1, a third VDW-CP transformed SP persistent encryption layer 512-2, and a third VDW-CP transformed SP rules of engagement layer 512-3. In an embodiment, the VDW-CP 500 can construct the third VDW-CP transformed SP wrapper 512 based at least in part on third-party supplier model information SP wrapping 306, or third-party source SP specification data, e.g., third-party supplier SP specification data 120-3 on which the third-party supplier model information SP wrapping 306 can be based.

Referring to FIG. 5, the VDW-CP 500 can store hosted telecollaboration data 514-1 and hosted telecollaboration metadata 514-2, within a VDW-CP telecollaboration SP wrapper 516. The VDW-CP telecollaboration SP wrapper 516 can include a VDW-CP telecollaboration SP provenance layer 516-1, a VDW-CP telecollaboration SP persistent encryption layer 516-2, and a VDW-CP telecollaboration SP rules of engagement layer 516-3. In an embodiment, the VDW-CP 500 can construct the VDW-CP telecollaboration SP wrapper 516 based at least in part on external sources' SP specification data that was received by and used by the FIG. 4 information extracting and data sovereignty wrapping 402 for performing the appropriate SP wrapping.

In an embodiment, the "based at least in part on," can include, for example, direct use of the external sources' SP specification data, e.g., for generating the EHR system SP specification data 116-3, additional source SP specification data used for generating additional source SP specification data 118-3, and third-party supplier SP specification information for generating third-party supplier SP specification data 120-3, or portions thereof. In an embodiment, "based at least in part on" can include indirect use of the external sources' specification data, for example, using information regarding the EHR information SP wrapping 302, the additional source information SP wrapping 304, or the third-party supplier model information SP wrapping 306, or any combination or sub-combination thereof. In an embodiment, such information regarding the EHR information SP wrapping 302, additional source information SP wrapping 304, or third-party supplier model information SP wrapping 306 can be provided to the computerized transforming and concept aligning 404, for example, via the virtual data warehouse and collaboration platform 128.

In an embodiment, construction of the VDW-CP telecollaboration SP wrapper 516 can be further based at least in part on the SP specification data provided by various among the external sources, e.g., to the data curation 110. In one or more embodiments, provided can include, but are not limited to, consistency and reliability in forming the VDW-CP telecollaboration SP wrapper 516 with a configuration that can maintain sovereignty protection, throughout the various multi-participant analyses supported on the virtual data warehouse and collaboration platform 128.

FIG. 5 shows the virtual data warehouse and collaboration platform 128 supporting a meta-meta-data 518, which can be information about the metadata. As an illustrative example of a meta-meta-data 518, assume that metadata associated with a first EHR record includes a medical concept identified from the content of the first record and listed in the derived concept market with a specified degree of certainty; assume further that metadata associated with a second EHR record includes a medical concept identified from the content of the second record and listed in the derived concept market with its own degree of certainty. An example of meta-meta-data 518 can be information regarding the degree of certainty that the two concepts from EHR first record and EHR second record represent the same medical concept.

FIG. 5 also shows a derived concept market 520 and storage, e.g., on the virtual data warehouse and collaboration platform 128, an indication of a Patient 0, of a Disease X, and an Anomaly as indications of common conformed dimensions. Patient 0, Disease X, and Anomaly are teaching examples of common conformed dimensions that may be contained within the derived concept market 520. Lines are shown on FIG. 5, attaching each concept to each of the individual data marts 502-1, 506-1, 510-1, and 514-1. One cluster 522 of the lines represents an example state of the bridge shown on FIG. 1 between the transformed component data and the common conformed dimensions within the derived concept market 520. Another cluster 524 of the lines represents an example state of the bridge on FIG. 1 between the transformed additional source data and the common conformed dimensions in the derived concept market 520. Another cluster 526 represents an example state of the FIG. 1 bridge between the transformed hosted telecollaboration data and the common conformed dimensions in the derived concept market 520, and another cluster 528 represents an example state of the FIG. 1 bridge between the transformed third party models and the common conformed dimensions in the derived concept market 520.

Figure 6:
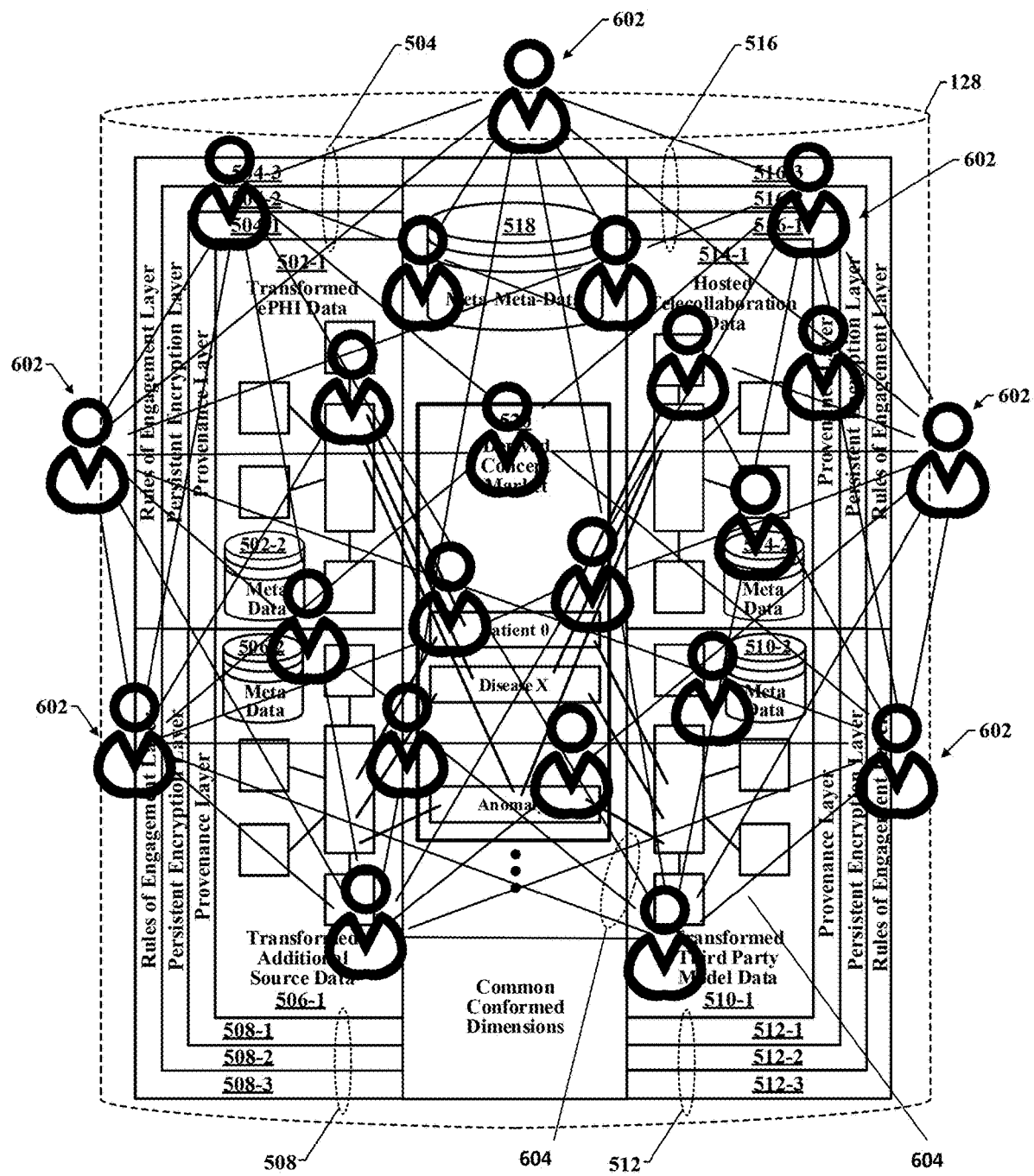
FIG. 6 shows by graphic overlay on FIG. 5 an example general configuration of a multi-participant telecollaboration that can be hosted on a common platform aspect of systems and methods for artificial intelligence enhanced medical record exchange and common platform collaboration based medical and public health situation assessment, and health services resource and response management in accordance with one or more embodiments.

FIG. 6 shows by graphic overlay on FIG. 5 one example general configuration of a multi-participant telecollaboration as can be hosted on the virtual data warehouse and collaboration platform 128 of FIG. 1 of systems and methods for artificial intelligence enhanced medical record exchange and common platform collaboration based medical and public health situation assessment, and health services resource and response management in accordance with one or more embodiments. The general configuration includes a visible plurality of participants 602, interconnected by communication links 604. The participants 602 can be individuals, can be business entities, academic institutions, or government agencies. The communication links 604 can represent extant communications, communication resources, agreements for periodic communication, agreements for "as needed" communication between multiple participants 602. The FIG. 6 quantity or population of graphical images labeled "602" is based in part on drafting considerations, and is not intended as any statement of preference or limitation on practices according to disclosed embodiments.

FIG. 7 shows a logic schematic of a specific software development kit (SDK) 700 implementation of the system 100 SDK 132, configured to enable, through novel features and novel combinations of such features with features of system 100, multi-contributor maintenance coupled with evolution of a multi-tool suite of analysis apps. The multi-contributor maintenance and coupled evolution provides a robust multi-tool suite of analysis apps. The multi-tool suite of analysis apps can, in turn, provide AI enhanced multi-tool analysis resource for coupling to a multi-institutional knowledge database, for the FIG. 1 system and various other systems and methods for AI enhanced medical record exchange and common platform collaboration based medical and public health situation assessment, and health services resource and response management in accordance with one or more embodiments.

The FIG. 7 SDK 700 implementation includes natural language processing (NLP) and text analytics tools 702A; statistical analysis tools 702B; Graphical User Interface (GUI) and Data Visualization (Data Viz) tools 702C; relation and collaboration tools 702D; geospatial tools 702E; AI, machine learning (ML), and deep learning (DL) modeling tools 702F; policy operationalization tools 702G; gaming scenario tools 702H; query engine(s) 702I; project and task management tools 702J; import and export tools 702K; and data integrity and security tools 702L. The above-listed example plurality of SDK tools will be collectively referenced as "FIG. 7 SDK tool suite 700." It will be understood that the SDK tool suite 700 is an example, not a limitation of what can be many different SDK tool suites that may be used in practices according to disclosed embodiments, and the appended claims. Regarding aspects of differences of the different SDK tool suites, examples include difference with respect to the number of different analytics tools, and different combinations of the tools, and respective configurations of the tools.

It will be understood that allocation and arrangement of hardware, software, and combination hardware-software resources in implementations of the SDK tool suite 700 are not necessarily grouped, segmented, or partitioned in accordance with above-listed individual analytic tools. Further, implementations of various of the analytics tools can include functionalities overlapping functionalities of other of the analytics tools. As an illustrative, non-limiting example, various implementation of the gaming scenario tools 702K can include functionalities of, or can be constructed or evaluated, or both, using ML and other AI tools.

FIG. 8 shows a logic schematic of an example of a configuration 800 of a curated applications resource that can be provided, for example, by the app market 134 of the FIG. 1 system 100. The configuration 800 shows examples of third party and user contributed applications for the FIG. 1 system and for various other systems and methods for AI enhanced medical record exchange and common platform collaboration based medical and public health situation assessment, and health services resource and response management in accordance with one or more embodiments. The groupings of the applications into app market first applications regions 802 and app market second applications regions 804 are for logistics of figure labeling, and are not intended to convey any grouping as to functionality, configuration, or features.

FIG. 9 shows a logic schematic of an example configuration 900 of the GUI 136 of the FIG. 1 system 100, with illustrative examples of widget GUI regions 902-1, 902-2, . . . 902-R (collectively "GUI first widget regions 902"), "R" being any integer and widget GUI regions 904-1, 904-2, . . . , 904-S (collectively "GUI second widget regions 904"), "S" being any integer. The groupings of the widget regions into GUI first widget regions 902 and GUI second widget regions 904 are for logistics of figure labeling, and are not intended to convey any grouping as to functionality, configuration, or features. Widgets associated with the GUI first widget regions 902 and GUI second widget regions 904 can be for system 100 and for processes and methods supported by same, or by other systems or system configurations according to this disclosure, for AI enhanced medical record exchange and common platform collaboration based medical and public health situation assessment, and health services resource and response management in accordance with one or more embodiments.

Figure 10:
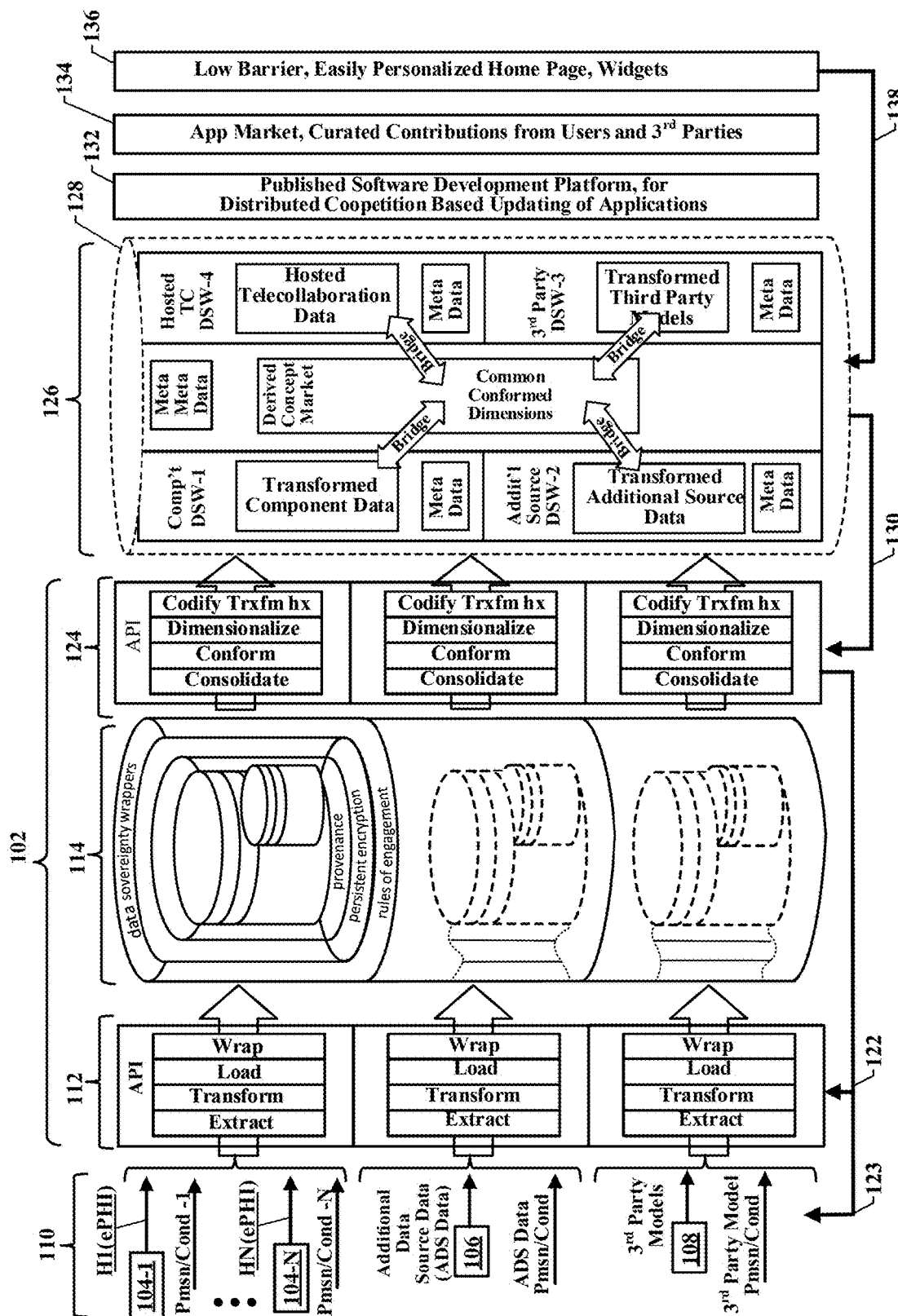
FIG. 10 is a functional block diagram of an example adaptation of the FIG. 1 system, showing incorporation of the staging database configuration of FIG. 3, and the FIG. 4 diagrammed flow of sovereignty protective transferring of data into and out from the combined staging database, for various systems and methods for AI enhanced medical record exchange and common platform collaboration based medical and public health situation assessment, and health services resource and response management in accordance with one or more embodiments.

FIG. 10 shows a function block schematic with certain logic details of an example adaptation of the FIG. 1 system, including the FIG. 3 configuration of the combined staging database 114 in accordance with FIG. 2 and with the FIG. 3 implementation of the sovereignty protective wrapping feature. FIG. 10 also shows the FIG. 4 flows of transferring of data into and out from the combined staging database. The FIG. 10 adaptation can provide an environment for various systems and methods for AI enhanced medical record exchange and common platform collaboration based medical and public health situation assessment, and health services resource and response management, in accordance with one or more embodiments.

Figure 11:
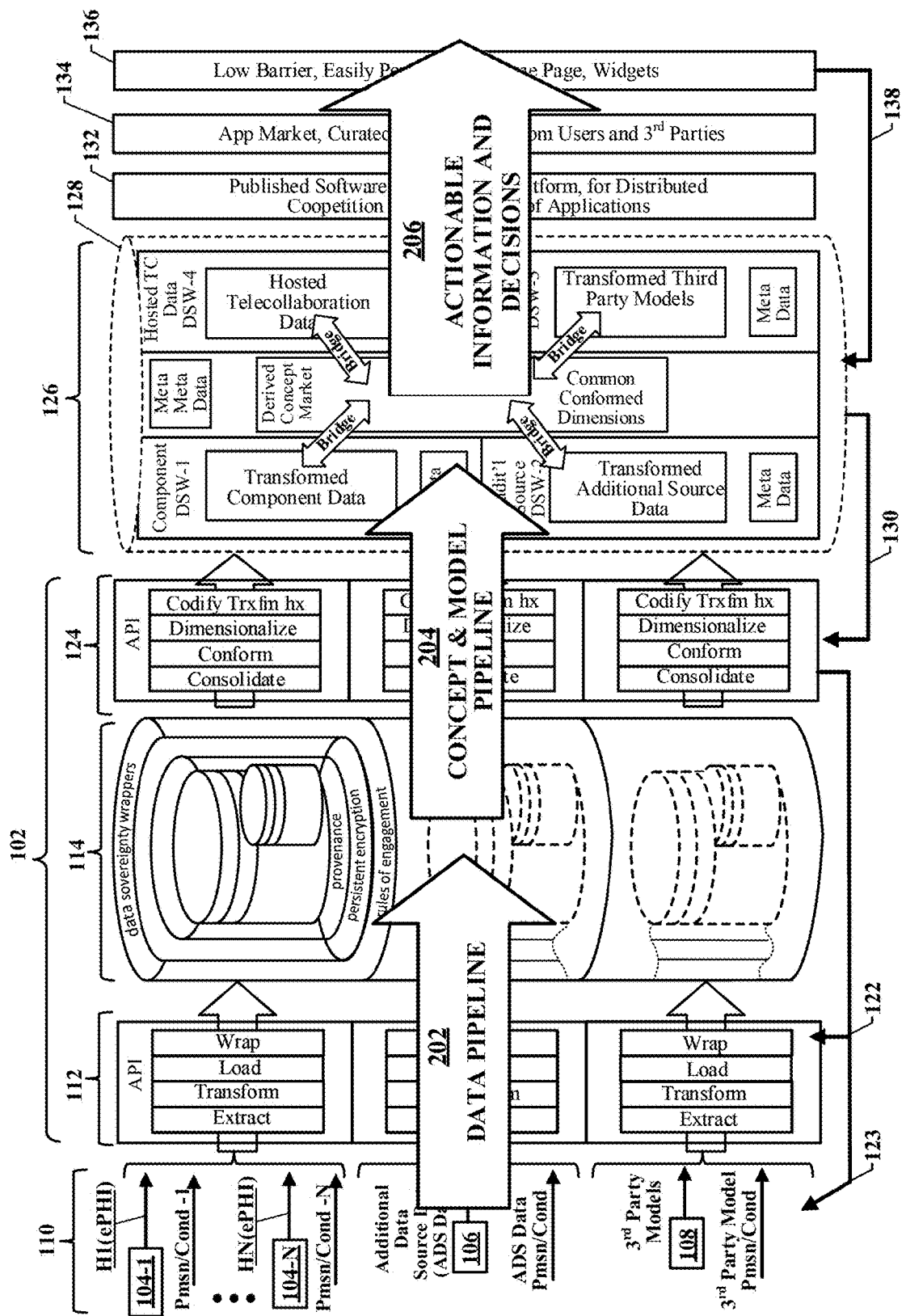
FIG. 11 shows, by graphic overlay of flow arrows on FIG. 10, data pipeline aspects and certain concept and model pipeline aspects, and flow of actionable information and decisions, for the FIG. 10 system and other systems and methods for artificial intelligence enhanced medical record exchange and common platform collaboration based medical and public health situation assessment, and health services resource and response management in accordance with one or more embodiments.

FIG. 11 shows a graphic overlay on FIG. 10 of FIG. 2 flow annotations for the data pipeline flow 202, concept and model pipeline flow 204, and actionable information and decision pipeline 206, representing the above-described features as provided by FIG. 10 system adaptation. Features of the FIG. 11 system can include, without limitation, sovereignty protective extraction, via, for example, and information extracting, sovereignty protective wrapping logic such as implemented by the IE-DSW logic 112. The IE-DSW logic 112 provides for receiving an EHR data, e.g., from one of the EHR system sources 104 and in response, wrapping, in an EHR system-specific sovereignty protective wrapper, a genericized form of a health-related information content of the EHR data. Such features are provided, for example, by the IE-DSW logic 112 functions, shown in FIG. 11 and described earlier in reference to FIG. 4, of first branch information extracting 406A, first branch transforming 406B, first branch loading 406C, and first branch source-specific wrapping 406D. The FIG. 11 combined staging database 114 provides a staging database, coupled to the information extracting, sovereignty protective wrapping logic, i.e., to the IE-DSW logic 112, and configured to store, in accordance with the EHR system-specific sovereignty protective wrapper, the genericized form of the health-related information content of the EHR data. The FIG. 11 system also includes the transform and concept alignment logic 124, coupled to the combined staging database 114, and configured to perform a transforming of and aligning of the genericized form of the health-related information to a transformed interoperable health-related data. Various features of the features of the transforming and aligning are described above, and such features and additional features are described in more detail in subsequent paragraphs, e.g., in reference to FIG. 18 and, regarding a further configuration, in reference to FIG. 21. In an embodiment, the FIG. 11 system also provides collaboration platform 128, which is coupled to the transform and concept alignment logic 124, and is configured to perform a hosting of a telecollaborative analysis of the transformed interoperable health-related data. Telecollaborative analysis can be provided by one or more of the participants, e.g., one or more of the participants 602 visible in FIG. 6. Features of the collaboration platform 128 can also include, provided for example, by the VDW-CP telecollaboration SP wrapper 516 described in detail in reference to FIG. 5, a wrapping, in a telecollaboration participant specific sovereignty protective wrapper, of a telecollaboration data associated with a telecollaboration participant. The collaboration platform 128 can also provide, as described in reference to FIG. 5, a maintaining during the telecollaborative analysis of the transformed interoperable health-related data, a sovereignty of the transformed interoperable health-related data in accordance with the EHR system-specific sovereignty protective wrapper, and a sovereignty of the telecollaboration data associated with the telecollaboration participant in accordance with the telecollaboration participant specific sovereignty protective wrapper.

Figure 12A:
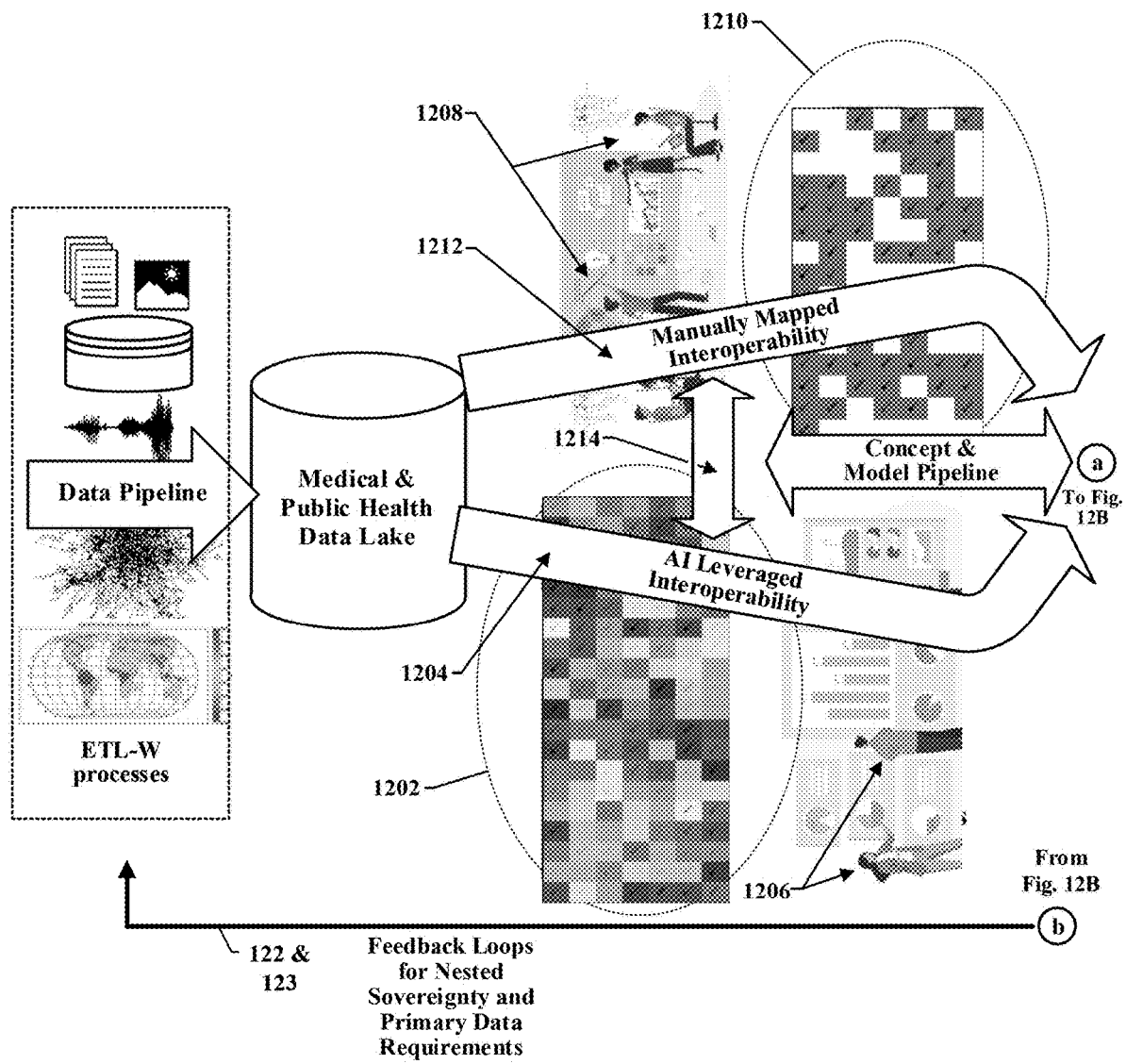
FIGS. 12A and 12B show a two-sheet arrangement of a functional block diagram and supported process flow diagram of another example system in accordance with one or more embodiments for AI enhanced medical record exchange and common platform collaboration based medical and public health situation assessment, and health services resource and response management in accordance with one or more embodiments.
Figure 12B:
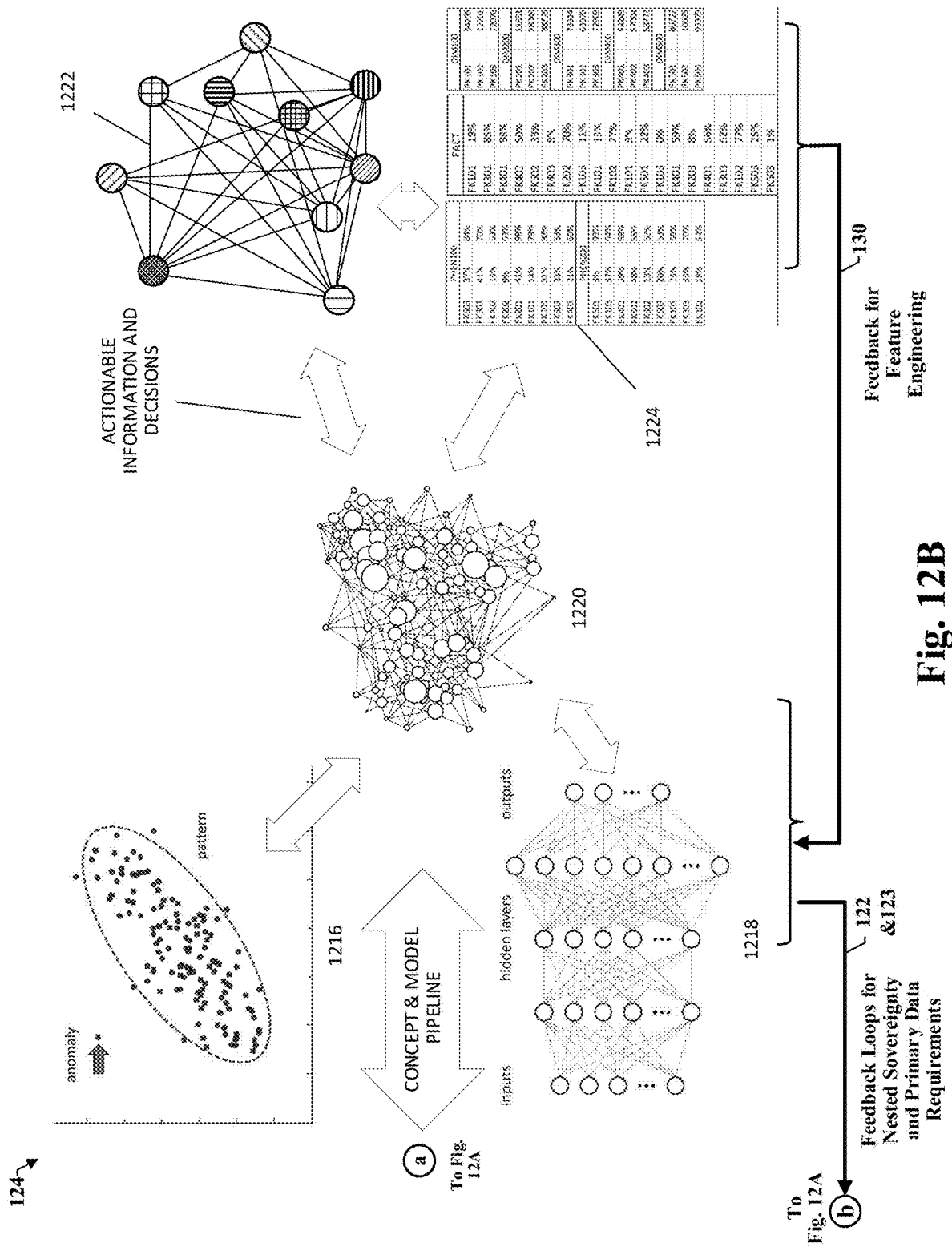

FIGS. 12A and 12B are a two-sheet arrangement of a functional block and supported process diagram of another example system in accordance with one or more embodiments for AI enhanced medical record exchange and common platform collaboration based medical and public health situation assessment, and health services resource and response management in accordance with one or more embodiments.

FIG. 12A and FIG. 12B, viewed together, are a graphical representation of logic operations and processes for which the transform and concept alignment logic 124 can be configured. A further of view of these processes is shown on FIG. 13A. Referring to FIG. 12A, in an embodiment, features can include an AI-computed interoperability mapping 1202, such as represented in table form in the figure It will be understood that the computed cells of the table representing the AI computed interoperability mapping produces probabilistic, not binary, dimensional conformity and alignment of related concepts, and therefore if the table were larger the cells could be filled by a shading having respective cell-specific degree of grey. In an embodiment, the AI-computed interoperability mapping 1202 can provide an AI-leveraged interoperability path 1204. In an embodiment, a validation, such as manual validation may be utilized, as represented by persons 1206 on the AI-leveraged interoperability path 1204. Manual validation may not be essential, but can be used, e.g., to have the "human-in-the loop."

In an embodiment, manual mapping of interoperability, such as represented on the figure by individuals 1208, can generate a manual interoperability map 1210, such as represented on the figure by another table. The manual interoperability map 1210 can provide a manually mapped interoperability path 1212. In accordance with one or more embodiments, cross-support can be provided, by exchanging 1214 of information between the AI-leveraged interoperability path 1204 and the manually mapped interoperability path 1212.

Referring to FIG. 12B, the data plot 1216 represents secondary analytics that, together with the AI neural network 1218, can support the integrated phenotype reference model 1220, and can directly provide output to the collaborative network 1222.

FIGS. 12A and 12B show example of features of analytics and artificial intelligence. Example features of analytics can include, but are not limited to, traditional statistical analysis, and example aspects of AI can include machine learning techniques in which executable code can dynamically alter behavior based on information from monitoring and sensing resources. FIGS. 12A and 12B fit into the 124 column of FIG. 13A. FIGS. 12A and 12B are a pictorial representation of 124, and show in much more detail how the processes listed in 124 are accomplished.

Figure 13A:
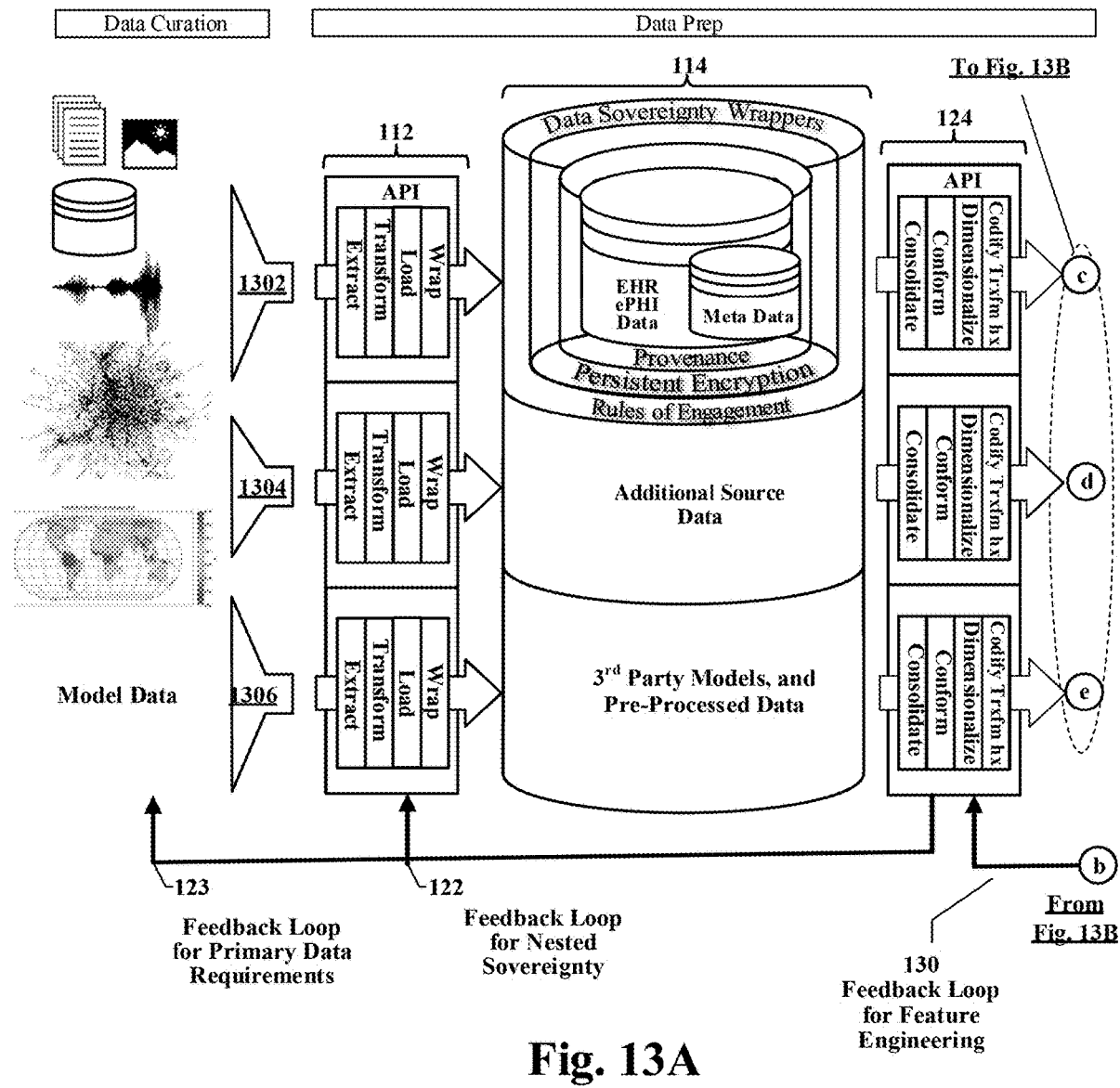
FIGS. 13A and 13B show a two-sheet arrangement of a functional block diagram and supported process flow diagram showing aspects of an example system in general accordance with the FIG. 10 system for medical and public health service resource and response management via AI enhanced medical record exchange, feeding concept generation and dynamic updating of multi-institutional knowledge database coupled to AI enhanced multi-tool analysis resources in accordance with one or more embodiments.
Figure 13B:
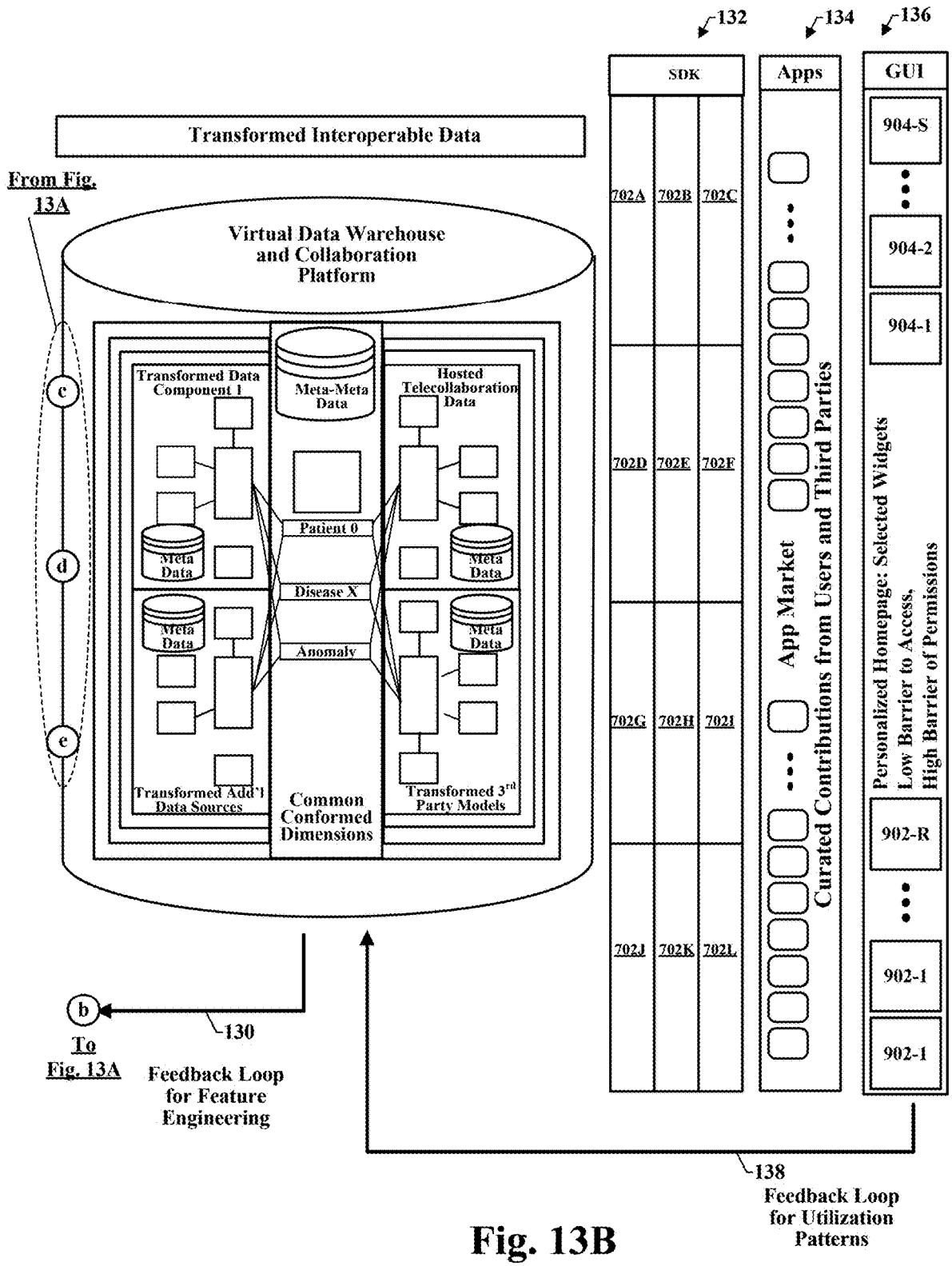

FIGS. 13A and 13B are a two-sheet arrangement of functional block and associated process diagram showing aspects of an example system in general accordance with the FIG. 10 system for medical and public health service resource and response management via AI enhanced medical record exchange feeding concept generation and dynamic updating of multi-institutional knowledge database coupled to AI enhanced multi-tool analysis resources in accordance with one or more embodiments.

FIGS. 12A-B show examples of features of analytics and artificial intelligence. Example features of analytics can include, but are not limited to, traditional statistical analysis, and example aspects of AI can include machine learning techniques in which executable code can dynamically alter behavior based on information from monitoring and sensing resources. FIGS. 12A-B fit into the 124 column of 13A. FIGS. 12A and B are a pictorial representation of 124, and show in much more detail how the written processes listed in 124 are accomplished.

Below is element 1224 of FIG. 12B enlarged to show detail and improve readability of the text.

| PHEN100 | | |
|---|---|---|
| FK503 | 37% | 84% |
| FK301 | 41% | 70% |
| FK402 | 13% | 53% |
| FK202 | 9% | 63% |
| FK201 | 41% | 98% |
| FK101 | 14% | 79% |
| FK203 | 31% | 92% |
| FK303 | 33% | 53% |
| FK401 | 21% | 60% |
| PHEN200 | | |
| FK501 | 3% | 93% |
| FK103 | 37% | 64% |
| FK402 | 39% | 69% |

-continued

| | | |
|---|---|---|
| FK502 | 48% | 55% |
| FK302 | 13% | 52% |
| FK503 | 20% | 53% |
| FK101 | 23% | 59% |
| FK303 | 33% | 70% |
| FK102 | 18% | 54% |

| FACT | |
|---|---|
| FK101 | 19% |
| FK301 | 85% |
| FK401 | 98% |
| FK402 | 50% |
| FK502 | 33% |
| FK403 | 8% |
| FK202 | 70% |
| FK103 | 11% |
| FK101 | 13% |
| FK102 | 77% |
| FK101 | 3% |
| FK501 | 22% |
| FK103 | 0% |
| FK401 | 59% |
| FK203 | 8% |
| FK401 | 56% |
| FK303 | 52% |
| FK102 | 77% |
| FK503 | 25% |
| FK503 | 1% |
| DIM100 | |
| PK101 | 34295 |
| PK102 | 22701 |
| PK103 | 72076 |
| DIM200 | |
| PK201 | 11651 |
| PK202 | 26049 |
| PK203 | 98725 |
| DIM300 | |
| PK301 | 77314 |
| PK302 | 63976 |
| PK303 | 72909 |
| DIM400 | |
| PK401 | 44249 |
| PK402 | 57004 |
| PK403 | 53722 |
| DIM500 | |
| PK501 | 89727 |
| PK502 | 10925 |
| PK503 | 93379 |

Referring to FIG. 13A, each of the EHR data source 1302, additional parties data source 1304, and third party model data source 1306 can be piped through all the processes of the transform and concept alignment logic 124, and can emerge at jump points (c), (d), and (e), ready for the data warehouse 126. For purposes of description, the processes of the transform and concept alignment logic 124, which, in an embodiment, comprise consolidate, conform, dimensionalize, and codify may be collectively referred as "analytics and AI engine." In an embodiment, the emergence at jump points (c), (d), and (e), described above, can be considered as entry points, in a logic sense, into the large meta-database shown as the derived concept market 520 on FIG. 5, and as the derived market concept 1902 on FIG. 19.

Figure 14:
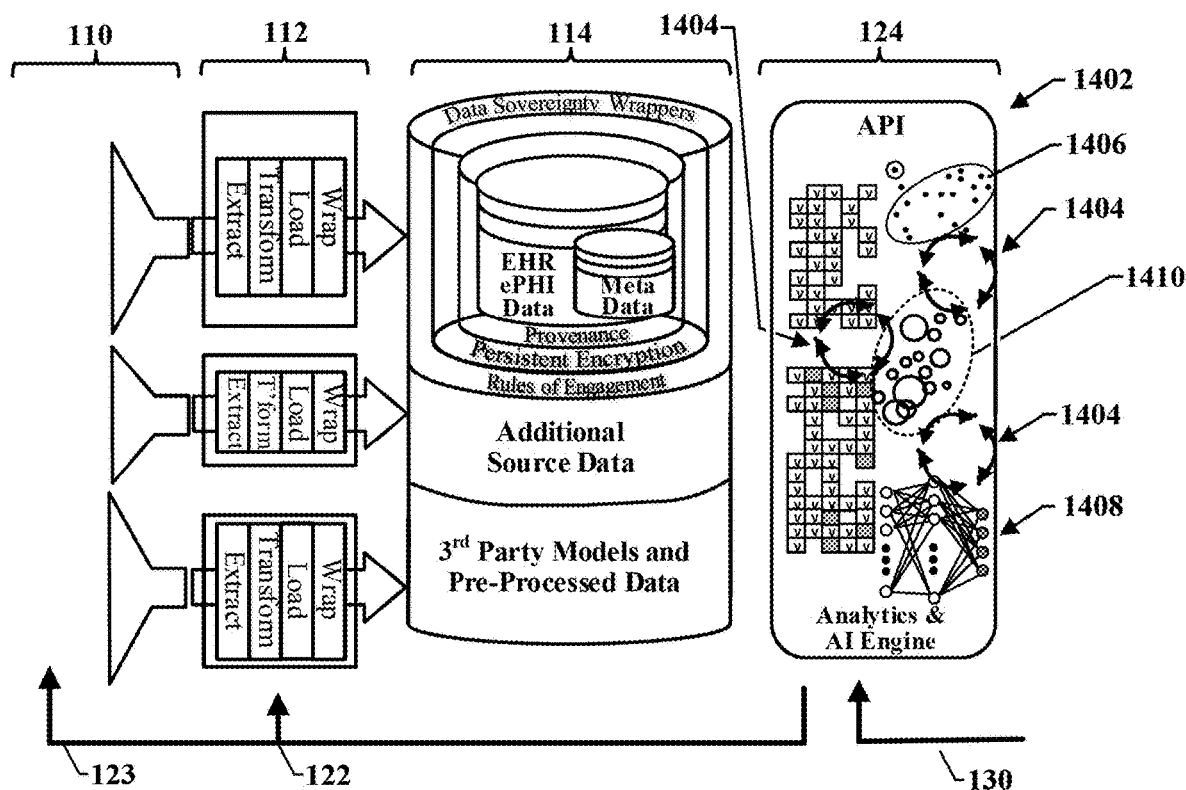
FIG. 14 is a process flow diagram showing certain features and aspects shown in FIG. 13A and elsewhere in this disclosure, for AI enhanced medical record exchange and common platform collaboration-based medical and public health situation assessment, and health services resource and response management in accordance with one or more embodiments.

FIG. 14 is a logic diagram of flows of certain features and aspects shown in FIG. 13A. In an embodiment, flows include data curation 110. Features of the data curation 110 can include filtering of data received from external sources, such as but not limited to ePHI and other health information received from a plurality of independent, differently structured instances of EHR systems 104, additional health related information from additional sources 106, and analysis model information from a plurality of third-party model suppliers 108. In an embodiment, the filters can be configured in accordance with trusted third-party brokered data use agreements (DUAs) and other contracts. In one or embodiments, such filters can be applied to each contributed dataset. Also enforcement of the filters can persist through many layers of many different transformations, different users, and different collaborative groups of users. Such application and persistence can help ensure data sovereignty throughout the system and the methods supported by the system. The data sovereignty can be enforced, and maintained throughout IE-DSW logic 112 extraction, genericizing, e.g., transformation to generic form, loading of the transformed generic form information and metadata, e.g., into templates, and wrapping as per source-specific SP specifications. Further features can include adaptability of the combined staging database 114 to store, and maintain data sovereignty of the multiple sources' metadata. This feature has significant benefits, as metadata can grow considerably during each transformation and as differently provenanced data are integrated.

Referring to FIG. 14, as described above, transform and concept alignment logic 124 can include a published API 1402 that can support transform and concept aligning with resources that include analyses tools 1404 achieving dimensional conformity and alignment of related concepts, from: formal ontologies (e.g., OWL), reference models (e.g., NIEM). Standardized vocabularies (e.g., SNOMED), clustering 1406, for example, unsupervised DL trained AI clustering, other neural networks 1408 providing ML/DL trained AI phenotyping, data dictionaries, both supervised and unsupervised techniques and data dictionaries. In an embodiment, the provided phenotyping retrieves, compares, and updates concept relationships in the Integrated Phenotype Reference Model 1410. Such alignment of related concepts facilitates collaboration on the collaboration platform 128, which can foster, for example, efficient multi-participant collaborative, multi-layer analyses of health-related information from a large of independent EHR systems and other sources.

Figure 15:
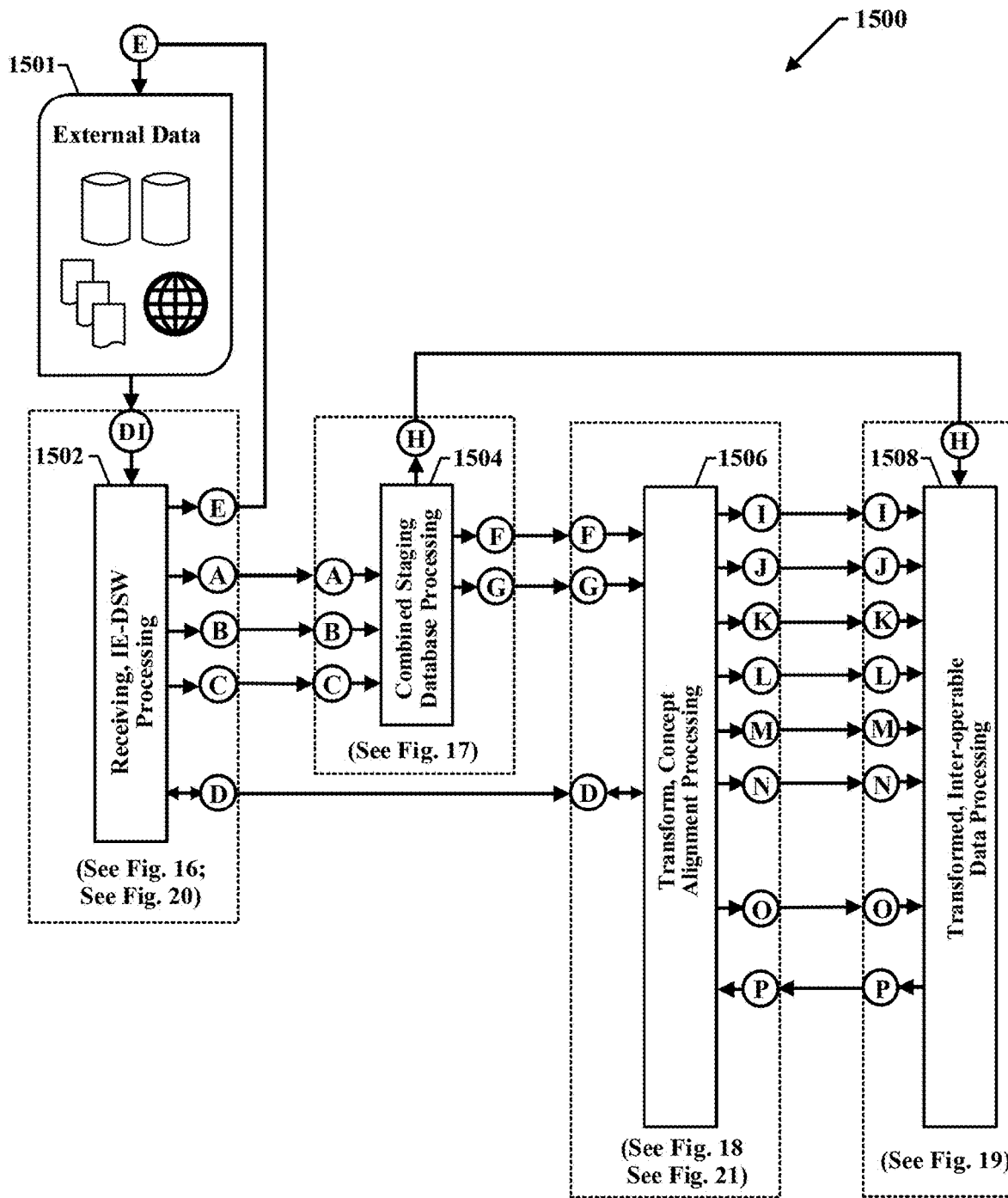
FIG. 15 is a process diagram, with annotation showing process inter-block flows, for an implementation of an example process according to methods for AI enhanced medical record exchange and common platform collaboration based medical and public health situation assessment, and health services resource and response management in accordance with one or more embodiments.

FIG. 15 shows a master diagram of a process 1500, in an implementation of a method of artificial intelligence (AI) enhanced medical record exchange and common platform collaboration based medical and public health situation assessment, and health services resource and response management in accordance with one or more embodiments. The FIG. 15 master diagram is arranged for convenience of description to comprise four logic flow portions. The arrangement into four logic flow portions is for convenience of description, including rendering various process-internal flows as inter-portion flows, thereby facilitating description of certain features. The arrangement into four logic portions is not intended as any limitation, or any indication of preference as to physical distribution or grouping of hardware, or allocation of functionality to hardware. The arrangement into logic portions is also not intended as a statement that arrangement into logic portions is necessary for description.

In an embodiment, the process 1500 can include a receiving and IE-DSW processing 1502, a combined staging database processing 1504, a transforming and concept alignment processing 1506, and a transformed, interoperable processing 1508. The receiving and IE-DSW processing 1502 can be an example implementation of the data curation 110 processes described above, e.g., in reference to FIG. 1, as well as an example implementation of the IE-DSW processing 402 also described above, e.g., in reference to FIG. 4, and as visible by the flow arrows passing through the in FIGS. 10, 11, 13A, and 14. The combined staging database processing 1504 can be an example implementation of the SP wrapped storing processes described above as performed by the combined staging database 114. The transforming and concept alignment processing 1506 can be an example implementation of the transform and concept alignment logic 124 described above, e.g., in reference to FIGS. 12A and 12B. The transformed, interoperable processing 1508 can be an example implementation of the virtual data warehouse and collaboration platform 128 described above, e.g., in reference to FIG. 13B.

Figure 16:
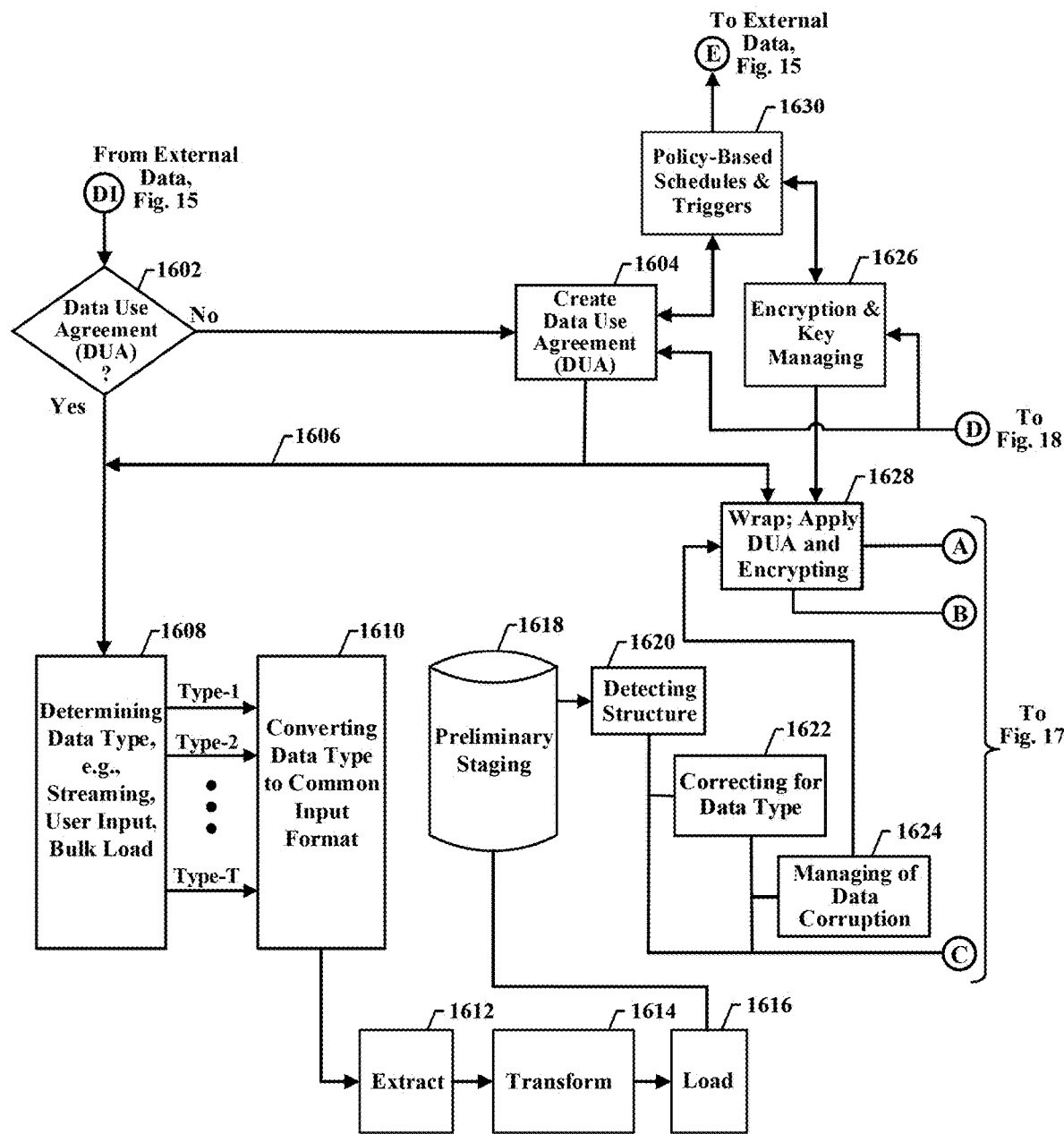
FIG. 16 shows a process flow diagram of an example implementation of multiple external source data receiving and input processing, and an example information extraction, transformation, and document sovereignty wrapper processing in the FIG. 15 process for methods for AI enhanced medical record exchange and common platform collaboration based medical and public health situation assessment, and health services resource and response management in accordance with one or more embodiments.
Figure 17:
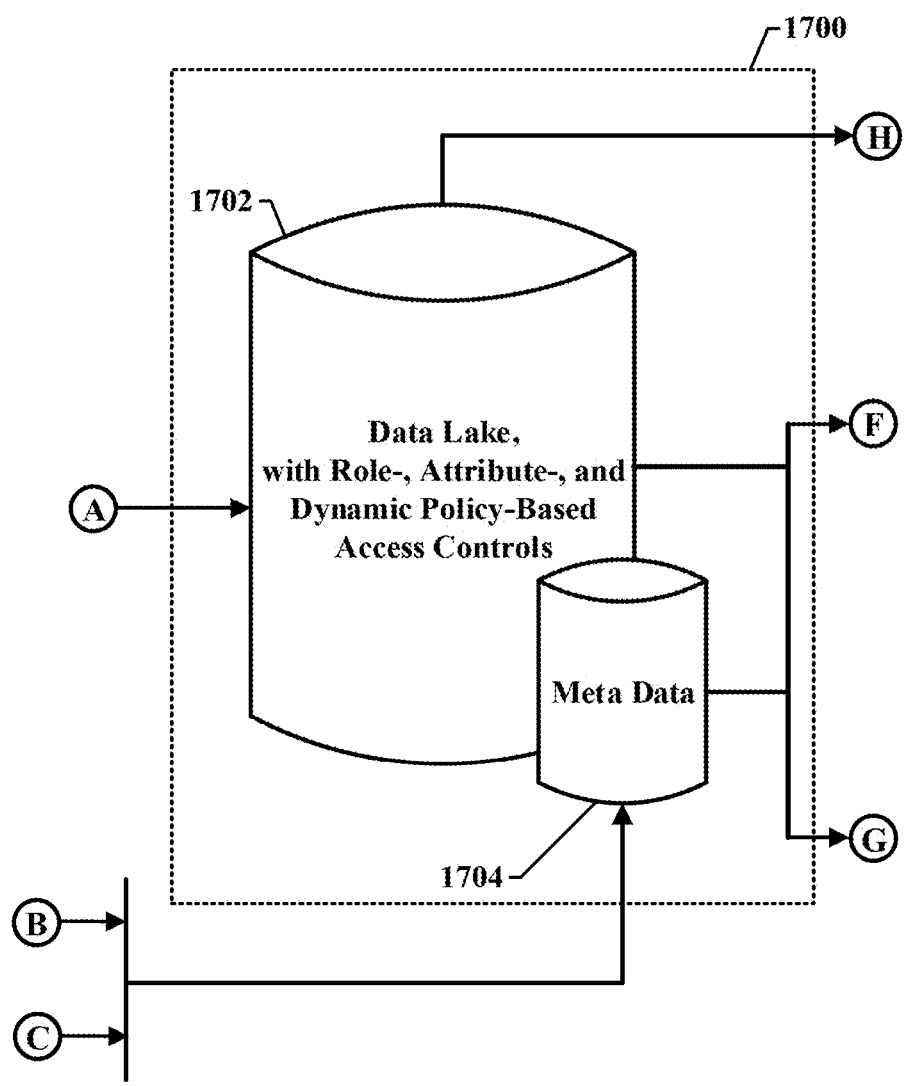
FIG. 17 shows a process flow diagram of an example implementation 1700 of combined staging database processing in the FIG. 15 process for methods for AI enhanced medical record exchange and common platform collaboration based medical and public health situation assessment, and health services resource and response management in accordance with one or more embodiments.
Figure 18:
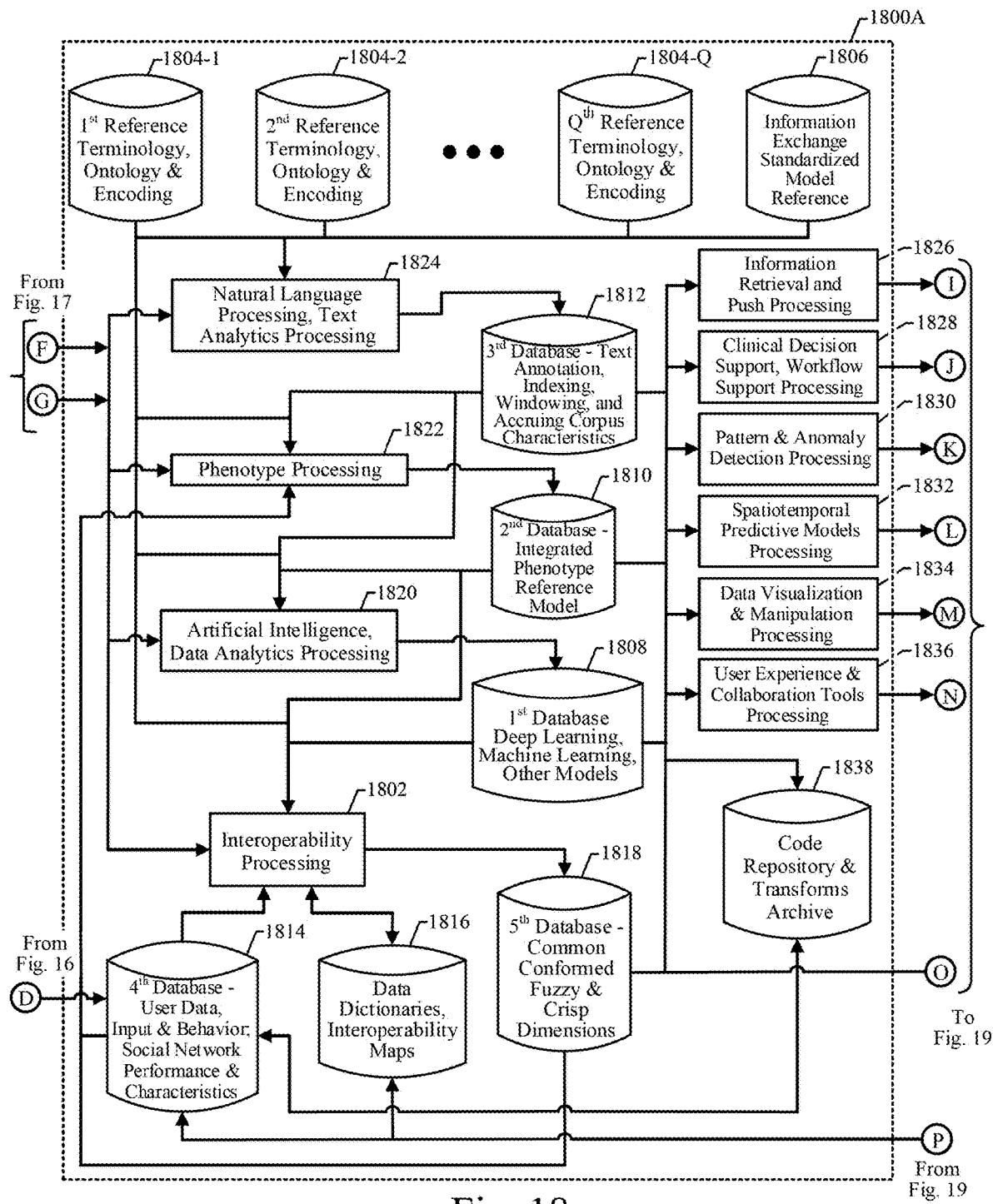
FIG. 18 shows a process flow diagram of an example implementation of transform and concept alignment processing in the FIG. 15 process for methods for AI enhanced medical record exchange and common platform collaboration based medical and public health situation assessment, and health services resource and response management in accordance with one or more embodiments.
Figure 19:
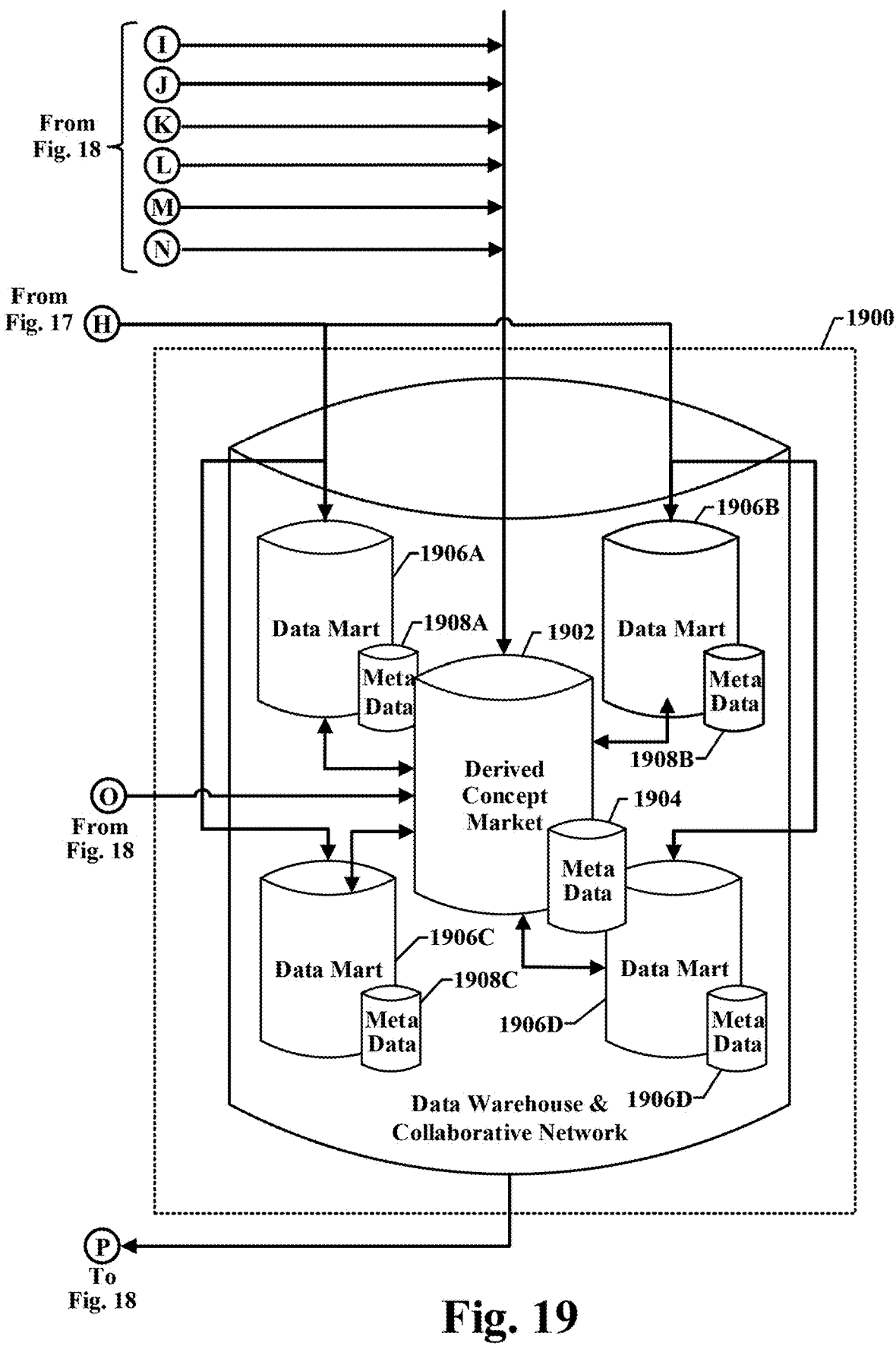
FIG. 19 shows a process flow diagram of an example implementation of the FIG. 15 transformed, interoperable data processing for AI enhanced medical record exchange and common platform collaboration based medical and public health situation assessment, and health services resource and response management in accordance with one or more embodiments.
Figure 20:
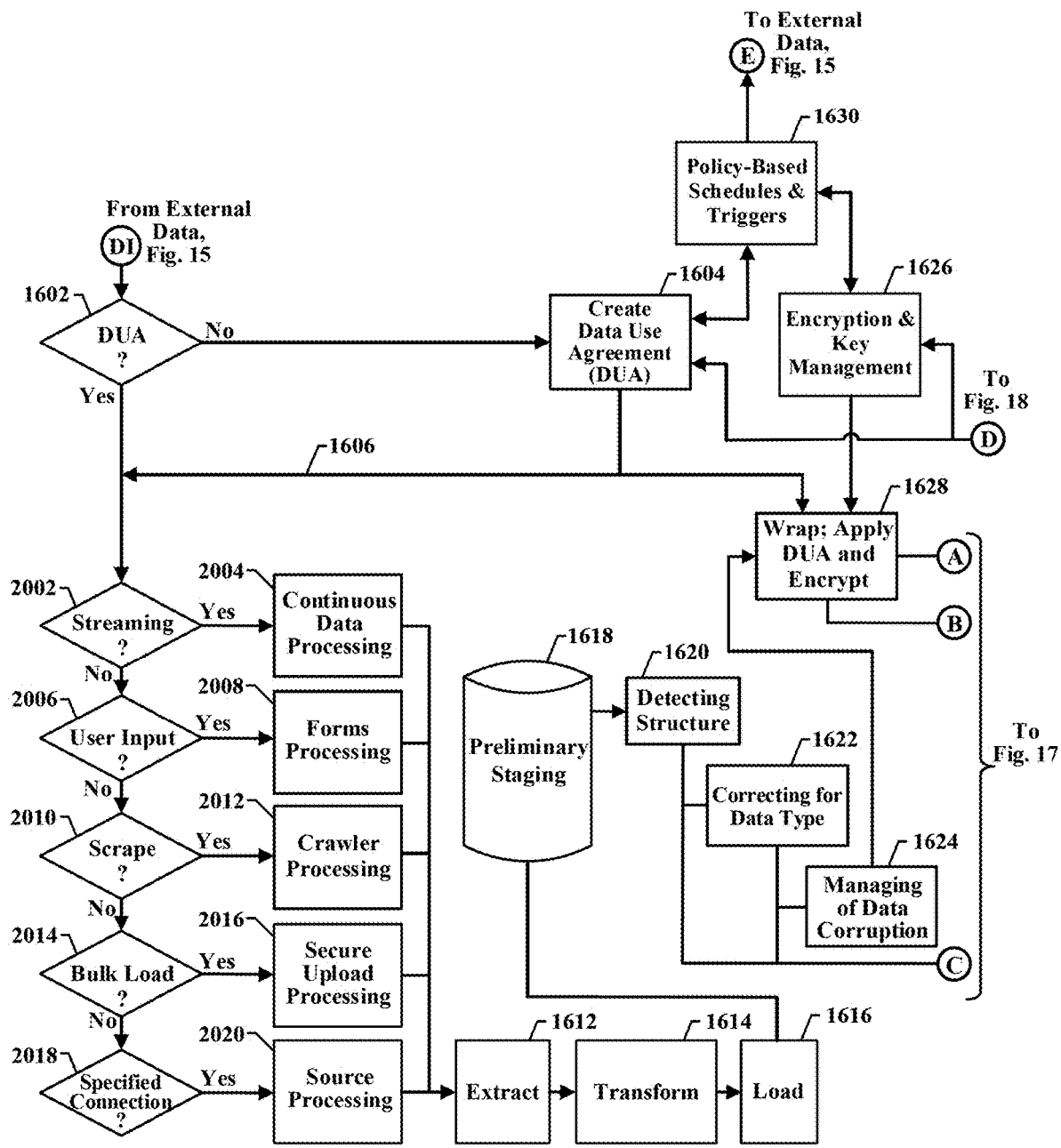
FIG. 20 shows a process flow diagram of an example alternative or further implementation of multiple external source data receiving and input processing, for the FIG. 15 process in methods for AI enhanced medical record exchange and common platform collaboration based medical and public health situation assessment, and health services resource and response management in accordance with one or more embodiments.
Figure 21:
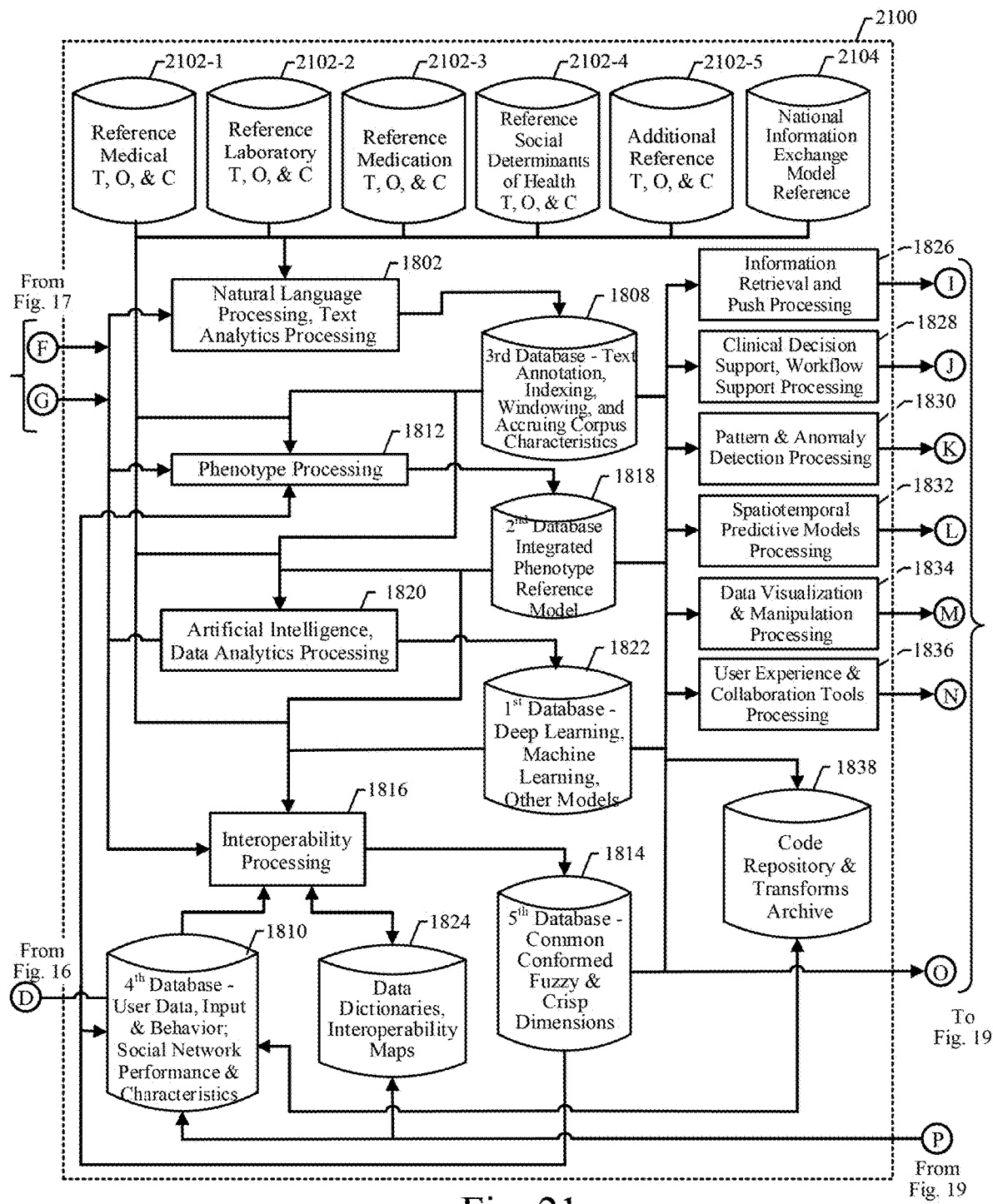
FIG. 21 shows a process flow diagram of an example alternative or further implementation of the transform and concept alignment processing in the FIG. 15 process, in methods for AI enhanced medical record exchange and common platform collaboration based medical and public health situation assessment, and health services resource and response management in accordance with one or more embodiments.

Visible on FIG. 15, a dotted line box encloses the graphic block for the IE-DSW processing 1502, and within the dotted line are references to FIG. 16 and FIG. 20. The references indicate FIG. 16 and FIG. 20, which are described in detail later, showing respective flow diagrams of example implementations of the receiving and IE-DSW processing 1502. In like manner, on FIG. 15 are three additional respective dotted line boxes, which surround, respectively, the combined staging database processing 1504 block, the transforming and concept alignment processing 1506 block, and the transformed, interoperable processing 1508 block. Within the dotted line box surrounding the combined staging database processing 1504 is a reference to FIG. 17, and within the dotted line box surrounding the transformed, interoperable processing 1508 is a reference to FIG. 19. These references indicate that FIG. 17 and FIG. 19, each described in more detail later in this disclosure, show, respectively, a detailed flow diagram of an example implementation of the combined staging database processing 1504, and a detailed flow diagram of an example implementation of the transformed, interoperable processing 1508. Within the dotted line box surrounding the transforming and concept alignment processing 1506 are references to FIG. 18 and FIG. 21, both of which are described in more detail later in this disclosure. These references that FIG. 18 and FIG. 21 show detailed flow diagrams of, respectively, a first example implementation and a second example implementation of the transforming and concept alignment processing 1506.

FIG. 15 shows for the receiving and IE-DSW processing 1502 a flow input "DI" and flow outputs "A," "B," "C," "D," and "E," and shows for the combined staging database processing 1504 flow inputs A, B, and C, and flow outputs "F," "G," and "H." FIG. 15 also shows for the transforming and concept alignment processing 1506 flow inputs F, G, D, and "P," and flow outputs "I," "J," "K," "L," "M," "N," and "O," and shows for the transformed, interoperable processing 1508 flow inputs H, I, J, K, L, M, N, and 0, and flow output P.

FIG. 16 and FIG. 20 show the same flow inputs and outputs as FIG. 15 shows for the receiving and IE-DSW processing 1502 that for which FIG. 16 and FIG. 20 show implementations. FIGS. 17 and 19 show, respectively, the same flow inputs and outputs as FIG. 15 shows for the combined staging database processing 1504, and the transformed, interoperable processing 1508 that the FIGS. 17 and 19 flows respectively implement. FIG. 18 and FIG. 21 show the same flow inputs and outputs as FIG. 15 shows for the transforming and concept alignment processing 1506, for which FIG. 18 and FIG. 21 show implementations.

Interconnecting, in accordance with the interconnects visible on FIG. 15, the respective flow inputs and outputs of FIGS. 16, 17, 18, and 19 will form an integrated flow schematic of an example detailed implementation of the process 1500. Substituting the FIG. 20 implementation for the FIG. 16 implementation of the receiving and IE-DSW processing 1502, using interconnects visible on FIG. 15, the respective flow inputs and outputs of FIGS. 20, 17, 18, and 19, will form an integrated schematic of another example detailed implementation of the process 1500. In like manner, substituting the FIG. 21 implementation for the FIG. 18 implementation of the transforming and concept alignment processing 1506, and interconnecting, in accordance with the interconnects visible on FIG. 15, the respective flow inputs and outputs of FIGS. 16, 17, 21, and 19, will form a unitary flow schematic showing another example detailed implementation of the process 1500. In addition, substituting the FIG. 20 for the FIG. 16 implementation of the receiving and IE-DSW processing 1502, in combination with substituting the FIG. 21 implementation for the FIG. 18 implementation of the transforming and concept alignment processing 1506, and interconnecting the figures as described above, forms an integrated flow schematic of yet another example detailed implementation of the process 1500.

An embodiment in accordance with the FIG. 15 process 1500 will now be described, assuming the FIG. 16 implementation of the receiving and IE-DSW processing 1502, the FIG. 17 implementation of the combined staging database processing 1504, the FIG. 18 implementation of the transforming and concept alignment processing 1506, and the FIG. 19 implementation of the transformed, interoperable processing 1508. For purposes of description, an example of the process 1500 in accordance with this example implementation, will be referenced as the "first implementation process 1500." An example instance of the first implementation process 1500 will be described assuming the system 100 as the environment, and assuming that the external source is a particular one of the EHR systems 104, there is no DUA in place between the entity managing the system 100 and the particular one of the EHR systems 104, that the DUA includes the SP specifications for performing the SP wrapping, and that third-party model supplier 108 models are already loaded onto the virtual data warehouse and collaboration platform 128.

Descriptions of various features of and of example operations according to the process 1500 include references to FIG. 1 and to other appended figures. Such references are to further assist in understanding of the process 1500, through illustration by examples. Such references are not intended as a statement that practices in accordance with disclosed embodiments are limited to system 100 or to above disclosed implementations of the system 100 logic blocks.

Referring to FIG. 16, in an embodiment, operations in the first implementation process 1500 can include, e.g., responsive to receiving an EHR data from a particular one of the EHR systems 104, proceeding to the process flow 1600, and in the process flow 1600 determining 1602 whether there is a DUA between the entity managing the system 100 and the particular one of the EHR systems 104. As stated above, it is assumed for this example that no DUA is in place. Accordingly, the determining 1602 returns a negative result and, in response, the process flow 1600 can proceed to computerized DUA formation 1604. The computerized DUA formation 1604 can include a DUA generation resource. In an embodiment, the DUA can determine, or can embody the SP specifications for subsequent wrapping, in later operations of the process flow 1600. In an embodiment, the DUA can encode an identifier for the SP specifications, and the process flow 1600 can include operations for storing the SP specifications in a manner retrievable, for example, using the encoded identifier. In one or more embodiments, SP specification can be communicated pursuant to or associated with creation of the DUA, between the source of the dataset (e.g., EHR system 104), and an entity managing the process 1500.

In an embodiment, on completion of the computerized DUA formation 1604 the process flow 1600 can proceed, e.g., via a return path 1606, to determining 1608 the type of the received external sourced data. Reasons for determining 1608 the type of the received health-related data can include configuring the subsequent step, which can be the preprocessing 1610. As will be described in more detail in reference to the FIG. 20 alternative configuration "type[s]," determining 1608 can include streaming health data, bulk-type load health data, real-time EHR system user entered data, and other examples. Assuming the received EHR data is of a type recognized or acceptable to the determining 1608, the process flow 1600 can proceed to preprocessing 1610 the received data into a common format configured for feeding the first of subsequent steps. In one or more embodiments, for particular data transfers, operations at 1608 and 1610 may require performance only once, e.g., at the beginning of the data transfer.

From the preprocessing 1610 the process flow 1600 flow can then proceed to extracting 1612 which the information content, e.g., ePHI information content and EHR metadata information from EHR data. The process flow 1600 can then proceed to transforming 1614 the extracted information and metadata, e.g., ePHI information and EHR metadata information, to a generic transformed PHI information and generic transformed EHR metadata, and then to loading 1616 the generic transformed PHI information and generic transformed EHR metadata into the preliminary staging resource 1618. In one or more embodiments, the preliminary staging resource 1618 can function as a buffer memory, for holding transformed generic form health information and transformed, generic form metadata prior to wrapping, as described in more detail in the following paragraphs.

The extracting 1612, transforming 1614, and loading 1616 can be example implementations of operations in the computerized information extracting and data sovereignty wrapping 402 described above in reference to FIG. 4. For example, the extracting 1612 and transforming 1614 can be implementations, respectively, of the first branch information extracting 406A and first branch transforming 406B, and the loading 1616 can be an implementations of the first branch loading 406C.

With continuing reference to FIG. 16, over intervals following storing the generic transformed PHI information and EHR metadata in the preliminary staging resource 1618, the process flow 1600 can proceed to detecting 1620 structure of the generic transformed PHI information and generic transformed EHR metadata. For example, after the detecting 1620, the process flow 1600 can proceed to correcting 1622 for data type, and managing 1624 data corruptions. In an embodiment, over time intervals that may be concurrent with, or separate from time intervals corresponding to the detecting 1629, correcting 1622, and managing 1624, operations in the process flow 1600 can include an encryption and key managing process 1626 configuring a wrapping 1628 that, when applied, can include encrypting and wrapping the generic form health-related data and generic form metadata as received, after any correcting 1622 for data type, and any managing 1624 of data corruptions. In an embodiment, the configuring operations by the encryption and key managing process 1626 can include, for example, loading a process, e.g., computer-executable instructions into a computer resource allocated, or dedicated, or assigned to perform the wrap process. The process, in various embodiments, can be configure in accordance with the DUA, i.e., to meet the SP specifications defined by the DUA. The configuring can include defining an SP wrapper for the external sources information and metadate, for example, assuming an EHR system 104 source, an SP specification for an EHR information SP wrapping such as the EHR information SP wrapping 302 described above.

Referring to FIG. 15 and FIG. 16, in an embodiment, information for use by, or for controlling aspects of the encryption and key managing process 1626 can be exchanged, via flow input-output point D, between the key managing process 1626 and a database that can be internal to the transform, concept alignment processing 1506, which is described in more detail later in this disclosure.

In an embodiment, operations in the process flow 1600 can include, over one or more time intervals subsequent to above-described configuring operations by the encryption and key managing, feeding output of the wrapping 1628 to the combined staging database processing 1504, via flow output point of the process flow 1600 and into flow input point A of the processing 1504. The combined staging database processing 1504 can then store wrapped, generic transformed versions of EHR system 104 sourced health-related information and metadata.

In an embodiment, operations in the process flow 1600 can include communication to the combined staging database processing 1504 of information regarding the wrapping and encryption applied by wrapping 1628. The communication can be, for example, from flow output point B to flow input point B of the combined staging database processing 1504.

In an embodiment, the process flow 1600 can also include outputting information regarding any one or more among detecting 1620 structure of the generic transformed PHI information and generic transformed EHR metadata, correcting 1622 for data type, and managing 1624 data corruption. As visible in FIG. 16, in an implementation, the process flow 1600 can output such information, for example from process flow 1600 flow output point C to flow input point C of the combined staging database processing 1504.

In an embodiment, the process flow 1600 can include a policy-based schedules and triggers process and, in an example implementation, said process can feed information, from example, from flow output point E to representative flow input point E of the external sources 1501.

Referring to FIGS. 1, 4, 15, and 16, it will be understood that operations in the extracting 1612, transforming 1614, and loading 1616 can be performed, for example, by the IE-DSW logic 11. Referring to the same figures, together with FIG. 17, the combined staging database processing 1504 can implement the combined staging database 114 described above.

FIG. 17 shows a process flow diagram of an example implementation of the combined staging database processing 1504 in the FIG. 15 process 1500. The implementation can be for methods for AI enhanced medical record exchange and common platform collaboration based medical and public health situation assessment, and health services resource and response management in accordance with one or more embodiments.

Referring to FIG. 17, the implementation logic can include a data lake 1702 and, in an embodiment, the data lake 1702 can be provided with role-, attribute-, and dynamic policy-based access controls. An example of role-based and attribute-based access controls can include qualifications or permissions assigned to participants, e.g., participants 602, to access data with particular attributes as specified in an appropriate DUA. An example of dynamic policy-based access controls can include changing the assigned permissions to access data with particular attributes, depending on the situational context. Proof of such qualifications or permissions can be communicated, as an example, by a subscription name, password sequence, or comparable verification protocol. In an embodiment, operations of the data lake 1702 can include, e.g., via flow pads A and B on FIGS. 16 and 17, communication of suitably wrapped EHR information and EHR metadata, respectively. Flow output pads of the FIG. 17 resource include an output pad F and output pad G.

FIG. 18 shows a flow diagram of an example process flow 1800 that can implement the transform and concept alignment processing 1506 in the FIG. 15 process 1500. The example process flow 1800 can be further to AI enhanced medical record exchange and common platform collaboration based medical and public health situation assessment, and health services resource and response management in accordance with one or more embodiments. Description of operations according to the process flow 1800 will use certain assumptions. One is that EHR system 104 sourced dataset described above has been received by the FIG. 16 process flow 1600, i.e., information content and metadata have been extracted, genericized, and stored in an SP wrapping in the combined staging database processing 1504, e.g., as per the FIG. 17 implementation. The receiving, as visible in FIG. 18, can be via process flow 1800 flow reception points F and G, respectively, connected to FIG. 17 flow output points F and G.

In overview, operations of the process flow 1800 include interoperable processing 1802, for transforming into one or more alternative collaboration platform 128 supported knowledge presentation schema concepts represented by the genericized information content of, for example, the EHR system 104 sourced dataset and metadata store in the FIG. 17 data lake 1702 and metadata storage 1704.

Operations according to process flow 1800 will be described in reference to the example EHR dataset. However, in one or more embodiments, and in various applications of such embodiments concept information carried or embodied in the external source data, e.g., EHR system 104 sourced data, may span multiple datasets, combinations of datasets and results of processing datasets. Description of example operations of the interoperable processing 1802 will therefore assume that prior processing has accumulated a usable content of databases that feed the interoperable processing 1802. For example, it will be assumed that prior processing, or a preloading, or operations in particularly configured start-up process, or combinations thereof, have loaded the process flow 1800 first database 1808, holding deep learning, machine learning data, and loaded the process flow 1800 second database 1810, holding integrated phenotype reference model information, and the process flow 1800 third database 1812, holding text annotation, indexing, windowing, and accrued corpus characteristics data. Likewise, it will be assumed that prior processing, or a preloading, or operations in particularly configured start-up process, or combinations thereof, have loaded the process flow 1800 fourth database 1814, holding user data, user input and behavior patterns, as well as social network performance and characteristics data. It will also be assumed that prior processing, or a preloading, or operations in particularly configured start-up process, or combinations thereof, have loaded the process flow 1800 database 1816, holding data dictionaries and interoperability maps available for interactive updating by the interoperability processing 1802.

It will be understood that "loaded," in this context, can encompass a loading of the identified databases, and of other of the process flow 1800 databases as will be described, that is sufficient such that successive operations, based on successively obtained new datasets, e.g., new EHR system 104 sourced datasets, will reliably produce a convergence of system or process state to a stable steady state.

In an embodiment, various operations in the process flow 1800 can be configured to receive, in addition to the wrapped, genericized health related information and associated genericized metadata, run-time access to reference terminology, ontology and encoding data from a resource of reference terminology, ontology and encoding databases, and one or more information exchange standardized model references. Regarding the reference terminology, ontology and encoding databases, in an embodiment these can include, for example, as visible in FIG. 18, a first reference terminology, ontology and encoding database 1804-1, a second reference terminology, ontology and encoding database 1804-2, . . . , and a Qth reference terminology, ontology and encoding database 1804-Q (collectively "reference terminology, ontology and encoding databases 1804"). Q can be any integer, including integer one. Regarding the information exchange standardized model references, an example configuration, also visible in FIG. 18, can include information exchange standardized model reference 1806.

Referring to FIG. 18, it will be understood the representation of the reference terminology, ontology and encoding databases 1804 by separate blocks is a logical representation and is not intended as any limitation as to physical arrangement or separation of respective storage. Implementation of the reference terminology, ontology and encoding databases 1804 can include, for example, storage of multiple reference terminology, ontology and encoding databases 1804 in common, shared storage space of a common, shared storage resource. Implementation of one or more of the reference terminology, ontology and encoding databases 1804 can also include remote storage of, or subscription access to one or more of the reference terminology, ontology and encoding databases 1804.

In an embodiment, operations in the process flow 1800 can include receiving and applying interoperability processing 1802 to wrapped, genericized medical and public health related information, and wrapped, genericized metadata, e.g., via accesses of the data lake 1702. Such accesses can be initiated, for example, by the process flow 1800, e.g., associated with a user or collaboration of users of the collaboration platform 128 using applications in the app market 134. As visible in FIG. 15, instances of interoperability processing 1802 can receive, by pushes to the process 1802 or by accesses performed by the process 1802, reference terminology, ontology and encoding data from the up to Q reference terminology, ontology and encoding databases 1804-1, 1804-2, . . . , 1804-Q, together with information exchange standardized model data from the information exchange standardized model reference 1806; deep learning, machine learning, and other models data, from the process flow 1800 first database 1808; phenotype reference model information from the process flow 1800 second database 1810; text annotation, indexing, windowing, and accruing corpus characteristics data from the process flow 1800 third database 1812; user data, input and behavior, social network performance and characteristics data from the process flow 1800 fourth database 1814; and data dictionary(ies) and interoperability map(s) data from the data dictionary(ies) and interoperability map(s) database 1816. Results of the interoperability processing 1802 can be loaded as common conformed dimensions, which could have either fuzzy or crisp degrees of certainty, into the process flow 1800 fifth database 1818.

Referring to FIGS. 1, 15, 18, and 19, it is seen that the common conformed fuzzy and crisp dimensions data can implement the hosting, on the virtual database and collaborative platform 128, of transformed and EHR sourced health related information, for collaborative analyses by the FIG. 15 process 1500, a transformed, interoperable processing 1508.

Referring to FIG. 18, operations in the process flow 1800 can include, in addition to the above-described interoperability processing 1802, a process flow 1800 artificial intelligence data analytics processing 1820, applied to transformed generic EHR data from the FIG. 17 data lake 1702 and metadata storage 1704, also using reference terminology, ontology and encoding data from the up to Q reference terminology, ontology and encoding databases 1804-1, 1804-2, . . . , 1804-Q, together with information exchange standardized model data from the information exchange standardized model reference 1806, and input of integrated phenotype reference model information from the process flow 1800 second database 1810 and text annotation, indexing, windowing, and accruing corpus characteristics data from the process flow 1800 third database 1812. Results of the process flow 1800 artificial intelligence data analytics processing 1820 can be loaded, as updates or supplements to deep learning, machine learning, and other model data in the process flow 1800 first database 1808.

Operations in the process flow 1800 can also include, in addition to the above-described interoperability processing 1802 and process flow 1800 artificial intelligence data analytics processing 1820, a process flow 1800 phenotype processing 1822, applied to transformed generic EHR data from the FIG. 17 data lake 1702 and metadata storage 1704, also using reference terminology, ontology and encoding data from the up to Q reference terminology, ontology and encoding databases 1804-1, 1804-2, . . . , 1804-Q, together with information exchange standardized model data from the information exchange standardized model reference 1806, and text annotation, indexing, windowing, and accruing corpus characteristics data from the process flow 1800 third database 1812. Results of the process flow 1800 phenotype processing 1822 can be loaded, as updates or supplements integrated phenotype reference model data in the process flow 1800 second database 1810.

Operations in the process flow 1800 can include, in addition to the above-described interoperability processing 1802, process flow 1800 artificial intelligence data analytics processing 1820, and process flow 1800 phenotype processing 1822, a natural language processing 1824, also applied to transformed generic EHR data from the FIG. 17 data lake 1702 and metadata storage 1704, also using reference terminology, ontology and encoding data from the up to Q reference terminology, ontology and encoding databases 1804-1, 1804-2, . . . , 1804-Q, and the information exchange standardized model data from the information exchange standardized model reference 1806. Results of the process flow 1800 natural language processing 1824 can be loaded, as updates or supplements to text annotation, indexing, windowing, and accruing corpus characteristics data in the process flow 1800 third database 1812.

In an embodiment, the process flow 1800 fifth database 1818 content of common conformed fuzzy and crisp dimensions data, as updated by the interoperability processing 1802, the process flow 1800 first database 1808 content of deep learning, machine learning, and other model data, as updated by the process flow 1800 artificial intelligence data analytics processing 1820; the process flow 1800 second database 1810 content of integrated phenotype reference model data as updated by the process flow 1800 phenotype processing 1822, and the process flow 1800 third database 1812 content of text annotation, indexing, windowing, and accruing corpus characteristics data as updated by the process flow 1800 natural language processing 1824 can feed any one, or any combination or sub combination among the following example configuration of process flow 1800 processes: information retrieval and information push processing 1826; clinical decision support and workflow support processing 1828; pattern and anomaly detection processing 1830; spatiotemporal predictive models processing 1832; data visualization and data manipulation processing 1834; and user experience and collaboration tools processing 1836.

In an embodiment, the process flow 1800 can also include a code repository and a data transformations archive 1838.

FIG. 19 illustrates a functional block schematic of a virtual data warehouse and collaboration network 1900, hosting an interoperable data resource, showing an example implementation of the FIG. 15 virtual data warehouse and collaboration platform and interoperable data resource, for methods for AI enhanced medical record exchange and common platform collaboration based medical and public health situation assessment, and health services resource and response management in accordance with one or more embodiments.

FIG. 20 shows a process flow diagram of an example of a process flow 2000 of operations in the FIG. 16 process flow 1600, comprising a specific implementation of the determining 1608 of data type and format and a corresponding specific implementation of the converting by preprocessing 1610 of received data type and format to a common format. In an example instance, operations of the process flow 2000 can include a determining 2002 of whether the EHR data is streaming data. Assuming the determining 2002 produces a positive result, the process flow 2000 can proceed to continuous data processing 2004, which can feed appropriately formatted continuous data to the extracting 1612, for processing as described in reference to FIG. 16.

In an embodiment, assuming the determining 2002 produces a negative result, the process flow 2000 can proceed sequentially, to determining 2006 whether the received EHR data is a user input, e.g., in real time to an EHR system standard GUI or other interface, and if the answer is "yes," can proceed to forms processing 2008. In such an embodiment, if the determining at 2006 obtains a negative result, the process flow 2000 can proceed to determining 2010 if the received EHR data is a scrape and, if "yes," can proceed to crawler processing 2012 and then to extracting 1612, for processing as described in reference to FIG. 16. If the result of the determining 2010 is negative, the process flow 2000 can proceed to determining 2014 whether the EHR data is part of, e.g., a beginning of a bulk load and, if the answer is "yes," can proceed to secure upload processing 2016 and then, as described above, to processing as described in reference to FIG. 16. In the example configuration visible in Fig. if the result of the determining 2014 is negative, the process flow 2000 can proceed to determining 2018 whether the EHR data is a specified connection, i.e., is in a form acceptable to the process, and, if the answer is "yes," can proceed to source processing 2020, and then proceed to extracting 1612 and further operations as described in reference to FIG. 16.

In an alternative embodiment, two or more of the determining steps can be performed in parallel or substantially in parallel, and the combination of operations can be collectively referenced as "EHR data type determination."

FIG. 21 shows a process flow diagram of an example alternative or further implementation of the transform and concept alignment processing in the FIG. 15 process for methods for AI enhanced medical record exchange and common platform collaboration based medical and public health situation assessment, and health services resource and response management in accordance with one or more embodiments.

The alternative includes Reference Medical terminology, ontology and coding (T, O, & C) 2102-1, Reference Laboratory T, O, & C 2102-2; Reference Medication T, O, & C 2102-3, Reference Social Determinants of Health T, O, & C 2102-4; Additional Reference T, O, & C 2102-5; and National Information Exchange Model Reference 2102-6.

Computer System

Figure 22:
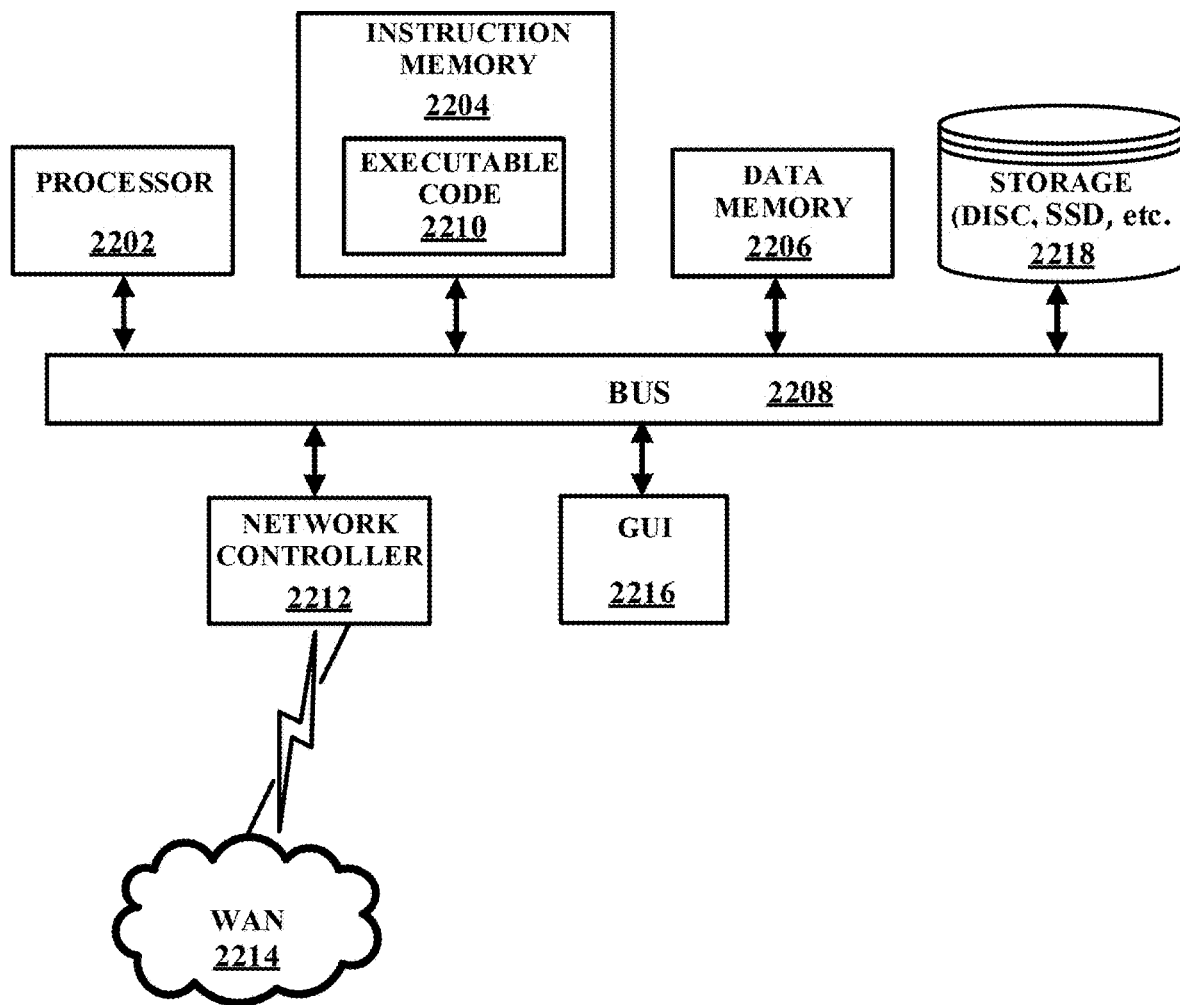
FIG. 22 is a functional block schematic of an example implementation of a computing system on which aspects of the present disclosure can be practiced.

FIG. 22 illustrates in simplified schematic form a computer system 2200, on which aspects of the present disclosure can be practiced. The computer system 2200 can include a hardware processor 2202 communicatively coupled to an instruction memory 2204 and to a data memory 2206 by a bus 2208. The instruction memory 2204 can be configured to store, on at least a non-transitory computer readable medium as described in greater detail below, executable program code 2210. The hardware processor 2202 may include multiple hardware processors and/or multiple processor cores. The hardware processor 2202 may include cooperation with hardware processors from different devices. The computer system 2200 may execute one or more basic instructions included in the executable program code 2210. The computer system 2200 can include a network interface 2212 communicatively connected to the bus 2208, for interfacing to a wide area network (WAN), e.g., the Internet 2214. Also communicatively connected to the bus 2208 can be a GUI 2216. The computer system 2200 may also include a mass storage 2218, which can be accessible to the hardware processor 2202 via the bus 2208.

Relationship between Hardware Processor and Executable Program Code

The relationship between the executable program code 2210 and the hardware processor 2202 is structural; the executable program code 2210 is provided to the hardware processor 2202 by imparting various voltages at certain times across certain electrical connections, in accordance with binary values in the executable program code 2210, to cause the hardware processor to perform some action, as now explained in more detail.

A hardware processor 2202 may be thought of as a complex electrical circuit that is configured to perform a predefined set of basic operations in response to receiving a corresponding basic instruction selected from a predefined native instruction set of codes.

The predefined native instruction set of codes is specific to the hardware processor; the design of the processor defines the collection of basic instructions to which the processor will respond, and this collection forms the predefined native instruction set of codes.

A basic instruction may be represented numerically as a series of binary values, in which case it may be referred to as a machine code. The series of binary values may be represented electrically, as inputs to the hardware processor, via electrical connections, using voltages that represent either a binary zero or a binary one. The hardware processor interprets the voltages as binary values.

Executable program code may therefore be understood to be a set of machine codes selected from the predefined native instruction set of codes. A given set of machine codes may be understood, generally, to constitute a module. A set of one or more modules may be understood to constitute an application program or "app." An app may interact with the hardware processor directly or indirectly via an operating system. An app may be part of an operating system.

Figure 23:
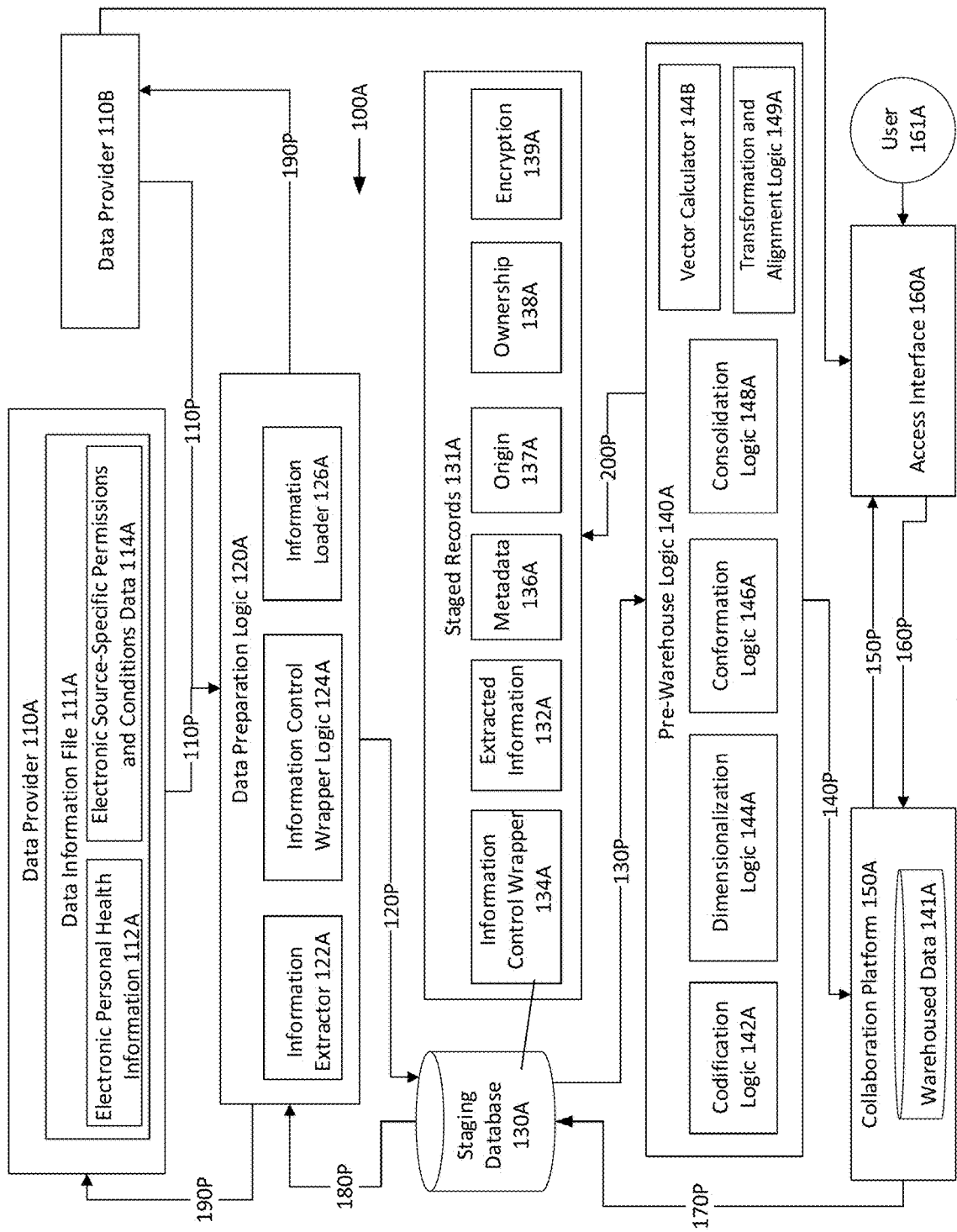
FIG. 23 shows a schematic view of the system.

FIG. 23 shows a data preparation system 100A illustrating a first data provider 110A configured to provide a data information file 111A; a multi-source health data integration logic 120A configured to receive 110P said data information file 111A from the first data provider 110A. The multi-source health data integration logic 120A containing: an information extractor 122A configured to extract information from the data information file 111A; an information control wrapper logic 12A configured to wrap the data information file with an information control wrapper 134A. The multi-source health data integration logic may also comprise an information loader 126A. The multi-source health data integration logic 120A may be configured generate 120P cleaned and sovereignty wrapped data (transformed interoperable data). The system may include a staging database 130A configured to receive cleaned and sovereignty wrapped data (transformed interoperable data) from the multi-source health data integration logic 120A; said staging database comprising a plurality of staged records 131A. The staged records may comprise an information control wrapper 134A configured to restrict usage of the data information; extracted information 132A in a standardized format; wherein the extracted information contains electronic health records; metadata 136A configured to provide details about the extracted information; origin data 137A comprising source information of the extracted information; ownership data 138A comprising information about what data provider owns the extracted information; encryption data 139A comprising information on how to encrypt the extracted information. The system 100A may comprise a pre-warehouse logic 140A configured to receive said staged records 131A from the staging database; said pre-warehouse logic may comprise a codification logic 142A; a dimensionalization logic 144A; a conformation logic 146A; a consolidation logic 148A, and a transformation and alignment logic 149A to transform and align related concepts; said transformation and alignment logic comprising a knowledge representation tool and an analysis tool. The pre-warehouse logic 140A may be configured to generate 140P transformed interoperable data warehoused in 141A. The system may comprise a collaboration platform 150A configured to receive said warehoused data 141A. The warehoused data may be stored in data warehouse 141B. The pre-warehouse logic 140A may further be configured to generate 200P new sovereignty data arising from data transformation.

Figure 24:
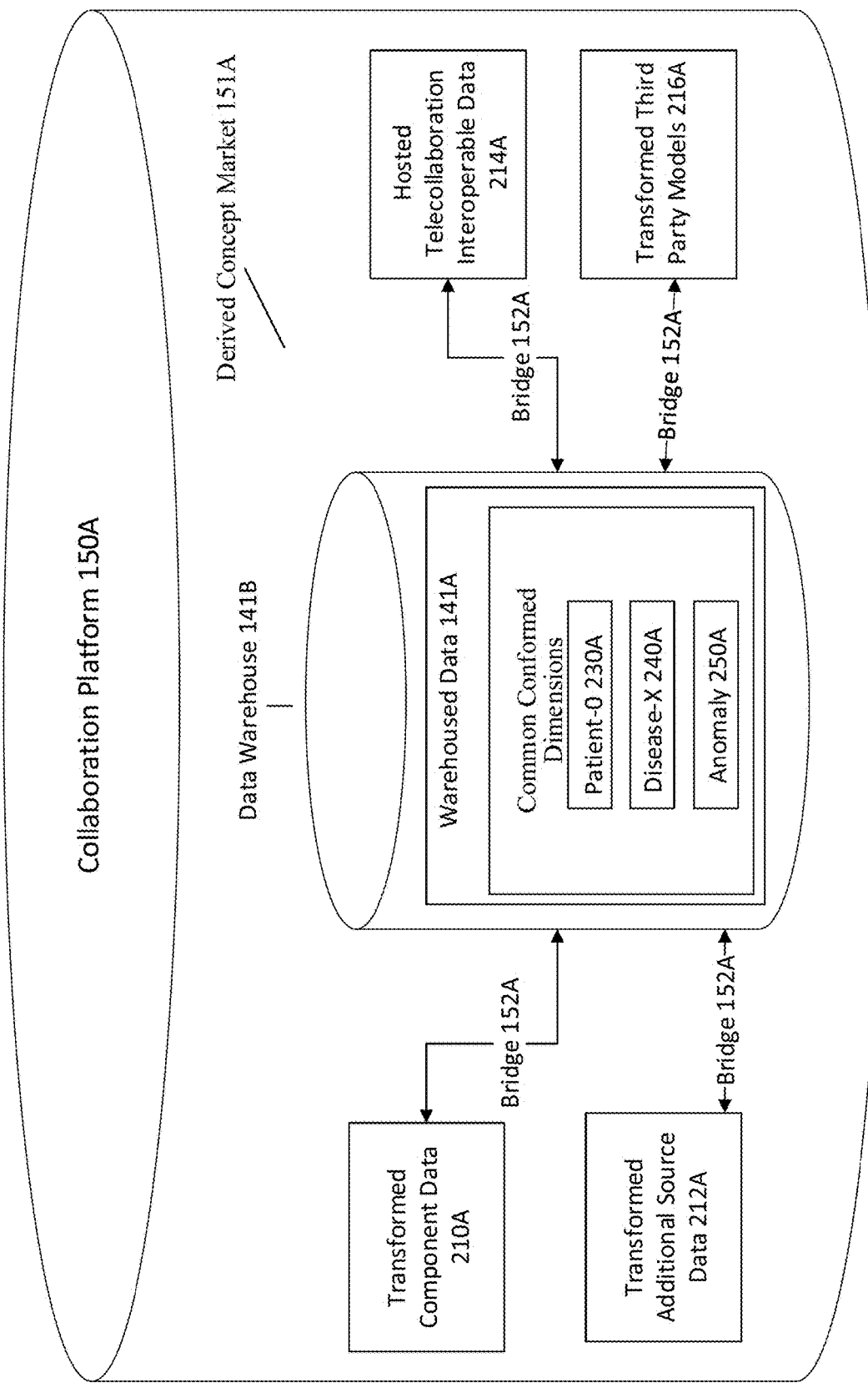
FIG. 24 shows a schematic view of the collaboration platform.

Referring to FIG. 24, the collaboration platform 150A may be configured to provide: a derived concept market 151A containing warehoused data 141A stored in a data warehouse 141B in common conformed dimensions. The collaboration platform may comprise one or more bridges 152A connecting a transformed component data 210a, transformed additional source data 212A, hosted telecollaboration interoperable data 214A, and transformed third party models 216A.

Referring back to FIG. 23, the system may comprise an access interface 160A configured to make said warehouse data accessible to a user 161A.

Figure 25:
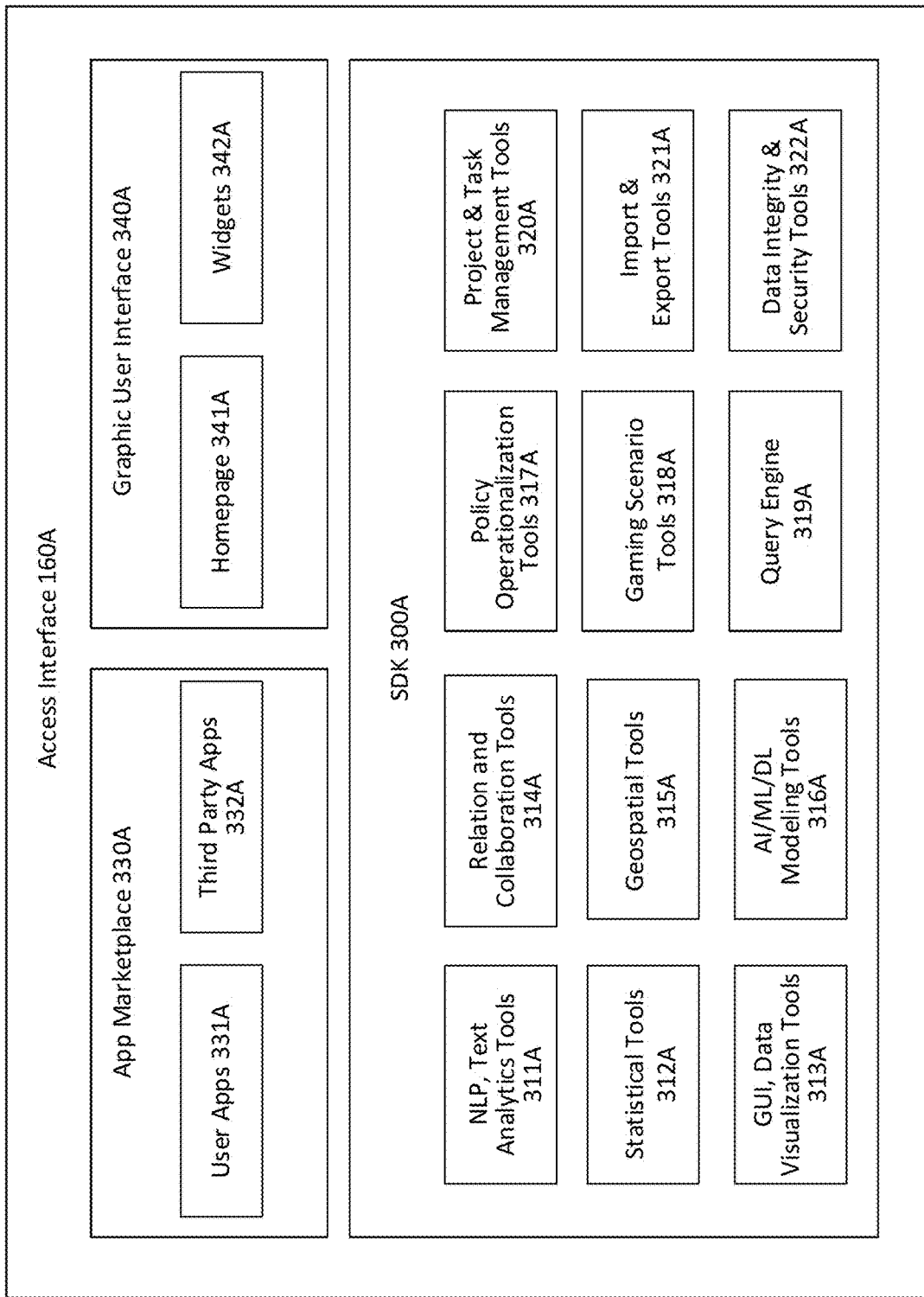
FIG. 25 shows a schematic view of the access interface.

As shown in FIG. 25, the access interface 160A may comprise: an app market place 330A; a graphic user interface 340A; and a software development kit 300A. As shown in FIG. 23, the warehouse data may be accessible to the first data provider 110A via the access interface 160A.

The first data provider may comprise a computer. The computer may comprise a tangible computer readable data storage device for storing, in a non-transitory manner, electronic personal health information and electronic source specific permission and conditions data; a tangible computer memory for storing of set of computer readable instructions; a network interface configured to facilitate communication between the first data provider and the multi-source health data integration logic; and a microprocessor configured to execute the computer readable instructions.

The system 100 may comprise a server. The server may comprise a tangible server readable data storage device for storing, in a non-transitory manner, the staging database; a tangible server memory for storing of set of server readable instructions including the multi-source health data integration logic; and a microprocessor configured to execute the server readable instructions. The server may comprise a tangible server readable data storage device for storing, in a non-transitory manner, the collaboration platform and warehoused data; a tangible server memory for storing of set of server readable instructions including the warehouse logic; and a microprocessor configured to execute the server readable instructions. The system may comprise a plurality of data providers . . . a second data provider 110B is shown in FIG. 23.

Referring to FIG. 25, the system may comprise an access interface 160A. The access interface may comprise an app market place 330A, graphic user interface 340A, and an SDK 330A. The app market place 330A may comprise user apps 331A and third party apps 332A. The graphic under interface 340A may comprise a homepage 341A and widgets 342A. The software development kit 300A may comprise natural language processing tools 311A, statistical tools 312A, data visualization tools 313A, relation and collaboration tools 314A, geospatial tools 315A, artificial intelligence, machine learning, and deep level modeling tools 316A, policy operationalization tools 317A, gaming scenario tools 318A, query engines 319A, project & task management tools 320A, import and export tools 321A, and data integrity and security tools 322A.

Figure 26:
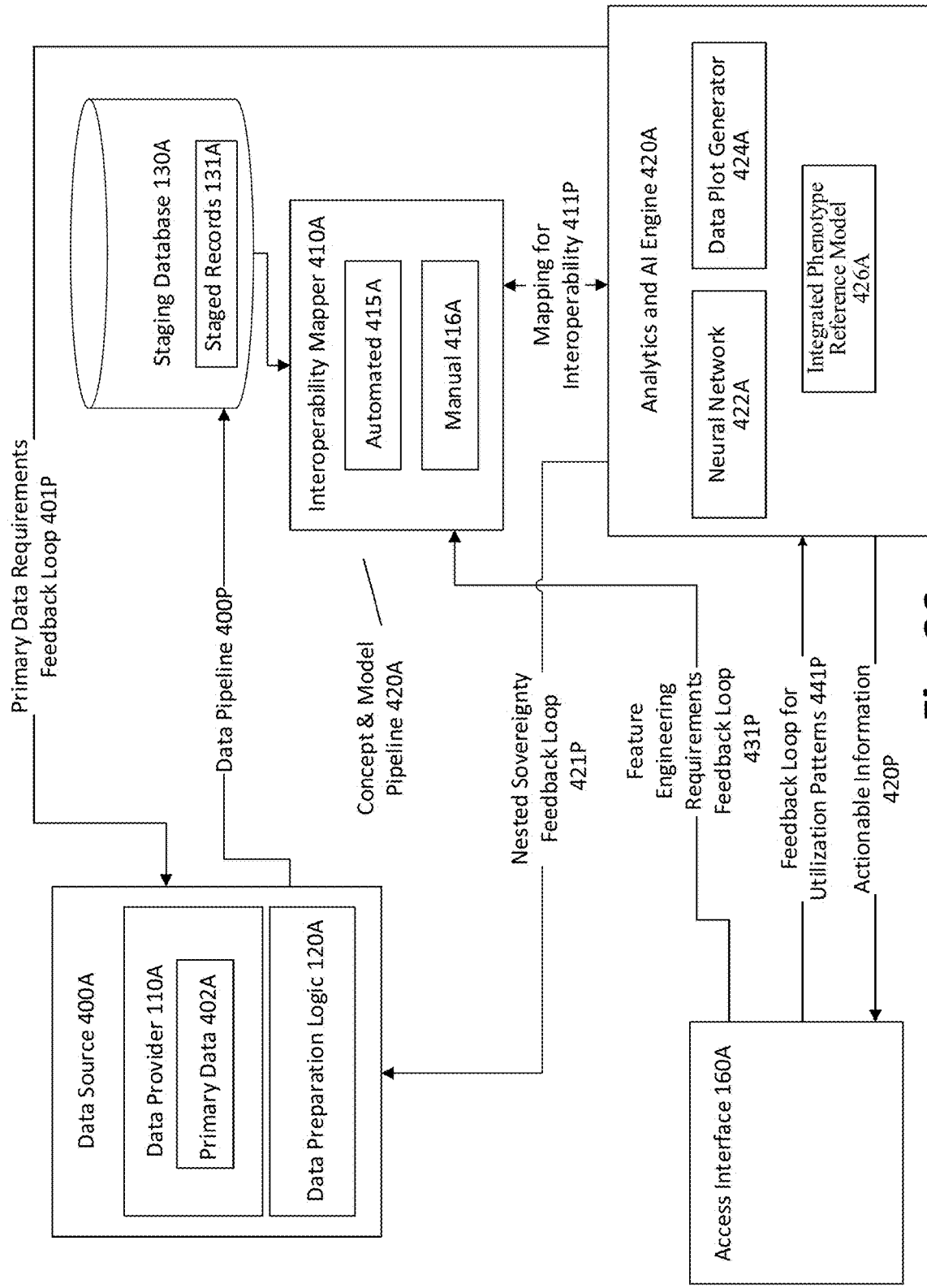
FIG. 26 shows a schematic view of data flow in an embodiment of the system.

Referring to FIG. 26, an exemplary system is shown comprising a data source 400A comprising a data provider 110A and multi-source health data integration logic 120A; a staging database 130A comprising staged records 131A. Said staging database may receive data from the data source 400a through a data pipelines 400P. The data source 400A may receive data back from analytics and AI engine 420A through a primary data requirements feedback loop 401P. The data source 400A may be configured to adjust its primary data 402A based on the primary data requirements feedback loop 401P. The system may comprise an interoperability mapper 410A configured to map data from the staging database 130A using at least one of an automated mapping process 415A or a manual mapping process 416A. The system may comprise an analytics and artificial intelligence engine 420A configured to receive and provide feedback regarding data mapped for interoperability 411P to and from the interoperability mapper 410A. The analytics and artificial intelligence engine 420A may comprise a neural network 422A; data plot generator 424A; and an integrated phenotype reference model 426A. The data preparation logic 120A may receive data back from the analytics and artificial intelligence engine through a nested sovereignty feedback loop 421P. The system may comprise an access interface 160A configured provide access to the integrated phenotype reference model 426A. The access interface 160A may receive actionable information 420P from the analytics and artificial intelligence engine 420A. The interoperability mapper 410A may be configured to receive data back from the access interface 160A through a feature engineering requirements feedback loop 431P. The analytics and artificial intelligence engine 420A may be configured to receive data back from the access interface 160A through a utilization patterns feedback loop 441P. The analytics and artificial intelligence engine 420A may be configured to adjust neural network 422A settings based on the utilization patterns. The data source 400A may be configured to receive data back from the analytics and artificial intelligence through a feature engineering requirements feedback loop; said data source may adjust data elements included in provided records based on the feature engineering requirements.

Figure 27:
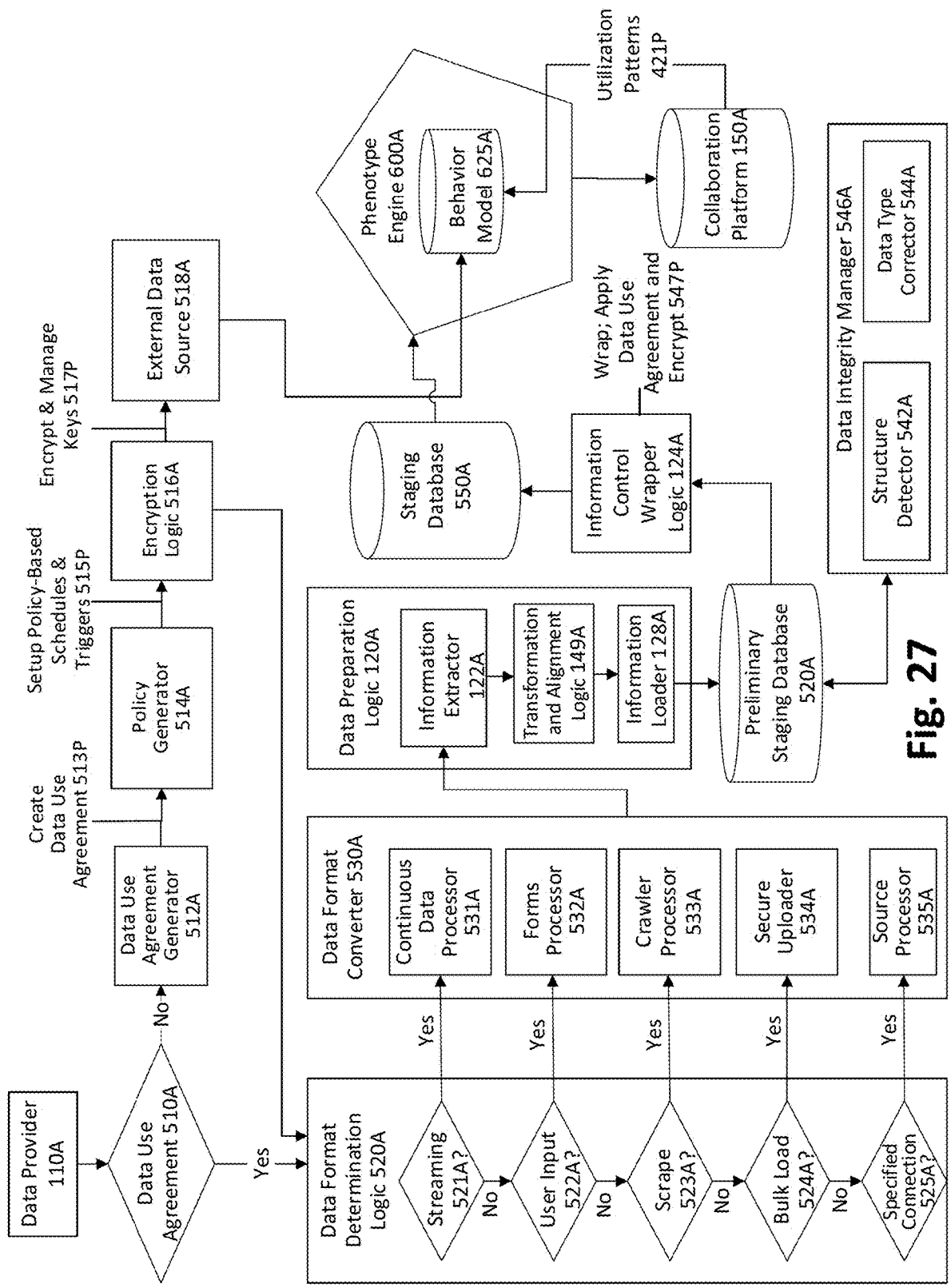
FIG. 27 shows a schematic view of data flow in an embodiment of the system.

FIG. 27 shows an exemplary system comprising: a data provider 110A configured to provide data in a data format; a data use agreement generator 512A configured to check whether the data provider 110A has an existing data use agreement 510A in place; and if not, generating a data use agreement 513P for the data provider. The system may comprise a policy generator 514A configured to setup policy-based schedules and triggers 515P; an encryption logic 516A configured to encrypt data & manage keys 517P for data from the data provider. The system may comprise a data format determination logic 521A configured to receive and determine a data format of the data sent by the data provider 110A. The data format selected from the list consisting essentially of: streaming 521A, user input 522A, scrape 523A, bulk load 524A and a specified connection 525A. They system may comprise a data format converter 530A configured to convert the data from the data provider to a common input format based on the data format determined by the data format determination logic. The data format converter 530A may comprise: a continuous data processor 531A, a forms processor 532A, a crawler processor 533A, a secure uploader 534A, and a source processor 535A. The system may comprise a multi-source health data integration logic 120A configured to generate prepared data based on received data converted by the data format converter. The multi-source health data integration logic may comprise an information extractor 122A, transformation and alignment logic 149A, and an information loader 128A. The system may comprise a preliminary staging database 520A configured to receive prepared data from the multi-source health data integration logic. The system may contain a data integrity manager 564A configured to maintain the integrity of data in the preliminary staging database. The data integrity manager 546A may comprise a structure detector 542A and a data type corrector 544A. The system may comprise an information control wrapper logic 124A configured to wrap the data from the preliminary staging database, apply the data use agreement, and encrypt the data. The system may comprise a staging database 550A configured to receive and store data from the information control wrapper logic. The system may comprise a phenotype engine 600A configured to receive data from the staging database. The system may comprise a collaboration platform 150A configured to receive data from the phenotype engine 600A. The phenotype engine 600A may comprise a behavior model 625A configured to receive utilization patterns from the collaboration platform 150A. The phenotype engine 600A may be configured to receive data from an external data source 518A. The external data source 518A may be configured to receive encrypted data from the encryption data logic.

Figure 28:
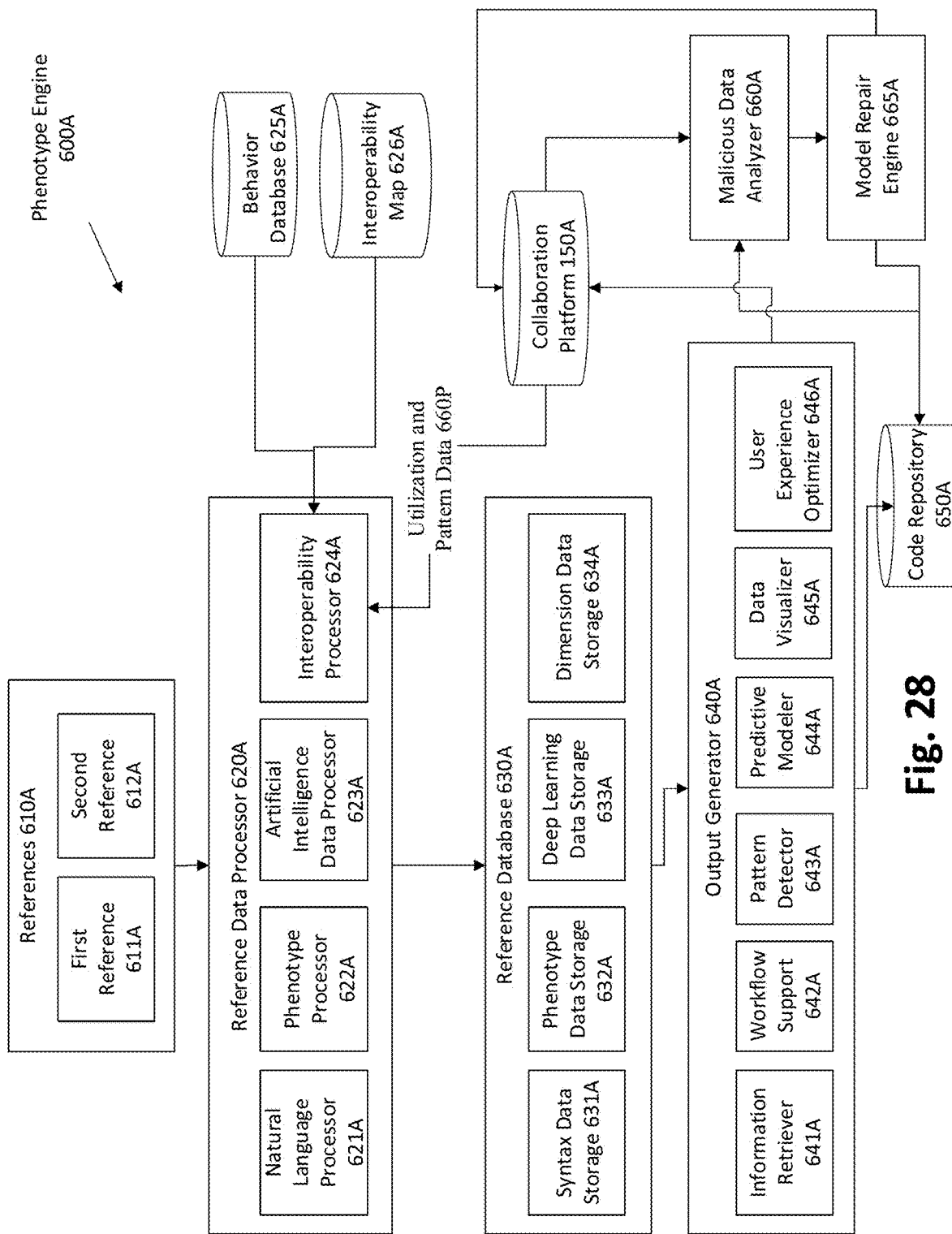
FIG. 28 shows an embodiment of the phenotype engine.

FIG. 28 illustrates a phenotype engine 600A. The phenotype engine may comprise a plurality of reference sources 610A. The first reference source 611A and second reference source 612A may comprise reference data. The phenotype engine 600A may comprise a reference data processor 620A comprising: a natural language processor 621A, phenotype processor 622A, artificial intelligence data processor 623A, and interoperability processor 624A. The phenotype processor may be configured to generate an integrated phenotype reference model (see FIG. 12B, 1220). The system may comprise a reference data processor 620A configured to access a behavior database 625A and an interoperability map 626A. The phenotype engine 600A may comprise a reference database 630A configured to receive processed data from the reference data processor 620A. The reference database 630A may comprise syntax data storage 631A, phenotype data storage 632A (for storing the integrated phenotype reference model 1220), deep learning data storage 633A, and dimension data storage 634A. The phenotype engine 600A may comprise an output generator 640A configured to output data. The output generator 640A may comprise an information retriever 641A, workflow support 624A, pattern detector 643A, predictive modeler 644A, data visualizer 645A, and user experience optimizer 646A. The phenotype engine may comprise a code repository 650A configured to receive output date from the output generator. The phenotype engine may comprise a collaboration platform 150A connected to an access platform. The collaboration platform 150A and access platform may be configured to provide access to the output data to a user. The interoperability processor 624A may configured to receive utilization and pattern data 660P from the collaboration platform 150A. The first reference 610A of the phenotype engine may comprise a first set of terminology, ontology, and encoding data, and the second reference includes a second set of terminology, ontology, and encoding data. The references may comprise an information exchange standardized model reference. The first reference may include a set of medical terminology, ontology, and encoding data, and the second reference may include a set of laboratory terminology, ontology, and encoding data. The behavior database 625A may comprise user data, input and behavior data, social network performance, and social network characteristics. The dimension data storage 634A may comprise common confirmed, fuzzy, and crisp dimension data. The syntax data storage 631A may comprise text annotation, indexing, winnowing, and accruing corpus characteristic data. The phenotype data storage 632A may comprise an integrated phenotype reference mode. The deep learning database 633A may comprise deep learning and machine learning data. The information retriever 641A may be configured to perform information retrieval and push processing. The workflow support 642A may be configured to provide clinical decision support and workflow support. The pattern detector 643A may be configured to provide pattern detection and anomaly detection. The predictive modeler 644A may be configured to generate spatiotemporal predicative models. The data visualizer 645A may be configured to provide data visualization and manipulation tools. The user experience optimizer 646A may be configured to optimize user experience and provide collaboration tools. The phenotype engine may comprise a reference source, wherein the reference source is a computer database. The database may contain a microprocessor, storage media, system memory, computer executable code, and networking hardware; said computer executable configured to cause the reference source to provide information to the reference database processor. The phenotype engine may comprise a server. The server may comprise a microprocessor, storage media, system memory, computer executable code, and networking hardware. The computer executable code may be configured to cause the microprocessor to implement the reference data processor, output generator, and collaboration platform.

Figure 29:
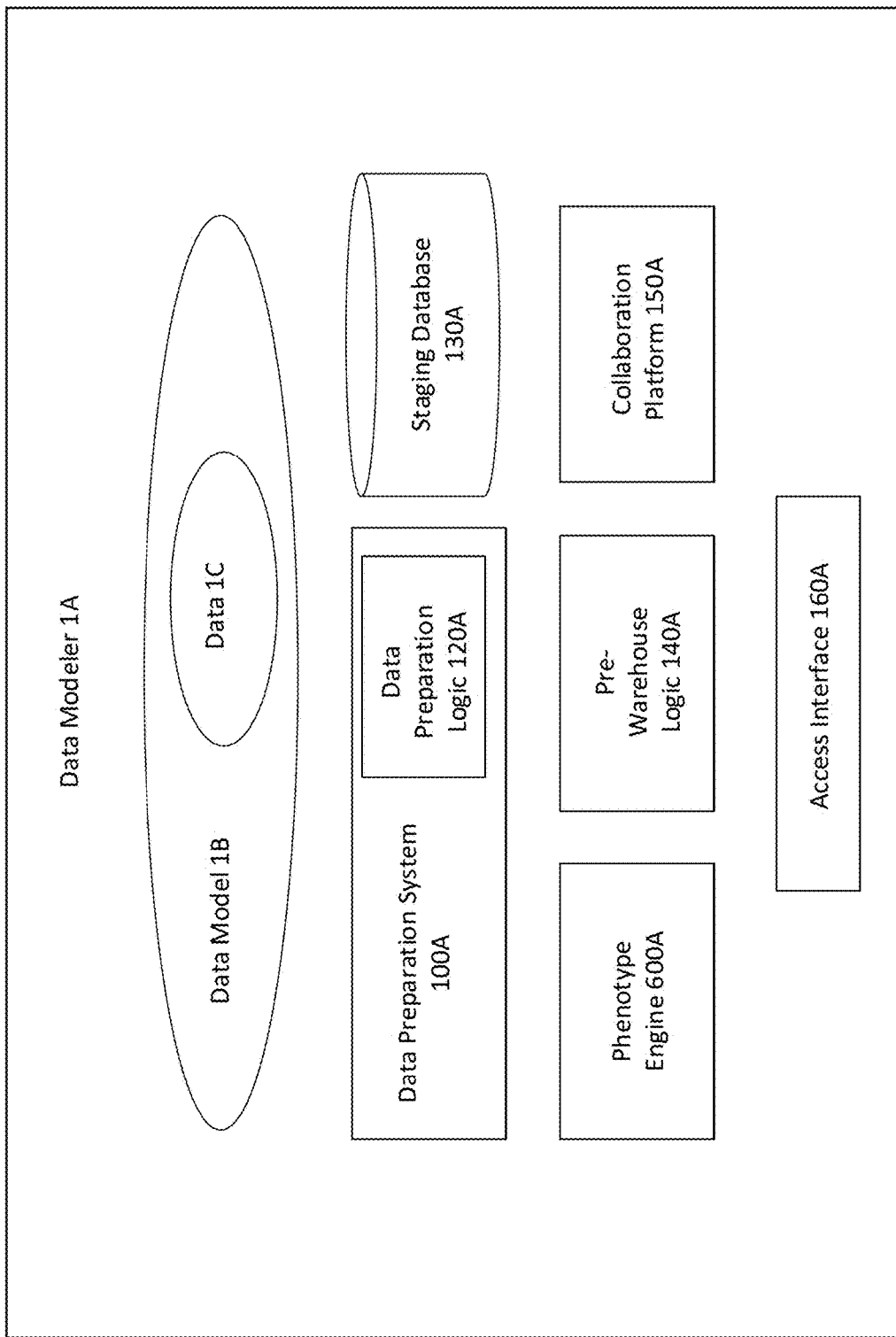
FIG. 29 shows a schematic view of the data modeler.

FIG. 29 illustrates a data modeler 1A that may be configured collect, prepare, aggregate, update, share, protect, and generate a model 1B (such as an integrated phenotype reference model 1220, see FIG. 12B) for users to access to improve their ability to conduct research and improve performance and accuracy of their research and/or services. In some configurations, the data modeler updates its generated model 1B (e.g. integrated phenotype reference model) based on the queries and access patterns of its users. The data model may be based on underlying data 1C. In some configurations, the data modeler 1A may comprise: a data preparation system 100A comprising data preparation logic 120A; staging database 130A for storing prepared data as staged records; phenotype engine 600A for generating a model such as an integrated phenotype reference model; pre-warehouse logic 140A for transforming, consolidating, conforming, dimensionalizing and codifying staged records; a collaboration platform 150A for storing warehoused data 141A; and an access interface 160A for providing access to the warehoused data and integrated phenotype reference model. In an example, the data modeler may be configured to collect the provider data, prepare the provider data, aggregate the provider data, update the warehoused data, share the warehoused data, protect the warehouse data, and generate an integrated phenotype reference model for users to access and conduct research via access interface.

Figure 32:
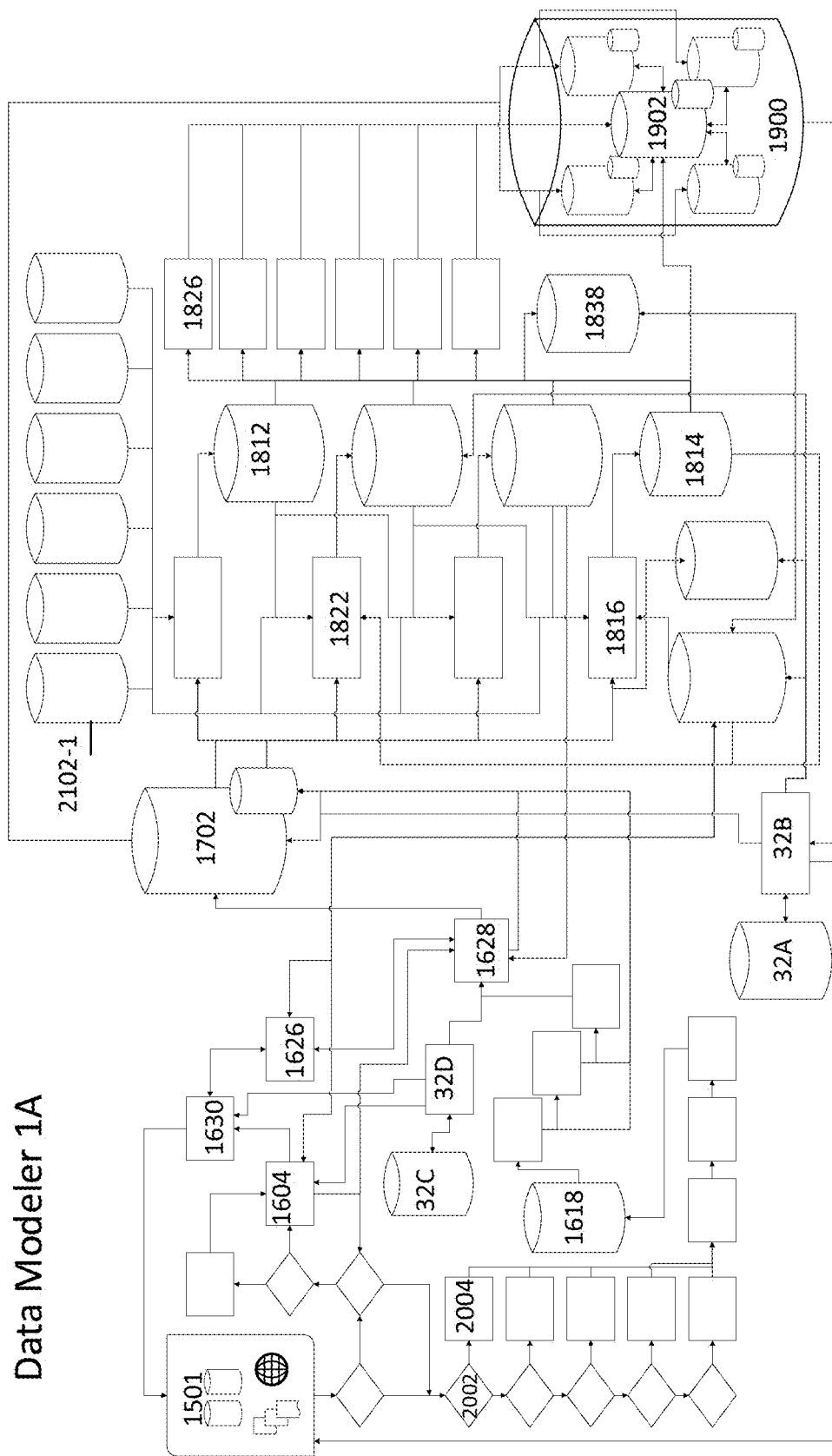
FIG. 32 shows a schematic diagram of the data modeler with details removed to show the entire modeler in one figure.

FIG. 32 shows a schematic diagram of the data modeler 1A with details removed to show the entire modeler in one figure. FIG. 32 basically represents an exemplary configured of FIGS. 17, 18, 19, and 20 in a single combined figure. Machine learning feedback data 32A, automated pipeline self-modification processing 32B, policy and standards repository 32C, policy and standards editor 32D are shown. Some example elements are included to help with understanding of this figure such 1812 (text annotation, indexing, windowing, and accruing corpus characteristics), phenotype processing 1822, data lake 1702, information retrieval and push processing 1826, derived market concept 1902, and data warehouse and collaborative network 1900.

Some aspects of the data modeler 1A do not need interoperability with every last data element. In some cases, the data modeler 1A finds and aligns concepts such as medical and public health (MPH) concepts and relevant law enforcement (LE) concepts. The integrated phenotype reference model may create a pattern language, rather than a dictionary per se, of the key concepts in medical and public health & law enforcement that can be cognitively manipulated, analogous to business concepts like customers or products or regional markets in other contexts.

The integrated phenotype reference model 1220 may be analogized to link charts & evidence boards which are popular in law enforcement television shows. A core phenotype may be one of the concepts on the board with a thumbtack and strings coming and going. In the integrated phenotype reference model, each core phenotype may then also include some satellite concepts that are related and frequently co-occur within the records. The "integrated" part of the integrated phenotype reference model may refer an association of medical, public health, and law enforcement sharing the same model. In some cases, their concepts and satellites overlap one another in a large network.

As an example, the medical and public health concept of opioid overdose has related satellite concepts such as heroin, fentanyl, needle exchange, transdermal, unconscious, naloxone, and myriad street names, but the phenotype may also include law enforcement concepts such as dealer and transnational cartel, etc. Other core concepts in the integrated phenotype reference model, such as the Sinaloa Cartel, could have overlapping satellites, such as a transnational cartel, and the satellites could then help to connect opioid overdose with the Sinaloa Cartel.

Consolidation logic (FIG. 23, 149A) may be configured to find and consolidate data that is to be aligned. The data lake 114 can have different kinds of contextual data and other models, and not all of it will always need alignment. Consolidation generally involves records, such as medical and law enforcement records in the data lake. Transformation and alignment logic may be used to align the core concepts within those records. FIG. 4 shows a consolidate step 412A which performs similar functions as the consolidate logic (FIG. 23, 149A).

Conformation logic (FIG. 23, 146A) may be configured to analyze source records to determine whether they are relevant to a recognized phenotype, optionally, within a degree of certainty. In other words, the conformation logic is where a source record is determined to be talking about a recognized phenotype, within a degree of certainty. The conformation logic is where the pre-warehouse logic 140A may index original data records (e.g. adding metadata) to the relevant phenotype in the integrated phenotype reference model, provide a degree of certainty, and tag evidence within the record (e.g., the words or phrases) that was used for the determination. FIG. 4 shows a confirmation step 412B which performs similar functions as the confirmation (FIG. 23, 146A).

In an example, if the data preparation system 100A were processing a record that included unconscious and naloxone, but nothing else, the pre-warehouse logic 140A, FIG. 23 or multi-source health data integration logic FIG. 1, 102 may index the record as a possible opioid overdose, with a certain confidence interval (e.g. 65% confidence), and tag or highlight those two words (unconscious and naloxone) in the record. Continuing the example, another record in the data warehouse 141B may contain information regarding unconscious and fentanyl. The pre-warehouse logic may similarly index to the opioid overdose phenotype, but with a lesser degree of confidence (e.g. maybe only 50% confidence.) In this example, the data preparation system 100A or the multi-source health data integration logic FIG. 1, 102 has conformed original disparate records into the same reference model. Such conformation facilitates data aggregation and/or data modeling. Thereby providing enhanced functional interoperability without manual mapping.

Dimensions are concepts the data modeler 1A may use within a model such as integrated phenotype reference model 1220, whether a core concept or a satellite concept. In aggregate, the dimensions may form a lexicon of words, phrases, lab tests, medications, diagnosis codes, etc., including synonyms and near synonyms, and including multilingual variants. Dimensionalization logic is configured to dimensionalize (provide dimensionalization) dimensions.

Dimensionalization may including tagging of the content or dimensions that the dimensionalization logic recognizes. Dimensionalization may be performed to facilitate conformation.

Codification logic 142A (or archive logic) may be configured to archive or store results (e.g. generate archived data) from the transformation and alignment logic 149A. E.g. the codification logic 142A may store how we got what we got out of the alignment process. If the data preparation system 100A, FIG. 23 (multi-source health data integration logic 102, FIG. 1) made a misidentification, or missed an important identification, the archived data generated by the codification logic 142A may provide sufficient information for the phenotype processor to rebuild the integrated phenotype reference model. The phenotype processor 622A may be configured to rebuild a part of the integrated phenotype reference model 1220 using the archived data. The phenotype processor 622A may be configured to analyze archived data and determine how a mistake occurred. In some embodiments, situations, codification logic will encode the archived data, rather than simply saving all the integrated phenotype references models and original data. The codification logic 142A may be configured to store enough information in that archived data so that the data preparation logic may rebuild the model (e.g. an integrated phenotype reference model) without having to save it in its entirety.

Rules of engagement may include a wrapper (e.g. a rules of engagement wrapper). In some examples, a rules of engagement wrapped is derived from the data use agreement (513P, FIG. 27). A rules of engagement data wrapper may determine how the data within the wrapper may be used. For example, the rules of engagement data wrapper may control which parts of the data (attribute-based access controls), by whom (role-based access controls), and under which circumstances (context-based access controls). Coupled with persistent encryption and provenance meta-data (explained below), these variables help construct a zero trust system. In some configurations, even a true zero-trust system may be developed. This may be preferable to systems that just rely on checking the user credentials (which are not true zero trust systems). Through the deployment of true zero trust system, collaborators can be marketplace competitors or lack any mutual trust.

Persistent encryption relates to securing the data itself, not just the perimeter of the data modeler 1A. In some configurations, persistent encryption embodiments may include system-wide persistent encryption . . . encryption that persists through the data modeler 1A.

Provenance may include a wrapper (e.g. a provenance wrapper). Data with a provenance wrapper may provenance information. Provenance information may provide the data modeler 1A with information concerning source or origin of the data. Data in the data preparation system 100A may be provided by data providers 110A. The provenance wrapper may indicate who these data providers are. Provenance information may be existent even in aggregated states. Provenance wrappers and/or provenance information may be used by data preparation logic 120A, phenotype engine 600A and other components of the data modeler 1A. Provence information may be used by the data modeler 1A to track and correct misinformation, disinformation, and malinformation throughout the data modeler and/or integrated phenotype reference model. Many modeling techniques in modern data science, particularly deep learning models, are nonlinear and can display chaotic dynamics (exquisite sensitivity on initial conditions). Such system may be vulnerable to data doping, which relates to intaking a dataset that has critical errors in it; critical errors designed to disrupt modeling in a way that is very difficult to discern. Tracking provenance allows the data modeler 1A to find all the data from a potential corrupted source, even when it has been aggregated and subsumed within integrated phenotype reference model, and reverse engineer its effects. The data modeler may comprise malicious data analyzer (FIG. 28) configured to detect misinformation, disinformation, and/malinformation. The data analyzer may be configured to use the provenance wrapper and/or provenance information to identify a source of the malicious data. The data modeler may comprise a model repair engine to remove and/or repair the malicious data. The malicious data analyzer 660A and model repair engine may be configured to interface with the code repository 650A, the collaboration platform 150A, or the data lake.

Sovereignty wrapping relates to the summary effect of rules of engagement, encryption, and provenance. Sovereignty wrapping provides a data owner with control (in some case absolute control) of their data. Data wrapped with a sovereignty wrap (e.g. including rules of engagement, encryption, and provenance) may be controlled by the data owner even if the data is removed from the data modeler 1A.

Dynamic policy operations (702G in the SDK of FIG. 7, 317A in FIG. 25) may provide nuance to the sovereignty. Granular access controls based on role and data attributes tend to evolve over time, depending on context, potentially dynamically in sometime in the context of a crisis, for example. Dynamic policies manage the evolving access requirements in real time by applying role- and attribute-based policies in accordance with the changing context.

Figure 30:
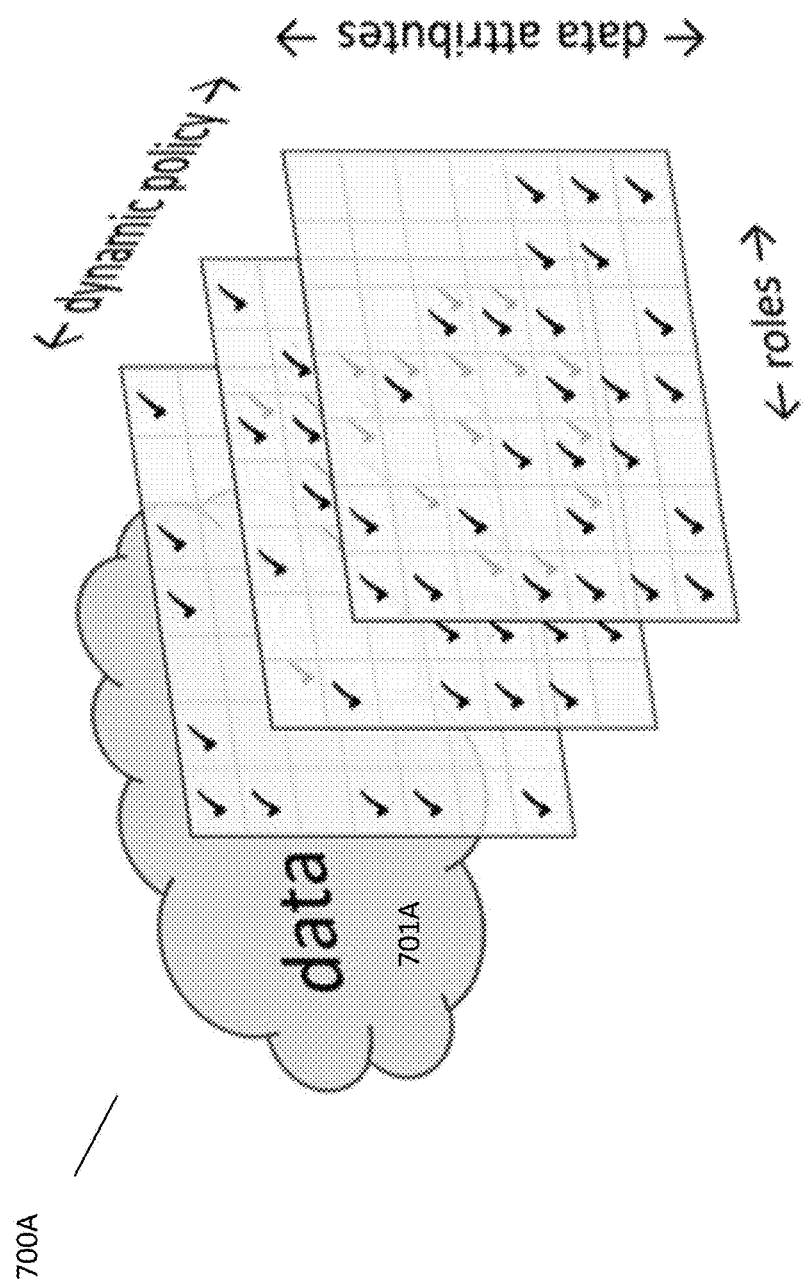
FIG. 30 shows an example of a sovereignty wrap.
Figure 31:
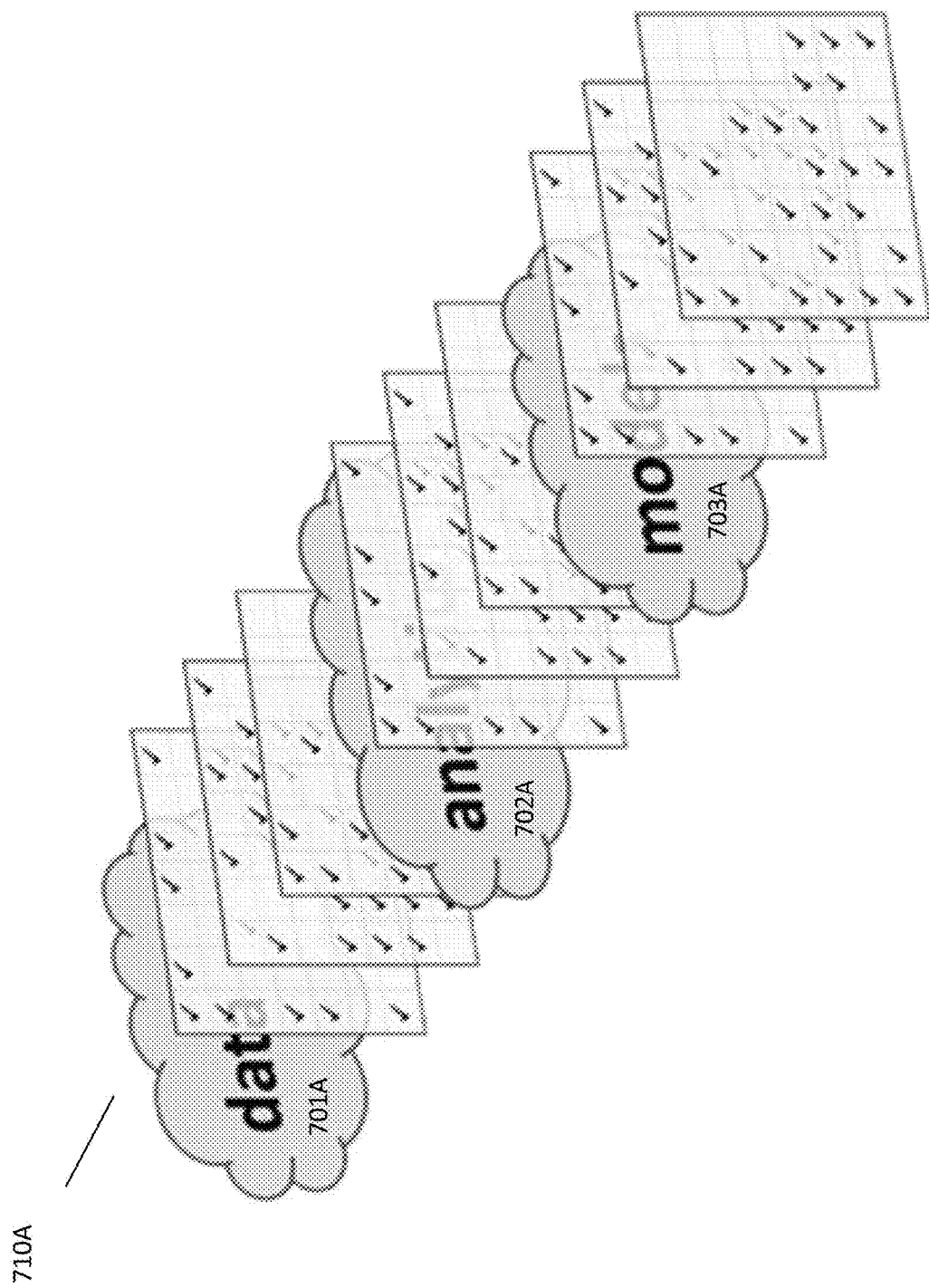
FIG. 31 shows an example of a nested sovereignty wrap.

FIG. 30 illustrates a schematic diagram of data sovereignty wrapping 700A. FIG. 30 illustrates a data cloud 701A. "Nested Sovereignty" (see FIG. 31) extends the nuance even further. Data is element 701A. Analytics is elements 702A. Models is elements 703A. Nested sovereignty 710A may be generated by feedback loop (122, FIG. 1 or 190P FIG. 23). Nested sovereignty may recognize different equities represented across the original data, the preliminary analytics, and the data's inclusion in larger models. Each step may add new value and new ownership, and each of the products may require sovereignty over that new value. Although shown below as a linear progression for clarity, the nested relationships can be branching.

As an example, imagine a patient arrives at the doctor's office for an appointment. The patient brings with them his/her demographics, complaints, and body. He or she should have complete sovereignty over that data, now and into the future. Now the doctor sees the patient and adds a considerable amount of value: retrieves subtleties of the symptoms, pulls out relevant aspects of the context, describes some astute physical findings, orders clarifying tests, and in the end, applies a label (diagnosis) to the situation. The patient does not own that work, the doctor does, but the patient still owns their original data. The doctor's data is irrelevant without the patient's, so these are not parallel values, but nested values, hence the need to develop nested sovereignty.

Continuing the example, now the data are pulled up by an analyst who has been surveilling for the peculiar physical findings that the doctor has recorded. The analyst then aggregates with similar cases and does some brilliant modeling that determines we have detected a new disease process, subtly buried in wrong diagnoses. Neither the patient nor the doctor owns this new value, although they do retain the value that they contributed. This notion of nested sovereignty has the effect of allowing control over raw data to be independent of the control of derivative data, as is needed when analysis on open-source data produces a classified result, for example.

As a side observation, nested sovereignty has the ability to create a new economic basis for medical data transactions: if the value of medical data can be controlled by its various owners, it can enter a free market where pharmaceutical companies, insurers, governments, and so own could purchase the data for their needs. In short, medical data can be commoditized and traded. Patients might receive royalties for the use of their data (think of the case of Henrietta Lacks), doctors can receive royalties for the astuteness of their observations and the quality of their records (sloppy and irrelevant data are rampant across medicine), and analysts could receive payment for the use of their results in improving the public's health. This is analogous to digital rights management of products in the entertainment industry.

The data modeler 1A, generated model 1B, and model data 1C can help unify medical and public health and law enforcement concepts using dimensions (from the lexicon). The essence of making subtle or unusual connections is that the data modeler 1A uses vector space to see what is in the neighborhood. Dimensions may be crafted precisely enough (despite possible linguistic variations) to be relatively independent of all other dimensions. Then a record that has been dimensionalized (tagged with all the dimensions found within it, each with an associated degree of confidence).

A vector calculator (FIG. 23, 144B) may produce a vector where the amplitude of the vector is determined by the frequency (count) with which that dimension occurred within the record. The vector calculator may include all dimensions together to create a vector for the record. The vector calculator may normalize the vector so that it has a total vector length of 1.0. The vector calculator may determine the cosine between vectors, an arithmetic problem, that can be performed by the vector calculator on the fly computationally. Close concepts in a neighborhood would have the smallest cosines between their vectors (i.e., they necessarily have overlapping satellite concepts in the integrated phenotype reference model). As some dimensions may include some degree of uncertainty, the vector that represents a record may be a bit fuzzy, so nearest neighborhood can be contextually tighter or looser. In FIGS. 10 and 26, five feedback loops are illustrated. In some configurations, they may be designed a single process with multiple inputs and outputs along with a storage capacity.

Referring to FIGS. 10 and 26, Loop 138 on FIG. 10 (441P on FIG. 26) goes from the GUI to the data warehouse and returns utilization patterns—which widgets and apps are getting the most use. Loop 130 (431P) goes from the data warehouse/collaborative platform/Access Interface 160A to the Analytics and AI Engine 420 and returns feature engineering and new phenotype connections. Loop 122 (421P) goes from the Analytics and AI Engine 420 to the Data Source (400A) and adds nested sovereignty information as analyses and models are built. Loop 123 (401P) goes from the Analytics and AI Engine to the source data owners and returns primary data requirements to them. FIG. 26 also shows a feedback loop, 411P, between the Analytics and AI Engine and the interoperability mapping processes, which uses the feedback to help speed up the manual mapping and to help refine the computed integrated phenotype reference model mapping.

The collaboration platform 150A may be configured to tracks how users behave on the data model 1A. For example, users may be frequently looking at (querying, discussing in threads, using dashboards, etc.) data that have been indexed to two concepts that the integrated phenotype reference model didn't have connections between. The machine learning algorithm flags a possible connection between the two concepts, but it's assumed to start with. As the behavior pattern gets reinforced with ongoing use, the machine learning presents the connection to the humans-in-the-loop involved with the interoperability and phenotyping processes who can validate it and perhaps note details as to the nature of the connection. When the new connection is validated, it becomes apparent that the connection was evident to subject matter experts but not intrinsic to the source data (otherwise the integrated phenotype reference model would already have detected the connection), so the humans can provide feedback to the source data owners suggesting that their primary data is not capturing an important relationship that subject matter experts on the platform are needing/leveraging. This provides an incentive to collect new source data or to modify (or clean up) data that is otherwise relevant but was somehow getting lost. The net result is the new source data can be used to make the connection evident to the integrated phenotype reference model algorithms, and the knowledge representation tightens up and becomes more relevant. This is an example of the human-machine collaboration intrinsic to the functioning of the platform—perhaps not unlike how the use of a car is inherently a human-machine collaboration.

Computer Program Product

A computer program product is an article of manufacture that has a computer-readable medium with executable program code that is adapted to enable a processing system to perform various operations and actions.

A computer-readable medium may be transitory or non-transitory.

A transitory computer-readable medium may be thought of as a conduit by which executable program code may be provided to a computer system, a short-term storage that may not use the data it holds other than to pass it on.

The buffers of transmitters and receivers that briefly store only portions of executable program code when being downloaded over the Internet is one example of a transitory computer-readable medium. A carrier signal or radio frequency signal, in transit, that conveys portions of executable program code over the air or through cabling such as fiber-optic cabling provides another example of a transitory computer-readable medium. Transitory computer-readable media convey parts of executable program code on the move, typically holding it long enough to just pass it on.

Non-transitory computer-readable media may be understood as a storage for the executable program code. Whereas a transitory computer-readable medium holds executable program code on the move, a non-transitory computer-readable medium is meant to hold executable program code at rest. Non-transitory computer-readable media may hold the software in its entirety, and for longer duration, compared to transitory computer-readable media that holds only a portion of the software and for a relatively short time. The term, "non-transitory computer-readable medium," specifically excludes communication signals such as radio frequency signals in transit.

The following forms of storage exemplify non-transitory computer-readable media: removable storage such as a universal serial bus (USB) disk, a USB stick, a flash disk, a flash drive, a thumb drive, an external solid-state storage device (SSD), a compact flash card, a secure digital (SD) card, a diskette, a tape, a compact disc, an optical disc;

secondary storage such as an internal hard drive, an internal SSD, internal flash memory, internal non-volatile memory, internal dynamic random-access memory (DRAM), read-only memory (ROM), random-access memory (RAM), and the like; and the primary storage of a computer system.

Different terms may be used to express the relationship between executable program code and non-transitory computer-readable media. Executable program code may be written on a disc, embodied in an application-specific integrated circuit, stored in a memory chip, or loaded in a cache memory, for example. Herein, the executable program code may be said, generally, to be "in" or "on" a computer-readable media. Conversely, the computer-readable media may be said to store, to include, to hold, or to have the executable program code.

Creation of Executable Program Code

Software source code may be understood to be a human-readable, high-level representation of logical operations. Statements written in the C programming language provide an example of software source code.

Software source code, while sometimes colloquially described as a program or as code, is different from executable program code. Software source code may be processed, through compilation for example, to yield executable program code. The process that yields the executable program code varies with the hardware processor; software source code meant to yield executable program code to run on one hardware processor made by one manufacturer, for example, will be processed differently than for another hardware processor made by another manufacturer.

The process of transforming software source code into executable program code is known to those familiar with this technical field as compilation or interpretation and is not the subject of this application.

User Interface

A computer system may include a user interface controller under control of the processing system that displays a user interface in accordance with a user interface module, i.e., a set of machine codes stored in the memory and selected from the predefined native instruction set of codes of the hardware processor, adapted to operate with the user interface controller to implement a user interface on a display device. Examples of a display device include a television, a projector, a computer display, a laptop display, a tablet display, a smartphone display, a smart television display, or the like.

The user interface may facilitate the collection of inputs from a user. The user interface may be graphical user interface with one or more user interface objects such as display objects and user activatable objects. The user interface may also have a touch interface that detects input when a user touches a display device.

A display object of a user interface may display information to the user. A user activatable object may allow the user to take some action. A display object and a user activatable object may be separate, collocated, overlapping, or nested one within another. Examples of display objects include lines, borders, text, images, or the like. Examples of user activatable objects include menus, buttons, toolbars, input boxes, widgets, and the like.

Communications

The various networks are illustrated throughout the drawings and described in other locations throughout this disclosure, can comprise any suitable type of network such as the Internet or a wide variety of other types of networks and combinations thereof. For example, the network may include a wide area network (WAN), a local area network (LAN), a wireless network, an intranet, the Internet, a combination thereof, and so on. Further, although a single network is shown, a network can be configured to include multiple networks.

CONCLUSION

For any computer-implemented embodiment, "means plus function" elements will use the term "means;" the terms "logic" and "module" have the meaning ascribed to them above and are not to be construed as generic means. An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features or methodological steps, it will be understood that the subject matter defined in the appended claims is not necessarily limited to the specific features or steps described. Rather, the specific features and steps are disclosed as example forms of implementing the claimed subject matter. To the extent headings appear in this description, they are for the convenience of the reader, not as limitations or restrictions of the systems, techniques, approaches, methods, or devices to those appearing in any section. Rather, the teachings and disclosures herein can be combined or rearranged with other portions of this disclosure and the knowledge of one of ordinary skill in the art. This disclosure generally encompasses and includes such variation. The indication of any elements or steps as "optional" does not indicate that all other or any other elements or steps are mandatory. The claims define the invention and form part of the specification. Limitations from the written description are not to be read into the claims.

Certain attributes, functions, steps of methods, or sub-steps of methods described herein may be associated with physical structures or components, such as a module of a physical device that, in implementations in accordance with this disclosure, make use of instructions (e.g., computer executable instructions) that may be embodied in hardware, such as an application-specific integrated circuit, or that may cause a computer (e.g., a general-purpose computer) executing the instructions to have defined characteristics. There may be a combination of hardware and software such as processor implementing firmware, software, and so forth, to function as a special purpose computer with the ascribed characteristics. For example, in embodiments a module may comprise a functional hardware unit (such as a self-contained hardware or software or a combination thereof) designed to interface the other components of a system such as through use of an application programming interface (API). In embodiments, structures for a module a module can be according to the module's function or set of functions, e.g., in accordance with a described algorithm. This disclosure may use nomenclature that associates a component or module with a function, purpose, step, or sub-step to identify the corresponding structure which, in instances, includes hardware and/or software that function for a specific purpose.

While certain implementations have been described, these implementations have been presented by way of example only and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure.

What is claimed is:

1. A data modeler for generating a model comprising:
a server; said server comprising:
   a tangible server readable data storage device for storing, in a non-transitory manner, a staging database;
   a tangible server memory for storing a set of server readable instructions including data preparation logic;
   a microprocessor configured to execute the server readable instructions;
   a first data provider configured to provide a data information file containing data;
   a multi-source health data integration logic configured to receive said data information file from the first data provider; the multi-source health data integration logic containing:
      an information extractor configured to extract information from the data information file;
      a phenotype engine configured to generate an integrated phenotype reference model:
      an information control wrapper logic configured to:
         wrap the data information file with an information control wrapper;
         apply a data use agreement; and
         encrypt the data;
      the information control wrapper configured to restrict usage of the data information file;
      a provenance wrapper comprising source information from the first data provider;
      the data modeler configured to track and correct misinformation through the integrated phenotype reference model by using the provenance wrapped source information;
      the multi-source health data integration logic configured to generate cleaned and sovereignty wrapped data wrapped with a sovereignty wrap;
   the staging database configured to receive the cleaned and sovereignty wrapped data from the multi-source health data integration logic; said staging database comprising:
      a plurality of staged records comprising the information control wrapper configured to restrict usage of the data information file;
      extracted information in a standardized format; wherein the extracted information contains electronic health records;
      metadata configured to provide details about the extracted information;
      the source information of the extracted information;
      ownership data comprising information about what data provider owns the extracted information;
      encryption data comprising information on how to encrypt the extracted information;
   pre-warehouse logic configured to receive said staged records from the staging database; said pre-warehouse logic comprising: codification logic; dimensionalization logic; conformation logic; consolidation logic, and transformation and alignment logic to transform and align related concepts; said transformation and alignment logic comprising a knowledge representation tool and an analysis tool; the pre-warehouse logic configured to generate transformed interoperable data;
   a collaboration platform configured to receive warehoused data; said collaboration platform comprising:
      a derived concept market containing warehoused data in conformed dimensions; and
      a bridge to provide transformed component data, transformed additional source data, hosted tele-collaboration data, and transformed third party models;
   an access interface configured to make said warehoused data and model accessible to a user; and
   said warehoused data accessible to the first data provider via the access interface;
   a primary data requirements feedback loop configured to send primary data requirements back to a data source from the staging database;
   the data source configured to adjust the data source's primary data based on the primary data requirements feedback loop;
   an interoperability mapper configured to:
      map data from the staging database using at least one of an automated mapping process and a manual mapping process; and
      receive feature engineering requirements data back from the access interface through a feature engineering requirements feedback loop; and
   an analytics and artificial intelligence engine configured to receive data mapped for interoperability from the interoperability mapper.

2. The data modeler of claim 1 wherein the first data provider is a computer comprising:
   a tangible computer readable data storage device for storing, in a non-transitory manner, electronic personal health information and electronic source specific permission and conditions data;
   a tangible computer memory for storing a set of computer readable instructions;
   a network interface configured to facilitate communication between the first data provider and the data preparation logic; and
   a microprocessor configured to execute the computer readable instructions.

3. The data modeler of claim 1 comprising a second data provider.

4. The data modeler of claim 1 further configured to collect the data information file, prepare the data information file, aggregate the data information file, update the warehoused data, share the warehoused data, protect the warehoused data, and generate an integrated phenotype reference model for users to access and conduct research via the access interface.

5. The data modeler of claim 1 wherein the access interface comprising: an app market place; a graphic user interface; and a software development kit.

6. The data modeler of claim 5 wherein:
the app market place comprises user apps and third party apps;
the graphic user interface comprises a homepage and widgets; and
the software development kit comprises natural language processing tool, statistical tools, data visualization tools, relation and collaboration tools, geospatial tools, artificial intelligence, machine learning, and deep level modeling tools, policy operationalization tools, gaming scenario tools, query engines, project & task management tools, import and export tools, and data integrity and security tools.

7. The data modeler of claim 1 wherein the codification logic is configured to:
archive data from the transformation and alignment logic and multi-source health data integration logic; the archived data generated by the codification logic providing sufficient information for a phenotype processor to rebuild an integrated phenotype reference model;
encode the archived data rather than saving all the integrated phenotype reference model and original data; and
store enough information in the archived data to rebuild the integrated phenotype reference model without having to save the integrated phenotype reference model in the integrated phenotype reference model's entirety.

8. The data modeler of claim 7 wherein the phenotype processor is configured to:
analyze archived data and determine how a mistake occurred; and
rebuild a part of the integrated phenotype reference model using the archived data without having to save the integrated phenotype reference model in the integrated phenotype reference model's entirety.

9. The data modeler of claim 8 wherein said staging database is configured to:
receive data from the first data provider through a data pipeline; and
adjust the staged records based on the feature engineering requirements data.

10. The data modeler of claim 9 wherein the analytics and artificial intelligence engine comprises a neural network; data plot generator; and an integrated phenotype reference model.

11. The data modeler of claim 10 wherein the analytics and artificial intelligence engine is configured to:
receive utilization patterns data back from the access interface through a utilization patterns feedback loop; and
adjust neural network settings based on the utilization patterns data.

12. The data modeler of claim 1 comprising a data use agreement generator configured to check whether the first data provider has an existing data use agreement in place; and if not, generating a data use agreement for the first data provider; and a policy generator configured to setup policy-based schedules and triggers.

13. The data modeler of claim 1 comprising a data format converter containing a continuous data processor, a forms processor, a crawler processor, a secure uploader, and a source processor.

14. The data modeler of claim 13 wherein the data format converter is configured to convert the data from the first data provider to an input format based on a data format determined by a data format determination logic.

15. The data modeler of claim 1 further comprising:
a reference data processor comprising: a natural language processor, phenotype processor, artificial intelligence data processor, and interoperability processor; the reference data processor configured to access a behavior database and an interoperability map;
a reference database configured to receive processed data from the reference data processor; said reference database comprising syntax data storage, phenotype data storage, deep learning data storage, and dimension data storage;
a pattern detector configured to provide pattern detection and anomaly detection;
a predictive modeler configured to generate spatiotemporal predicative models;
a data visualizer configured to provide data visualization and manipulation tools;
a user experience optimizer configured to optimize user experience and provide collaboration tools; and
a code repository configured to receive output data from an output generator.

16. The data modeler of claim 15 wherein:
the collaboration platform and access platform is configured to provide access to the output data to the user; and
the interoperability processor configured to receive utilization and pattern data from the collaboration platform.

17. The data modeler of claim 1 wherein:
the sovereignty wrap comprises: rules of engagement, encryption, and provenance; and data that has been sovereignty wrapped; and
the sovereignty wrapped data is controllable by an owner of the sovereignty wrapped data during and after the data has been removed from the data modeler.

18. The data modeler of claim 1 comprising:
multilevel, persistent, embedded cybersecurity for sequestering electronic personal health information (ePHI);
automated enforcement of rules of engagement through tracked data provenance through an analysis pipeline and persistent encryption;
a staging database first logic portion storing generic transformed (GTR) electronic health record (EHR) system sourced ePHI data and GTR EHR metadata; and
a sovereignty protective wrap protecting the GTR EHR system sourced ePHI and GTR EHR metadata against unauthorized access to GTR EHR system sourced ePHI and GTR EHR metadata.

19. The data modeler of claim 18 comprising:
a rules of engagement data wrapper around the data for determining rules of engagement;
the rules of engagement configured to define how the data within the rules of engagement data wrapper may be used; and
the rules of engagement data wrapper controlling:
which parts of the data may be used through attribute-based access controls;
who may use the data through role-based access controls; and
under which conditions the data may be used through context-based controls; and automated enforcement of the rules of engagement.

20. The data modeler of claim 1 comprising:
an artificial intelligence enhanced medical record exchange configured to curate data through a combination of multi-source health data integration logic, data extraction by a data extraction logic, sovereignty protective wrapping by a wrapping logic, and multiple participant collaboration hosted by a virtual collaboration platform;
the artificial intelligence enhanced medical record exchange configured to bring medical data and contextual data, analytics, decisions, and collaboration from across multiple sources onto a single secure medical information platform; and
the multi-source health data integration logic configured to receive electronic personal health information carried in electronic health records (EHRs) in various forms and file structures maintained by a plurality of different mutually independent electronic health record systems.

21. A method of generating a model comprising:
a first data provider generating a data information file containing data;
a multi-source health data integration logic receiving said data information file from the first data provider;
a phenotype engine generating an integrated phenotype reference model:
an information extractor extracting information from the data information file;
an information control wrapper logic wrapping the data information file with an information control wrapper;
applying a data use agreement; and encrypting the data;
the information control wrapper restricting usage of the data information file;
providing a data modeler with provenance information concerning source of the data;
tracking and correcting misinformation within the integrated phenotype reference model through the use of the provenance information;
the multi-source health data integration logic generating cleaned and sovereignty wrapped data;
a staging database receiving the cleaned and sovereignty wrapped data from the multi-source health data integration logic; said staging database comprising:
  a plurality of staged records comprising the information control wrapper configured to restrict usage of the data information file;
  extracted information in a standardized format; wherein the extracted information contains electronic health records;
  metadata configured to provide details about the extracted information;
  origin data comprising source information of the extracted information;
  ownership data comprising information about what data provider owns the extracted information;
  encryption data comprising information on how to encrypt the extracted information;
pre-warehouse logic receiving said staged records from the staging database; said pre-warehouse logic comprising: codification logic; dimensionalization logic; conformation logic; consolidation logic, and transformation and alignment logic to transform and align related concepts; said transformation and alignment logic comprising a knowledge representation tool and an analysis tool; the pre-warehouse logic configured to generate transformed interoperable data;
a collaboration platform receiving warehoused data; said collaboration platform comprising:
  a derived concept market containing warehoused data in conformed dimensions; and
  a bridge providing transformed component data, transformed additional source data, hosted telecollaboration data, and transformed third party models; and
an access interface making said warehoused data and model accessible to a user;
a primary data requirements feedback loop sending send primary data requirements data back to a data source from the staging database;
the data source adjusting the data sources's primary data based on the primary data requirements feedback loop;
an interoperability mapper mapping data from the staging database using at least one of an automated mapping process and a manual mapping process;
the interoperability mapper receiving feature engineering requirements data back from the access interface through a feature engineering requirements feedback loop; and
an analytics and artificial intelligence engine receiving data mapped for interoperability from the interoperability mapper.

22. The method of claim 21 comprising:
collecting the data information file;
preparing the data information file;
aggregating the data information file;
updating the warehoused data;
sharing the warehoused data;
protecting the warehoused data; and
generating an integrated phenotype reference model for users to access and conduct research via the access interface.

23. The method of claim 21 comprising:
archiving data from the transformation and alignment logic and multi-source health data integration logic; the archived data generated by the codification logic providing sufficient information for a phenotype processor to rebuild an integrated phenotype reference model;
encoding the archived data rather than saving all the integrated phenotype reference model and original data; and
storing enough information in the archived data to rebuild the integrated phenotype reference model without having to save the integrated phenotype reference model in the integrated phenotype reference model's entirety.

24. The method of claim 22 comprising:
a phenotype processor analyzing archived data and determining how a mistake occurred; and
the phenotype processor rebuilding a part of the integrated phenotype reference model using the archived data without having to save the integrated phenotype reference model in the integrated phenotype reference model's entirety.

25. The method of claim 24 comprising:
receiving data from the first data provider through a data pipeline;
adjusting the staged records based on the feature engineering requirements data; and
adjusting primary data based on a primary data requirements feedback loop.

26. The method of claim 25 comprising:
receiving utilization patterns data back from the access interface through a utilization patterns feedback loop; and
adjusting settings in a neural network-based on the utilization patterns data.

27. The method of claim 21 comprising:
checking whether the first data provider has an existing data use agreement in place; and if not, generating a data use agreement for the data provider; and
setup policy-based schedules and triggers with a policy generator.

28. The method of claim 21 comprising a data format converter converting the data from the first data provider to an input format based on a data format determined by a data format determination logic.

29. The method of claim 21 comprising:
a reference data processor accessing a behavior database and an interoperability map; and
a reference database receiving processed data from the reference data processor; said reference database comprising syntax data storage, phenotype data storage, deep learning data storage, and dimension data storage;

a pattern detector providing pattern detection and anomaly detection;

a predictive modeler generating spatiotemporal predictive models;

a data visualizer providing data visualization and manipulation tools;

a user experience optimizer optimizing user experience and providing collaboration tools; and a code repository receiving output data from an output generator.

30. The method of claim 29 comprising:

the collaboration platform and access platform providing access to the output data to a user; and an interoperability processor receiving utilization and pattern data from the collaboration platform.

31. The method of claim 21 comprising an owner of the data controlling the sovereignty wrapped data while the data is in the data modeler;

removing the sovereignty wrapped data from the data modeler;

the owner of the data controlling the sovereignty wrapped data after the sovereignty wrapped data has been removed from the data modeler;

wherein the sovereignty wrap comprises: rules of engagement, encryption, and provenance; and data that has been sovereignty wrapped.

32. The method of claim 21 comprising:

determining rules of engagement defining how the data within a rules of engagement data wrapper be used;

the rules of engagement data wrapper controlling:
which parts of the data may be used through attribute-based access controls;
who may use the data through role-based access controls; and
under which conditions the data may be used through context-based controls; and automating enforcement of the rules of engagement by tracking data provenance through an analysis pipeline and using a persistent encryption method.

33. The method of claim 32 comprising:

providing multilevel, persistent, embedded cybersecurity by sequestering electronic personal health information (ePHI);

tracking data provenance in the integrated phenotype reference model;

enforcing the rules of engagement for all users of the integrated phenotype reference model;

a staging database first logic portion storing generic transformed (GTR) electronic health record (EHR) system sourced ePHI data;

protecting sovereignty of GTR EHR system sourced ePHI and GTR EHR metadata; and protecting against unauthorized access to GTR EHR system sourced ePHI and GTR EHR metadata.

34. The method of claim 21 comprising:

an artificial intelligence enhanced medical record exchange curating data through a combination of multi-source health data integration logic, data extraction by a data extraction logic, sovereignty protective wrapping by a wrapping logic, and multiple participant collaboration hosted by a virtual collaboration platform;

the artificial intelligence enhanced medical record exchange bringing medical data and contextual data, analytics, decisions, and collaboration from across multiple sources onto a single secure medical information platform; and the multi-source health data integration logic receiving electronic personal health information carried in electronic health records (EHRs) in various forms and file structures maintained by a plurality of different mutually independent electronic health record systems.

* * * * *